(12) United States Patent
Bolli et al.

(10) Patent No.: US 8,580,824 B2
(45) Date of Patent: *Nov. 12, 2013

(54) PYRIDIN-4-YL DERIVATIVES AS IMMUNOMODULATING AGENTS

(75) Inventors: Martin Bolli, Allschwil (CH); David Lehmann, Galmiz (CH); Boris Mathys, Pratteln (CH); Claus Mueller, Weil am Rhein (DE); Oliver Nayler, Arlesheim (CH); Beat Steiner, Dornach (CH); Jörg Velker, Huningue (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 790 days.

This patent is subject to a terminal disclaimer.

(21) Appl. No.: 12/310,801

(22) PCT Filed: Sep. 6, 2007

(86) PCT No.: PCT/IB2007/053594
§ 371 (c)(1),
(2), (4) Date: Sep. 30, 2009

(87) PCT Pub. No.: WO2008/029371
PCT Pub. Date: Mar. 13, 2008

(65) Prior Publication Data
US 2010/0063108 A1 Mar. 11, 2010

(30) Foreign Application Priority Data
Sep. 7, 2006 (WO) .................. PCT/IB2006/053147

(51) Int. Cl.
*A61K 31/443* (2006.01)
*C07D 413/04* (2006.01)

(52) U.S. Cl.
USPC ....................................... 514/340; 546/269.4

(58) Field of Classification Search
USPC ........................................ 546/269.4; 514/340
See application file for complete search history.

(56) References Cited

U.S. PATENT DOCUMENTS

| | | | |
|---|---|---|---|
| 3,647,809 A | 3/1972 | Reiter et al. | |
| 5,708,180 A | 1/1998 | Beck et al. | |
| 7,605,171 B2 | 10/2009 | Colandrea et al. | |
| 8,003,800 B2 | 8/2011 | Bolli et al. | |
| 8,044,076 B2 | 10/2011 | Bolli et al. | |
| 8,133,910 B2 | 3/2012 | Bolli et al. | |
| 8,288,554 B2 * | 10/2012 | Bolli et al. | 546/268.7 |
| 8,299,086 B2 | 10/2012 | Bolli et al. | |
| 2004/0058894 A1 | 3/2004 | Doherty et al. | |
| 2007/0021443 A1 | 1/2007 | Ohlmeyer | |
| 2007/0043014 A1 | 2/2007 | Doherty et al. | |
| 2007/0043104 A1 | 2/2007 | Luthman et al. | |
| 2007/0270438 A1 | 11/2007 | Bhattacharya et al. | |
| 2008/0064740 A1 | 3/2008 | Bolli et al. | |
| 2008/0176926 A1 | 7/2008 | Bolli et al. | |
| 2008/0194670 A1 | 8/2008 | Bolli et al. | |
| 2008/0249093 A1 | 10/2008 | Colandrea et al. | |
| 2008/0300294 A1 | 12/2008 | Bolli et al. | |
| 2008/0306124 A1 | 12/2008 | Albert et al. | |
| 2008/0318955 A1 | 12/2008 | Bolli et al. | |
| 2009/0005421 A1 | 1/2009 | Bolli et al. | |
| 2009/0275554 A1 | 11/2009 | Habashita et al. | |
| 2010/0048648 A1 | 2/2010 | Bolli et al. | |
| 2010/0075946 A1 | 3/2010 | Bolli et al. | |
| 2010/0087417 A1 | 4/2010 | Bolli et al. | |
| 2010/0087495 A1 | 4/2010 | Bolli et al. | |
| 2010/0168005 A1 | 7/2010 | Bolli et al. | |
| 2010/0234346 A1 | 9/2010 | Bolli et al. | |
| 2010/0240717 A1 | 9/2010 | Boli et al. | |
| 2010/0261702 A1 | 10/2010 | Bolli et al. | |
| 2010/0331372 A1 | 12/2010 | Bolli et al. | |
| 2011/0028448 A1 | 2/2011 | Bolli et al. | |
| 2011/0028449 A1 | 2/2011 | Bolli et al. | |
| 2011/0046170 A1 | 2/2011 | Bolli et al. | |
| 2011/0212998 A1 | 9/2011 | Bolli et al. | |
| 2012/0108638 A1 | 5/2012 | Bolli et al. | |

FOREIGN PATENT DOCUMENTS

| | | |
|---|---|---|
| DE | 10237883 | 3/2004 |
| EP | 0476646 | 3/1992 |
| EP | 0702003 | 6/1998 |
| EP | 1873153 | 1/2008 |
| JP | 2008120794 | 5/2008 |
| WO | WO91/15583 | 10/1991 |
| WO | WO99/46277 | 9/1999 |
| WO | WO 00/45799 | 8/2000 |
| WO | WO 01/12627 | 2/2001 |
| WO | WO 02/068417 | 9/2002 |

(Continued)

OTHER PUBLICATIONS

Hla et al., An abundant transcript induced in differentiating human endothelial cells encodes a polypeptide with structural similarities to G-protein-coupled receptors, J. Biol. Chem. (1990) vol. 265, No. 16, pp. 9308-9313.

(Continued)

*Primary Examiner* — Patricia L Morris
(74) *Attorney, Agent, or Firm* — Hoxie & Associates LLC

(57) ABSTRACT

The invention relates to pyridine derivatives of Formula (I) wherein A, $R^1$, $R^2$, $R^3$, $R^4$, $R^5$, and $R^6$ are as described in the description, their preparation and their use as pharmaceutically active compounds. Said compounds particularly act as immunomodulating agents.

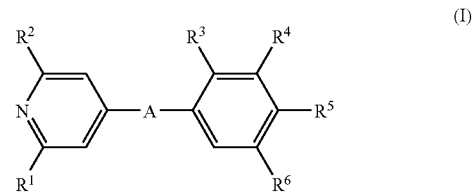

18 Claims, No Drawings

(56) References Cited

FOREIGN PATENT DOCUMENTS

| | | |
|---|---|---|
| WO | WO03/062248 | 7/2003 |
| WO | WO 03/062252 | 7/2003 |
| WO | WO 03/105771 | 12/2003 |
| WO | WO2004/035538 | 4/2004 |
| WO | WO2004/056789 | 7/2004 |
| WO | WO2004/103279 | 12/2004 |
| WO | WO2005/014525 | 2/2005 |
| WO | WO2005/032465 | 4/2005 |
| WO | WO2005/058848 | 6/2005 |
| WO | WO 2005/115382 | 12/2005 |
| WO | WO 2006/047195 | 5/2006 |
| WO | WO2006/100631 | 9/2006 |
| WO | WO2006/114400 | 11/2006 |
| WO | WO 2006/115188 | 11/2006 |
| WO | WO2006/131336 | 12/2006 |
| WO | WO2007/001973 | 1/2007 |
| WO | WO2007/085451 | 8/2007 |
| WO | WO 2007/098474 | 8/2007 |
| WO | WO 2007/132307 | 11/2007 |
| WO | WO 2008/029370 | 3/2008 |
| WO | WO2008/029370 | 3/2008 |
| WO | WO2008/035239 | 3/2008 |
| WO | WO2008/037476 | 4/2008 |
| WO | WO2008/076356 | 6/2008 |
| WO | WO2008/091967 | 7/2008 |
| WO | WO 2009/151529 | 12/2009 |
| WO | WO 2011/007324 | 1/2011 |

OTHER PUBLICATIONS

Gould, Salt selection for basic drugs, Int'l. J. Pharmaceutics (1986) vol. 33, pp. 201-217.

Mentzel et al., N-methoxy-N-methylamides (weinreb amides) in modern organic synthesis, J. Prakt. Chem. (1997) vol. 339, pp. 517-524.

Singh et al., The growing synthetic utility of weinreb's amide, J. Prakt. Chem. (2000) vol. 342, No. 4, pp. 340-347.

Khlestkin et al., Recent advances in the application of N,O-Dialkylhydroxylamines in organic chemistry, Current Organic Chemistry (2003) vol. 7, pp. 967-993.

Gangloff et al., Synthesis of 3,5-disubstituted-1,2,4-oxadiazoles using tetrabutylammonium fluoride as a mild and efficient catalyst, Tetrahedron Letters (2001) vol. 42, pp. 1441-1443.

Suzuki et al., Synthesis of the selective 5-hydroxytryptamine 4 (5-HT$_4$) receptor agonist (+)-(S)-2-chloro-5-methoxy-4-[5-(2-piperidylmethyl)-1,2,4- oxadiazol-3-yl]aniline, Chem. Pharm. Bull. (1999) vol. 47, No. 1, pp. 120-122.

Poulain et al., Parallel synthesis of 1,2,4-oxadiazoles from carboxylic acids using an improved, uranium-based, activation, Tetrahedron Letters (2001) vol. 42, pp. 1495-1498.

Srivastava et al., Synthesis of 3-aryl-5[thien-3-yl methy1]-1,2,4-oxadiazoles, Synthetic Comm. (1999) vol. 29, No. 9, pp. 1437-1450.

John et al., Reactions of (difluroramino) difluroacetonitrile and (difluroamino) difluoracetamidoxime, Inorg. Chem. (1988) vol. 27, pp. 3100-3104.

Kaboudin et al., One-pot synthesis of 1,2,4-oxadiazoles mediated by microwave irradiation under solvent-free condition, Heterocycles (2003) vol. 60, No. 10, pp. 2287-2292.

Hamze et al., Synthesis of various 3-substituted 1,2,4-oxadiazole-containing chiral β$^3$- and α-amino acides from Fmoc-protected aspartic acid, J. Org. Chem. (2003) vol. 68, pp. 7316-7321.

Brain et al., Novel procedure for the synthesis of 1,3,4-oxadiazoles from 1,2-diacylhydrazines using polymer-supported Burgess reagent under microwave conditions, Tetrahedron Letters (1999) vol. 40, pp. 3275-3278.

Meyer et al., Synthesis of new 1,2,4- and 1,3,4-oxadiazole derivatives, Synthesis (2003), No. 6, pp. 899-905.

Garca et al., Synthesis, biological evaluation, and three-dimensional quantitative structure-activity relationship study of small-molecule positive modulators of adrenomedullin, J. Med. Chem. (2005) vol. 48, No. 12, pp. 4068-4075.

Kiryanov et al., Synthesis of 2-alkoxy-substituted thiophenes, 1,3-thiazoles, and related S-heterocycles via Lawesson's reagent-mediated cyclization under microwave irradiation: applications for liquid crystal synthesis, J. Org. Chem. (2001) vol. 66, No. 23, pp. 7925-7929.

Sato et al., Synthesis and evaluation of substituted 4-alkoxy-2-aminopyridines as novel neuropeptide Y1 receptor antagonists, Bioorg. & Med. Chem. Letters (2004) vol. 14, pp. 1761-1764.

La Mattina, The synthesis of 2-amino-4-(4-imidazoly)pyridines, J. Heterocyclic Chem. (1983) vol. 20, pp. 533-538.

Pesson et al., Antibacteriens de synthese—derives de l'acide pipemidique, Eur. J. Med. Chem. (1980) vol. 15, No. 3, pp. 263-268.

Furstner et al., Iron-catalyzed cross-coupling reactions, J. Am. Chem. Soc. (2002) vol. 124, No. 46, pp. 13856-13863.

Furstner et al., Iron-catalyzed cross-coupling reactions of alkyl-grignard reagents with aryl chlorides, tosylates, and triflates, Angew. Chem. (2002) vol. 41, No. 4, pp. 609-612.

Wild et al., Asymmetric synthesis of (S)-(—)-acromelobic acid, Eur. J. Org. Chem. (2003) pp. 4445-4449.

Kerins et al., Generation of substituted sryrenes via Suzuki cross-coupling of aryl halides with 2,4,6-trivinylcyclotriboroxane, J. Org. Chem. (2002) vol. 67, No. 14, pp. 4968-4971.

Trapani et al., Propofol analogues, J. Med. Chem. (1998) vol. 41, pp. 1846-1854.

Chakraborti et al., One-pot synthesis of nitriles from aldehydes under microwave irradiation: influence of the medium and mode of microwave irradiation on product formation. Tetrahedron (1999) vol. 55, pp. 13265-13268.

Roth et al., 2-4-Diamino-5-benzylpyrimidines and analogs as antibacterial agents, J. Med. Chem. (1988), vol. 31, No. 1, pp. 122-129.

Ecke et al., *ortho*-Alkylation of aromatic amines, J. Org. Chem. (1957) vol. 22, pp. 639-642.

Xu et al., Acyclic analogues of adenosine bisphosphates as P2Y receptor antagonists: phosphate substitution leads to multiple pathways of inhibition of platelet aggregation, J. Med. Chem. (2002) vol. 45, pp. 5694-5709.

Yan et al., Discover of 3-aryipropionic acids as potent agonists of sphingosine-1-posphate receptor-1 (S1P$_1$) with high selectivity against all other known S1P receptor subtypes, Bioorg. Med. Chem. Letters (2006) vol. 16, pp. 3679-3683.

Alvernhe et al; "Synthesis and Reactivity of 3-chloro-3-trifluoromethylacroleins: Stabilization of the Tetrahedral Intermediate in a Nucleophilic Vinylic "Substitution""; Bull. Soc. Chim. Fr.; 131, 1994, 167-172.

Cui et al; Design and Synthesis of Highly Constrained Factor Xa Inhibitors: Amidine-Substituted Bis(benzoyl)-[1,3]-diazepan-2-ones and Bis(benzylidene)-bis(gem-dimethyl)Cycloketones, Bioorganic Medicinal Chemistry, 2003, pp. 3379-3392, vol. 11.

Glennon et al; "B-Oxygenated Analogues of the 5-HT2A Serotonin Receptor Agonist 1-(4Bromo-2,5-dimethoxyphenyl)-2-aminopropane", Journal of Medicinal Chemistry, 2004, pp. 6034-6041, vol. 47.

Golub et al, "Molecular Classification of Cancer: Class Discovery and Class Prediction by Gene Expression Monitoring"; Science, 1999, vol. 286, 531-537.

Gronowitz et al; "On the Synthesis of Branched Saturated Fatty Acids"; Lipids, vol. 28, 1993, 889-897.

Knight et al; "Generation and Synthetic Utility of Dianions Derived from Thiophencarboxylic Acids"; J. Chem. Soc., Perkin Trans. 1; 1983; 791-794.

Lala et al; "Role of Nitric Oxide in Tumor Progression: Lessons From Experimental Tumors"; Cancer and Metastasis Reviews (1998), 17, 91-106.

Office Action dated Jun. 7, 2011 for U.S. Appl. No. 12/310,763.

Paine, "A Convenient Synthesis of Nicotinate Esters from 3-cyanopyridones"; J. Heterocyclic; 1987; vol. 24, pp. 351-355.

Patani et al; "Bioisosterism: A Rational Approach in Drug Design"; Chem. Rev. 1996, vol. 96, No. 8, pp. 3147-3176.

Silverman; "The Organic Chemistry of Drug Design and Drug Action"; 2004; Elsevier, pp. 29-32.

Silverman; "The Organic Chemistry of Drug Design and Drug Action"; 2004; Elsevier, pp. 9.

(56) References Cited

OTHER PUBLICATIONS

Tsukerman et al; "Basicity and Structure of .alpha., .beta. -unsaturated Ketones of a Heterocyclic Series. VII. Methyl-substituted Analogs of Chalcones"; Chemical Abstracts Service; XP002467039; STN Databse Accession No.; 1971: 87024.
Zhen et al, "Discovery of Potent 3,5-Diphenyl-1,2,4-oxadiazole Sphingosine-1-phosphate-1 (S1P1) Receptor Agonists with Exceptional Selectivity Against S1P2 and S1P", Journal of Medicinal Chemistry, 2005, pp. 6169-6173, vol. 48, No. 20.
Non-Final Office Action dated Oct. 8, 2010 for U.S. Appl. No. 12/310,763.
Final Office Action dated Dec. 2, 2011 for U.S. Appl. No. 12/310,763.
Final Office Action dated Mar. 1, 2012 for U.S. Appl. No. 12/310,763.
Notice of Allowance dated Jun. 13, 2012 for U.S. Appl. No. 12/310,763.
Non-Final Office Action dated Dec. 2, 2011 for U.S. Appl. No. 12/531,374.
Non-Final Office Action dated Apr. 26, 2012 for U.S. Appl. No. 12/531,374.
Gibson, Editor, Pharmaceutical Preformulation and Formulation, Table of Contents, HIS Health Group, Englewood, CO, USA (2001).
Greene, et al., Protective Groups in Organic Synthesis, $3^{rd}$ Edition, Table of Contents, Wiley, New York (1991).
Kochienski, Protecting Groups, Thieme Stuttgart, Front Book Cover (1994).
Remington, The Science and Practice of Pharmacy, $20^{th}$ Edition, Table of Contents, (2000).
Notice of Allowance dated Nov. 28, 2012 for U.S. Appl. No. 12/920,574.
Abhandlung; "Stickstoffhaltige Derivate der Mkonsaure und ihre Umwandlung in Pyridin"; Journal fur Prkitsche Chemie, vol. 27, pp. 257-294 (1883).
Biyouki, M.A.A., et al., Synthetic Communications, vol. 28, pp. 3817-3825 (1989).
Bode et al; "Immune Regulation, Etc."; Arch. Immunol. Ther. Exp.; 60: 3-12; (2012).
Burstein et al; "Imidazo[1,5-a]pyridine-3-ylidenes-pyridine derived N-heterocyclic carbine ligands", Tetrahedron, vol. 61, pp. 6207-6217; (2004).
Comins et al; "Regiospecific a-Alkylation of 4-Chloro(bromo) pyridine"; J. Org. Chem., vol. 50, pp. 4410-4411, (1985).
Fallahpour, R. A., Synthesis, No. 12, pp. 1665-1667 (2000).
Gura; "Systems for Indentifying New Drugs are Often Faulty"; Cancer Models; Science, vol. 278, No. 5340, pp. 1041-1042; Nov. 1997.
Hu et al; "Sphingosine-1-phosphate, etc."; Mol. Biol. Rep.; 38:4225-4230 (2011).
Inouye et al; "Saccharidew-Dependent Induction of Chiral Helicity in Achiral Synthetic Hydrogen-Bonding Oligomers"; J. Am. Chem. Soc., vol. 126; pp. 2022-2027; (2004).
Jo et al; "Spingosine-1-phosphate, Etc."; Kidney International; 73, 1220-1230; (2008).
Johnson et al; "Relationships Between Drug Acitvity in NCI Preclinical In Vitro and In Vivo Models and Early Clinical Trials"; British Journal of Cancer; 64(10): 1524-1431; (2001).
Kaminski T. et al, J. Org. Chem., vol. 19, pp. 3855-3860 (2003).
Katz, R. B. et al., Syn. Communications, vol. 19, pp. 317-325 (1989).
Matsushita H., et al., J. Org. Chem., vol. 47, pp. 4161-4165 (1982).
Office Action dated Oct. 31, 2012 for U.S. Appl. No. 12/920,656.
Pierrat, P. et al., Synlett., No. 13, pp. 2319-2322 (2004).
Robinson; "Medical Therapy of Inflammatory Bowel Disease for the 21st Century"; Eur. J. Sug. 164, Suppl. 582, pp. 90-98 (1998).
Simeone et al; "Modification of the Pyridine Moiety of Non-peptidyl Indole GnRH Receptor Antagonists"; Bioorganic & Medicinal Chemistry Letters; Volo. 12, pp. 3329-3332; (2002).
Simone; "Oncology: Introduction"; Cecil Textbook of Medicine, 20th Edition; vol. 1; pp. 1004-1010; (1996).
Spiegel et al; "Nature Reviews Immunology"; vol. 11, No. 6; pp. 403-415; Jun. 2011.
Szczepankiewicz et al; "Aminopyridine-based c-Jun N-Terminal Kinase Inhibitors with Cellular Activity and Minimal Cross-Kinase Activity"; J. Med. Chem., vol. 49, pp. 3563-3580; (2006).
Van Der Giet et al; "Relevance and Potential, Etc."; Biol. Chem.; 389, pp. 1381-1390; (2008).
Vermonden et al; "Synthesis of 4-functionalized terdendate pyridine-based ligands"; Tetrahedron, vol. 59, pp. 5039-5045; (2003).
Ziener, U. et al., Chemistry-A European Journal, vol. 6, pp. 4132-4139 (2000).
Notice of Allowance dated Nov. 18, 2011 for U.S. Appl. No. 12/747,280.
Office Action—Final dated Feb. 7, 2013 for U.S. Appl. No. 12/637,918.
Office Action—Restriction dated Apr. 26, 2013 for U.S. Appl. No. 13/383,619.
Office Action—Restriction dated Jul. 24, 2012 for U.S. Appl. No. 12/920,569.
Office Action—Restriction dated May 24, 2012 for U.S. Appl. No. 12/920,656.
Office Action dated Feb. 8, 2013 for U.S. Appl. No. 12/920,656.
Office Action dated Feb. 17, 2012 for U.S. Appl. No. 12/673,918.
Office Action dated Jan. 3, 2013 for U.S. Appl. No. 12/531,374.
Office Action dated Jan. 4, 2013 for U.S. Appl. No. 12/920,569.
Office Action dated Jun. 11, 2012 for U.S. Appl. No. 12/673,918.

* cited by examiner

US 8,580,824 B2

PYRIDIN-4-YL DERIVATIVES AS IMMUNOMODULATING AGENTS

CROSS REFERENCE TO RELATED APPLICATIONS

This application is a United States National Stage Application under 35 U.S.C. 371 of PCT/IB2007/053594 filed on Sep. 6, 2007, which claims the benefit of PCT/IB2006/053147 filed on Sep. 7, 2006.

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies. A further aspect of the invention relates to novel compounds of Formula (II) that serve as intermediates to prepare compounds of Formula (I).

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunomodulating effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunomodulating therapy with a reduced propensity for infections when compared to standard immunosuppressive therapy. Furthermore, the compounds of the present invention can be used in combination with reduced dosages of traditional immunosuppressant therapies, to provide on the one hand effective immunomodulating activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol. Chem.* 265 (1990), 9308-9313; WO 91/15583 published 17 Oct. 1991; WO 99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see in Examples).

The general terms used hereinbefore and hereinafter preferably have, within this disclosure, the following meanings, unless otherwise indicated:

Where the plural form is used for compounds, salts, pharmaceutical compositions, diseases and the like, this is intended to mean also a single compound, salt, or the like.

Any reference hereinbefore or hereinafter to a compound of Formula (I) is to be understood as referring also to salts, especially pharmaceutically acceptable salts, of a compound of Formula (I), as appropriate and expedient.

The term $C_{1-5}$-alkyl, alone or in combination with other groups, means saturated, branched or straight chain groups with one to five carbon atoms. Examples of $C_{1-5}$-alkyl groups are methyl, ethyl, n-propyl, n-butyl, iso-butyl, n-pentyl, 3-pentyl, and iso-pentyl.

The term $C_{1-4}$-alkyl, alone or in combination with other groups, means saturated, branched or preferably straight chain groups with one to four carbon atoms. Examples of $C_{1-4}$-alkyl groups are methyl, ethyl, n-propyl, iso-propyl, n-butyl, and iso-butyl.

The term $C_{1-3}$-alkyl, alone or in combination with other groups, means saturated, branched or preferably straight chain groups with one to three carbon atoms and comprises a methyl, ethyl, n-propyl, and an iso-propyl group; preferred are methyl and ethyl.

The term $C_{2-5}$-alkyl, alone or in combination with other groups, means saturated, branched or preferably straight chain groups with two to five carbon atoms. Examples of $C_{2-5}$-alkyl groups are ethyl, n-propyl, iso-propyl, n-butyl, iso-butyl, n-pentyl, 3-pentyl and iso-pentyl.

The term $C_{2-4}$-alkyl, alone or in combination with other groups, means saturated, branched or preferably straight chain groups with two to four carbon atoms. Examples of $C_{2-4}$-alkyl groups are ethyl, n-propyl, iso-propyl, n-butyl, and iso-butyl.

The term $C_{1-4}$-alkoxy, alone or in combination with other groups, means an R—O group, wherein R is a $C_{1-4}$-alkyl. Examples of $C_{1-4}$-alkoxy groups are ethoxy, propoxy, iso-propoxy, and iso-butoxy.

The term $C_{2-5}$-alkoxy, alone or in combination with other groups, means an R—O group, wherein R is a $C_{2-5}$-alkyl. Examples of $C_{2-5}$-alkoxy groups are ethoxy, propoxy, iso-propoxy, iso-butoxy, and iso-pentoxy.

The term $C_{1-3}$-alkoxy, alone or in combination with other groups, means an R—O group, wherein R is a $C_{1-3}$-alkyl. Examples of $C_{1-3}$-alkoxy groups are methoxy, ethoxy, propoxy, and iso-propoxy.

The term $C_{3-6}$-cycloalkyl, alone or in combination with other groups, means a saturated carbocyclic ring with three to six carbon atoms. Examples of $C_{3-6}$-cycloalkyl groups are cyclopropyl, cyclobutyl, cyclopentyl, and cyclohexyl; preferred is cyclopentyl.

The term halogen means fluoro, chloro, bromo or iodo, preferably fluoro or chloro, most preferably chloro.

Salts are preferably the pharmaceutically acceptable salts of the compounds of Formula (I).

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

The compounds of Formula (I) may contain one or more stereogenic or asymmetric centers, such as one or more asymmetric carbon atoms. Substituents at a double bond or a ring may be present in cis- (=Z—) or trans (=E-) form unless indicated otherwise. The compounds of Formula (I) may thus be present as mixtures of stereoisomers or preferably as pure stereoisomers. Mixtures of stereoisomers may be separated in a manner known to a person skilled in the art.

i) In a first embodiment, the invention relates to pyridine compounds of the Formula (I),

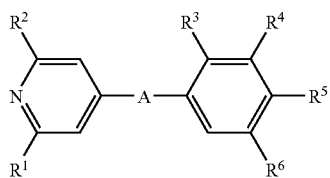

Formula (I)

wherein

A represents *—CONN—$CH_2$—, *—CO—CH=CH—, *—CO—$CH_2CF_{12}$—,

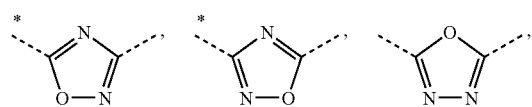

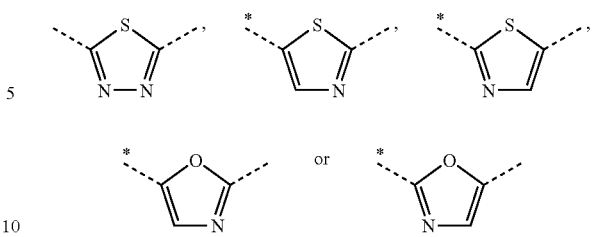

wherein the asterisks indicate the bond that is linked to the pyridine group of Formula (I);

$R^1$ represents $C_{1-4}$-alkyl, or chloro;

$R^2$ represents $C_{1-5}$-alkyl, $C_{1-4}$-alkoxy, or $C_{3-6}$-cycloalkyl;

$R^3$ represents hydrogen, $C_{1-4}$-alkyl, $C_{1-4}$-alkoxy, or halogen;

$R^4$ represents hydrogen, $C_{1-4}$-alkyl, $C_{1-4}$-alkoxy, halogen, trifluoromethyl, or trifluoromethoxy;

$R^5$ represents 2,3-dihydroxypropyl, di-(hydroxy-$C_{1-4}$-alkyl)-$C_{1-4}$-alkyl, —$CH_2$—$(CH_2)_k$—$NHSO_2R^{53}$, —$(CH_2)_n$CH(OH)—$CH_2$—$NHSO_2R^{53}$, —$CH_2$—$(CH_2)_k$—$NHCOR^{54}$, —$(CH_2)_n$CH(OH)—$CH_2$—$NHCOR^{54}$, —$CH_2$—$(CH_2)_n$—$CONR^{51}R^{52}$, —CO—$NHR^{51}$, 1-(3-carboxy-azetidinyl)-2-acetyl, 1-(2-carboxy-pyrrolidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3-propionyl, 1-(3-carboxy-pyrrolidinyl)-3-propionyl, —$(CH_2)_n$CH(OH)—$CH_2$—$NR^{51}R^{52}$, hydroxy, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{51}R^{52}$, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, —$OCH_2$—CH(OH)—$CH_2$—$NR^{51}R^{52}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]propoxy, 2-hydroxy-3-[(pyrrolidine-2-carboxylic acid $C_{1-5}$-alkylester)-1-yl]-propoxy, —$OCH_2$—$(CH_2)_m$—$NHSO_2R^{53}$, —$OCH_2$—CH(OH)—$CH_2$—$NHSO_2R^{53}$, —$OCH_2$—$(CH_2)_m$—$NHCOR^{54}$, —$OCH_2$—CH(OH)—$CH_2$—$NHCOR^{54}$;

$R^{51}$ represents hydrogen, $C_{1-3}$-alkyl, 2-hydroxyethyl, 2-hydroxy-1-hydroxymethyl-ethyl, 2,3-dihydroxypropyl, carboxymethyl, 1-($C_{1-5}$-alkylcarboxy)methyl, 2-carboxyethyl, or 2-($C_{1-5}$-alkylcarboxy)ethyl;

$R^{52}$ represents hydrogen, methyl, or ethyl;

$R^{53}$ represents $C_{1-3}$-alkyl, methylamino, ethylamino, or dimethylamino;

$R^{54}$ represents hydroxymethyl, hydroxyethyl, aminomethyl, methylaminomethyl, dimethylaminomethyl, aminoethyl, 2-methylamino-ethyl, or 2-dimethylamino-ethyl;

k represents the integer 1, 2, or 3;

m represents the integer 1 or 2;

n represents 0, 1, or 2; and $R^6$ represents hydrogen, $C_{1-4}$-alkyl, or halogen.

ii) Another embodiment of the invention relates to pyridine derivatives according to embodiment i), wherein A represents

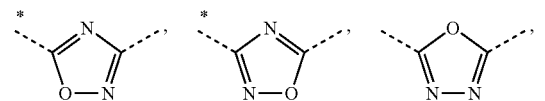

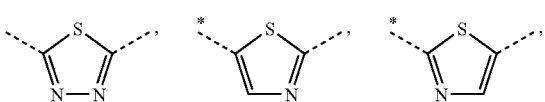

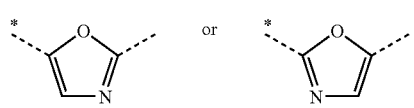

wherein the asterisks indicate the bond that is linked to the pyridine group of Formula (I).

iii) Another embodiment of the invention relates to pyridine derivatives according to embodiment i), wherein A represents

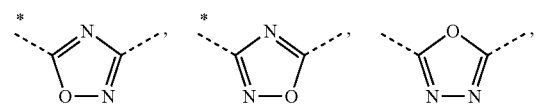

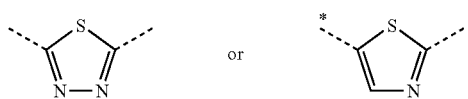

wherein the asterisks indicate the bond that is linked to the pyridine group of Formula (I).

iv) Another embodiment of the invention relates to pyridine derivatives according to embodiment i), wherein A represents

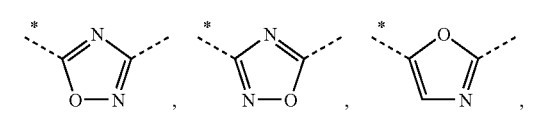

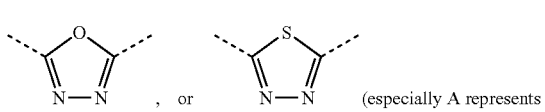 (especially A represents

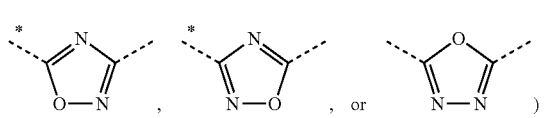 )

wherein the asterisks indicate the bond that is linked to the pyridine group of Formula (I).

v) Another embodiment of the invention relates to pyridine derivatives according to embodiment i), wherein A represents

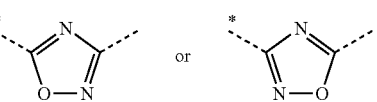

wherein the asterisks indicates the bond that is linked to the pyridine group of Formula (I).

vi) Another embodiment of the invention relates to pyridine derivatives according to embodiment i), wherein A represents

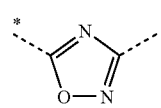

wherein the asterisk indicates the bond that is linked to the pyridine group of Formula (I).

vii) Another embodiment of the invention relates to pyridine derivatives according to embodiment i), wherein A represents

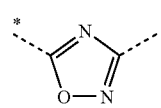

viii) Another embodiment of the invention relates to pyridine derivatives according to any one of the embodiments i) to vii), wherein $R^1$ represents $C_{1-4}$-alkyl.

ix) Another embodiment of the invention relates to pyridine derivatives according to any one of the embodiments i) to vii), wherein $R^1$ represents methyl or ethyl.

x) Another embodiment of the invention relates to pyridine derivatives according to any one of the embodiments i) to vii), wherein $R^1$ represents methyl.

xi) Another embodiment of the invention relates to pyridine derivatives according to any one of the embodiments i) to x), wherein $R^2$ represents $C_{1-5}$-alkyl, $C_{1-3}$-alkoxy, or cyclopentyl.

xii) Another embodiment of the invention relates to pyridine derivatives according to any one of the embodiments i) to x), wherein $R^2$ represents $C_{1-5}$-alkyl.

xiii) Another embodiment of the invention relates to pyridine derivatives according to any one of the embodiments i) to x), wherein $R^2$ represents $C_{2-5}$-alkyl (especially $C_{2-4}$-alkyl).

xiv) Another embodiment of the invention relates to pyridine derivatives according to any one of the embodiments i) to x), wherein $R^2$ represents ethyl, n-propyl, isopropyl, isobutyl, or 3-pentyl (especially ethyl, n-propyl, isopropyl, or isobutyl).

xv) Another embodiment of the invention relates to pyridine derivatives according to any one of the embodiments i) to x), wherein $R^2$ represents n-propyl, or isobutyl.

xvi) Another embodiment of the invention relates to pyridine derivatives according to any one of the embodiments i) to x), wherein $R^2$ represents $C_{1-4}$-alkoxy.

xvii) Another embodiment of the invention relates to pyridine derivatives according to any one of the embodiments i) to x), wherein $R^2$ represents $C_{3-6}$-cycloalkyl.

xviii) Another embodiment of the invention relates to pyridine derivatives according to any one of the embodiments i) to xvii), wherein at least one of $R^3$, $R^4$ and $R^6$ represents a group other than hydrogen.

xix) Another embodiment of the invention relates to pyridine derivatives according to any one of the embodiments i) to xviii), wherein $R^3$ represents methyl or methoxy (especially methoxy), and $R^4$ and $R^6$ represent hydrogen.

xx) Another embodiment of the invention relates to pyridine derivatives according to any one of the embodiments i) to xviii), wherein $R^3$ represents hydrogen.

xxi) Another embodiment of the invention relates to pyridine derivatives according to any one of the embodiments i) to xviii), wherein $R^3$ represents hydrogen; and $R^4$ represents $C_{1-4}$-alkyl, or $C_{1-4}$-alkoxy; and $R^6$ represents $C_{1-4}$-alkyl, or halogen.

xxii) Another embodiment of the invention relates to pyridine derivatives according to any one of the embodiments i) to xviii), wherein $R^3$ represents hydrogen; and $R^4$ represents $C_{1-3}$-alkyl, or methoxy; and $R^6$ represents methyl, ethyl, or chloro.

xxiii) Another embodiment of the invention relates to pyridine derivatives according to any one of the embodiments i) to xviii), wherein $R^3$ represents hydrogen and $R^4$ represents methyl, ethyl, n-propyl, or methoxy (especially methyl, ethyl, or methoxy), and $R^6$ represents methyl, ethyl, or halogen (especially chloro).

xxiv) Another embodiment of the invention relates to pyridine derivatives according to any one of the embodiments i) to xviii), wherein $R^3$ represents hydrogen, and $R^4$ and $R^6$ represent a methyl group.

xxv) Another embodiment of the invention relates to pyridine derivatives according to any one of the embodiments i) to xviii), wherein $R^3$ represents hydrogen, $R^4$ represents a methyl group, and $R^6$ represents an ethyl group.

xxvi) Another embodiment of the invention relates to pyridine derivatives according to any one of the embodiments i) to xviii), wherein $R^3$ represents hydrogen, $R^4$ represents a methoxy group, and $R^6$ represents chloro.

xxvii) Another embodiment of the invention relates to pyridine derivatives according to any one of the embodiments i) to xviii), wherein $R^3$ represents hydrogen, $R^4$ represents a methyl group, and $R^6$ represents chloro.

xxviii) Another embodiment of the invention relates to pyridine derivatives according to any one of the embodiments i) to xxvii), wherein $R^5$ is such that it contains at least one oxygen atom which is directly attached to the phenyl ring of the parent molecule.

xxix) Another embodiment of the invention relates to pyridine derivatives according to any one of the embodiments i) to xxvii), wherein $R^5$ represents 2,3-dihydroxypropyl, di-(hydroxy-$C_{1-4}$-alkyl)-$C_{1-4}$-alkyl, —$CH_2$—$(CH_2)_k$—$NR^{51}R^{52}$, —$CH_2$—$(CH_2)_k$—$NHSO_2R^{53}$, —$(CH_2)_n CH(OH)$—$CH_2$—$NHSO_2R^{53}$, —$CH_2$—$(CH_2)_k$—$NHCOR^{54}$, —$(CH_2)_n CH(OH)$—$CH_2$—$NHCOR^{54}$, —$CH_2$—$(CH_2)_n$—$CONR^{51}R^{52}$, —$CO$—$NHR^{51}$, —$(CH_2)_n CH(OH)$—$CH_2$—$NR^{51}R^{52}$, hydroxy, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{51}R^{52}$, —$OCH_2$—$CH(OH)$—$CH_2$—$NR^{51}R^{52}$, —$OCH_2$—$(CH_2)_m$—$NHSO_2R^{53}$, —$OCH_2$—$CH(OH)$—$CH_2$—$NHSO_2R^{53}$, —$OCH_2$—$(CH_2)_m$—$NHCOR^{54}$, —$OCH_2$—$CH(OH)$—$CH_2$—$NHCOR^{54}$.

xxx) Another embodiment of the invention relates to pyridine derivatives according to any one of the embodiments i) to xxvii), wherein $R^5$ represents 2,3-dihydroxypropyl, —$CH_2$—$(CH_2)_k$—$NR^{51}R^{52}$, —$CH_2$—$(CH_2)_k$—$NHCOR^{54}$, —$(CH_2)_n CH(OH)$—$CH_2$—$NHCOR^{54}$, —$CH_2$—$(CH_2)_n$—$CONR^{51}R^{52}$, —$CO$—$NHR^{51}$, —$(CH_2)_n CH(OH)$—$CH_2$—$NR^{51}R^{52}$, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{51}R^{52}$, —$OCH_2$—$CH(OH)$—$CH_2$—$NR^{51}R^{52}$, —$OCH_2$—$(CH_2)_m$—$NHCOR^{54}$, or —$OCH_2$—$CH(OH)$—$CH_2$—$NHCOR^{54}$ (especially $R^5$ represents 2,3-dihydroxypropyl, —$CH_2$—$(CH_2)_k$—$NR^{51}R^{52}$, —$CH_2$—$(CH_2)_k$—$NHCOR^{54}$, —$(CH_2)_n CH(OH)$—$CH_2$—$NHCOR^{54}$, —$CH_2$—$(CH_2)_n$—$CONR^{51}R^{52}$, —$(CH_2)_n CH(OH)$—$CH_2$—$NR^{51}R^{52}$, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{51}R^{52}$, —$OCH_2$—$CH(OH)$—$CH_2$—$NR^{51}R^{52}$, —$OCH_2$—$(CH_2)_m$—$NHCOR^{54}$, or —$OCH_2$—$CH(OH)$—$CH_2$—$NHCOR^{54}$).

xxxi) Another embodiment of the invention relates to pyridine derivatives according to any one of the embodiments i) to xxvii), wherein $R^5$ represents hydroxy-$C_{2-5}$-alkoxy, di-(hydroxy-$C_{1-4}$-alkyl)-$C_{1-4}$-alkoxy, 2,3-dihydroxy-propoxy, —$OCH_2$—$(CH_2)_m$—$NR^{51}R^{52}$, —$OCH_2$—$CH(OH)$—$CH_2$—$NR^{51}R^{52}$, —$OCH_2$—$(CH_2)_m$—$NHCOR^{54}$, or —$OCH_2$—$CH(OH)$—$CH_2$—$NHCOR^{54}$.

xxxii) Another embodiment of the invention relates to pyridine derivatives according to any one of the embodiments i) to xxvii), wherein $R^5$ represents 3-hydroxy-2-hydroxymethyl-propoxy, 2,3-dihydroxy-propoxy or —$OCH_2 CH(OH)$—$CH_2$—$NHCOR^{54}$ (especially $R^5$ represents 2,3-dihydroxy-propoxy or —$OCH_2$—$CH(OH)$—$CH_2$—$NHCOR^{54}$, wherein $R^{54}$ represents hydroxymethyl).

xxxiii) Another embodiment of the invention relates to pyridine derivatives according to any one of the embodiments i) to xxvii), wherein $R^5$ represents —$OCH_2$—$CH(OH)$—$CH_2$—$NHCOR^{54}$, wherein $R^{54}$ represents hydroxymethyl.

xxxiv) Another embodiment of the invention relates to pyridine derivatives according to any one of the embodiments i) to xxvii), wherein $R^5$ represents 2,3-dihydroxy-propoxy.

xxxv) Another embodiment of the invention relates to pyridine derivatives according to embodiment i), wherein A represents

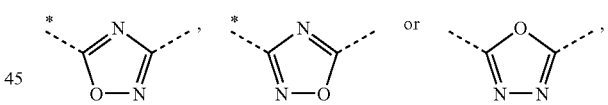

wherein the asterisks indicate the bond that is linked to the pyridine group of Formula (I);

$R^1$ represents methyl, ethyl, or chloro (especially methyl or ethyl);

$R^2$ represents ethyl, n-propyl, isopropyl, isobutyl, 3-pentyl, cyclopentyl, or isopropoxy (especially n-propyl or isobutyl);

$R^3$ represents hydrogen, methyl, or methoxy (especially hydrogen or methoxy);

$R^4$ represents hydrogen, methyl, ethyl, n-propyl, or methoxy (especially hydrogen, methyl, ethyl, or methoxy);

$R^5$ represents 3-hydroxy-2-hydroxymethyl-propoxy, 2,3-dihydroxy-propoxy, or —$OCH_2$—$CH(OH)$—$CH_2$—$NHCOR^{54}$;

$R^{54}$ represents hydroxymethyl, methylaminomethyl, or 2-methylamino-ethyl; and $R^6$ represents hydrogen, methyl, ethyl or chloro;

wherein for the present embodiment the meanings of one or more of the substituents or groups may be replaced by the meaning(s) given for said substituent(s) or group(s) in any one of embodiments v) to vii), ix), x), xiv), xv), xviii), xx), xxiv) to xxvii), and xxxii) to xxxiv).

xxxvi) Another embodiment of the invention relates to pyridine derivatives according to embodiment i), wherein A represents

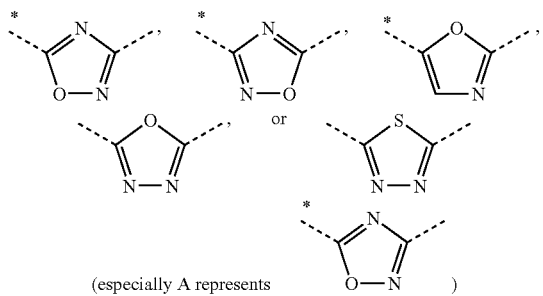

(especially A represents wherein the asterisks indicate the bond that is linked to the pyridine group of Formula (I);
$R^1$ represents $C_{1-4}$-alkyl or chloro;
$R^2$ represents $C_{1-5}$-alkyl $C_{1-4}$-alkoxy, or $C_{3-6}$-alkyl (especially $C_{1-5}$-alkyl or $C_{1-4}$-alkoxy);
$R^3$ represents hydrogen;
$R^4$ represents $C_{1-4}$-alkyl;
$R^5$ represents hydroxy, hydroxy-$C_{2-5}$-alkoxy, di-(hydroxy-$C_{1-4}$-alkyl)-$C_{1-4}$-alkoxy, 2,3-dihydroxy-propoxy, —OCH$_2$—(CH$_2$)$_m$—NR$^{51}$R$^{52}$, —OCH$_2$—CH(OH)—CH$_2$—NR$^{51}$R$^{52}$, or —OCH$_2$—CH(OH)—CH$_2$—NH-COR$^{54}$;
$R^{51}$ represents hydrogen or $C_{1-3}$-alkyl;
$R^{52}$ represents hydrogen or methyl;
$R^{54}$ represents hydroxymethyl or hydroxyethyl;
m represents the integer 1; and
$R^6$ represents $C_{1-4}$-alkyl;
wherein for the present embodiment the meanings of one or more of the substituents or groups may be replaced by the meaning(s) given for said substituent(s) or group(s) in any one of embodiments v) to xvii), xxiv), xxv), and xxxii) to xxxiv).

xxxvii) Examples of pyridine compounds according to Formula (I) are selected from:
N-(3-{4-[5-(2-Chloro-6-methyl-pyridin-4-yl)-[1,2,4]oxadiazol-3-yl]-2,6-dimethyl-phenoxy}-2-hydroxy-propyl)-2-hydroxy-acetamide;
3-{4-[5-(2-Chloro-6-isobutyl-pyridin-4-yl)-[1,2,4]oxadiazol-3-yl]-2,6-dimethyl-phenoxy}-propane-1,2-diol;
N-(3-{4-[5-(2-Chloro-6-isobutyl-pyridin-4-yl)-[1,2,4]oxadiazol-3-yl]-2,6-dimethyl-phenoxy}-2-hydroxy-propyl)-2-hydroxy-acetamide;
3-{4-[5-(2-Ethyl-6-methyl-pyridin-4-yl)-[1,2,4]oxadiazol-3-yl]-2,6-dimethyl-phenoxy}-propane-1,2-diol;
3-{4-[5-(2-Isobutyl-6-methyl-pyridin-4-yl)-[1,2,4]oxadiazol-3-yl]-2,6-dimethyl-phenoxy}-propane-1,2-diol;
2-Hydroxy-N-(2-hydroxy-3-{4-[5-(2-isobutyl-6-methyl-pyridin-4-yl)-[1,2,4]oxadiazol-3-yl]-2,6-dimethyl-phenoxy}-propyl)-acetamide;
3-{2-Ethyl-4-[5-(2-isobutyl-6-methyl-pyridin-4-yl)-[1,2,4]oxadiazol-3-yl]-6-methyl-phenoxy}-propane-1,2-diol;
2-Ethyl-4-[5-(2-isobutyl-6-methyl-pyridin-4-yl)-[1,2,4]oxadiazol-3-yl]-6-methyl-phenol;
(R)-3-{2-Ethyl-4-[5-(2-isobutyl-6-methyl-pyridin-4-yl)-[1,2,4]oxadiazol-3-yl]-6-methyl-phenoxy}-propane-1,2-diol;
(S)-3-{2-Ethyl-4-[5-(2-isobutyl-6-methyl-pyridin-4-yl)-[1,2,4]oxadiazol-3-yl]-6-methyl-phenoxy}-propane-1,2-diol;
2-{2-Ethyl-4-[5-(2-isobutyl-6-methyl-pyridin-4-yl)-[1,2,4]oxadiazol-3-yl]-6-methyl-phenoxymethyl}-propane-1,3-diol;
2-{2-Ethyl-4-[5-(2-isobutyl-6-methyl-pyridin-4-yl)-[1,2,4]oxadiazol-3-yl]-6-methyl-phenoxy}-ethanol;
3-{2-Ethyl-4-[5-(2-isobutyl-6-methyl-pyridin-4-yl)-[1,2,4]oxadiazol-3-yl]-6-methyl-phenoxy}-propan-1-ol;
N-(3-{2-Ethyl-4-[5-(2-isobutyl-6-methyl-pyridin-4-yl)-[1,2,4]oxadiazol-3-yl]-6-methyl-phenoxy}-2-hydroxy-propyl)-2-hydroxy-acetamide;
3-{4-[5-(2,6-Diisobutyl-pyridin-4-yl)-[1,2,4]oxadiazol-3-yl]-2,6-dimethyl-phenoxy}-propane-1,2-diol;
3-{4-[5-(2-Chloro-6-isopropoxy-pyridin-4-yl)-[1,2,4]oxadiazol-3-yl]-2,6-dimethyl-phenoxy}-propane-1,2-diol;
N-(3-{4-[5-(2-Chloro-6-isopropoxy-pyridin-4-yl)-[1,2,4]oxadiazol-3-yl]-2,6-dimethyl-phenoxy}-2-hydroxy-propyl)-2-hydroxy-acetamide;
3-{4-[5-(2-Ethoxy-6-methyl-pyridin-4-yl)-[1,2,4]oxadiazol-3-yl]-2,6-dimethyl-phenoxy}-propane-1,2-diol;
3-{4-[5-(2-Isopropoxy-6-methyl-pyridin-4-yl)-[1,2,4]oxadiazol-3-yl]-2,6-dimethyl-phenoxy}-propane-1,2-diol;
2-Hydroxy-N-(2-hydroxy-3-{4-[5-(2-isopropoxy-6-methyl-pyridin-4-yl)-[1,2,4]oxadiazol-3-yl]-2,6-dimethyl-phenoxy}-propyl)-acetamide;
4-[5-(2-Ethyl-6-methyl-pyridin-4-yl)-[1,2,4]oxadiazol-3-yl]-2,6-dimethyl-phenol;
(R)-3-{4-[5-(2-Ethyl-6-methyl-pyridin-4-yl)-[1,2,4]oxadiazol-3-yl]-2,6-dimethyl-phenoxy}-propane-1,2-diol;
(R)-3-{2-Chloro-4-[5-(2-ethyl-6-methyl-pyridin-4-yl)-[1,2,4]oxadiazol-3-yl]-6-methyl-phenoxy}-propane-1,2-diol;
(S)-3-{4-[5-(2-Ethyl-6-methyl-pyridin-4-yl)-[1,2,4]oxadiazol-3-yl]-2,6-dimethyl-phenoxy}-propane-1,2-diol;
(S)-3-{2-Chloro-4-[5-(2-ethyl-6-methyl-pyridin-4-yl)-[1,2,4]oxadiazol-3-yl]-6-methyl-phenoxy}-propane-1,2-diol;
(S)-3-{2-Chloro-4-[5-(2-ethyl-6-methyl-pyridin-4-yl)-[1,2,4]oxadiazol-3-yl]-6-methoxy-phenoxy}-propane-1,2-diol;
N-(3-{4-[5-(2-Ethyl-6-methyl-pyridin-4-yl)-[1,2,4]oxadiazol-3-yl]-2,6-dimethyl-phenoxy}-2-hydroxy-propyl)-2-hydroxy-acetamide;
N-((R)-3-{2-Ethyl-4-[5-(2-ethyl-6-methyl-pyridin-4-yl)-[1,2,4]oxadiazol-3-yl]-6-methyl-phenoxy}-2-hydroxy-propyl)-2-hydroxy-acetamide;
N-((S)-3-{2-Ethyl-4-[5-(2-ethyl-6-methyl-pyridin-4-yl)-[1,2,4]oxadiazol-3-yl]-6-methyl-phenoxy}-2-hydroxy-propyl)-2-hydroxy-acetamide;
N-(3-{4-[5-(2-Ethyl-6-methyl-pyridin-4-yl)-[1,2,4]oxadiazol-3-yl]-2-methyl-6-propyl-phenoxy}-2-hydroxy-propyl)-2-hydroxy-acetamide;
N-((S)-3-{4-[5-(2-Ethyl-6-methyl-pyridin-4-yl)-[1,2,4]oxadiazol-3-yl]-2-methyl-6-propyl-phenoxy}-2-hydroxy-propyl)-2-hydroxy-acetamide;
N-((R)-3-{2-Chloro-4-[5-(2-ethyl-6-methyl-pyridin-4-yl)-[1,2,4]oxadiazol-3-yl]-6-methyl-phenoxy}-2-hydroxy-propyl)-2-hydroxy-acetamide;
N-((S)-3-{2-Chloro-4-[5-(2-ethyl-6-methyl-pyridin-4-yl)-[1,2,4]oxadiazol-3-yl]-6-methyl-phenoxy}-2-hydroxy-propyl)-2-hydroxy-acetamide;
N-((R)-3-{2-Chloro-4-[5-(2-ethyl-6-methyl-pyridin-4-yl)-[1,2,4]oxadiazol-3-yl]-6-methoxy-phenoxy}-2-hydroxy-propyl)-2-hydroxy-acetamide;
N-((S)-3-{2-Chloro-4-[5-(2-ethyl-6-methyl-pyridin-4-yl)-[1,2,4]oxadiazol-3-yl]-6-methoxy-phenoxy}-2-hydroxy-propyl)-2-hydroxy-acetamide;

N-(3-{4-[5-(2-Ethyl-6-methyl-pyridin-4-yl)-[1,2,4]oxadiazol-3-yl]-2-methoxy-6-methyl-phenoxy}-2-hydroxy-propyl)-2-hydroxy-acetamide;
N-((S)-3-{2-Ethyl-4-[3-(2-ethyl-6-methyl-pyridin-4-yl)-[1,2,4]oxadiazol-5-yl]-6-methyl-phenoxy}-2-hydroxy-propyl)-2-hydroxy-acetamide;
N-((S)-3-{4-[5-(2-Ethyl-6-methyl-pyridin-4-yl)-[1,3,4]oxadiazol-2-yl]-2,6-dimethyl-phenoxy}-2-hydroxy-propyl)-2-hydroxy-acetamide;
2,6-Dimethyl-4-[5-(2-methyl-6-propyl-pyridin-4-yl)-[1,2,4]oxadiazol-3-yl]-phenol;
2-Ethyl-6-methyl-4-[5-(2-methyl-6-propyl-pyridin-4-yl)-[1,2,4]oxadiazol-3-yl]-phenol;
(R)-3-{2,6-Dimethyl-4-[5-(2-methyl-6-propyl-pyridin-4-yl)-[1,2,4]oxadiazol-3-yl]-phenoxy}-propane-1,2-diol;
(S)-3-{2,6-Dimethyl-4-[5-(2-methyl-6-propyl-pyridin-4-yl)-[1,2,4]oxadiazol-3-yl]-phenoxy}-propane-1,2-diol;
(R)-3-{2-Ethyl-6-methyl-4-[5-(2-methyl-6-propyl-pyridin-4-yl)-[1,2,4]oxadiazol-3-yl]-phenoxy}-propane-1,2-diol;
(S)-3-{2-Ethyl-6-methyl-4-[5-(2-methyl-6-propyl-pyridin-4-yl)-[1,2,4]oxadiazol-3-yl]-phenoxy}-propane-1,2-diol;
(R)-3-{2-Chloro-6-methoxy-4-[5-(2-methyl-6-propyl-pyridin-4-yl)-[1,2,4]oxadiazol-3-yl]-phenoxy}-propane-1,2-diol;
(S)-3-{2-Chloro-6-methoxy-4-[5-(2-methyl-6-propyl-pyridin-4-yl)-[1,2,4]oxadiazol-3-yl]-phenoxy}-propane-1,2-diol;
N-(3-{2,6-Dimethyl-4-[5-(2-methyl-6-propyl-pyridin-4-yl)-[1,2,4]oxadiazol-3-yl]-phenoxy}-2-hydroxy-propyl)-2-hydroxy-acetamide;
N-((S)-3-{2,6-Dimethyl-4-[5-(2-methyl-6-propyl-pyridin-4-yl)-[1,2,4]oxadiazol-3-yl]-phenoxy}-2-hydroxy-propyl)-2-hydroxy-acetamide;
N-((R)-3-{2-Ethyl-6-methyl-4-[5-(2-methyl-6-propyl-pyridin-4-yl)-[1,2,4]oxadiazol-3-yl]-phenoxy}-2-hydroxy-propyl)-2-hydroxy-acetamide;
N-((S)-3-{2-Ethyl-6-methyl-4-[5-(2-methyl-6-propyl-pyridin-4-yl)-[1,2,4]oxadiazol-3-yl]-phenoxy}-2-hydroxy-propyl)-2-hydroxy-acetamide;
N-((R)-3-{2-Chloro-6-methoxy-4-[5-(2-methyl-6-propyl-pyridin-4-yl)-[1,2,4]oxadiazol-3-yl]-phenoxy}-2-hydroxy-propyl)-2-hydroxy-acetamide;
N-((S)-3-{2,6-Dimethyl-4-[5-(2-methyl-6-propyl-pyridin-4-yl)-[1,3,4]oxadiazol-2-yl]-phenoxy}-2-hydroxy-propyl)-2-hydroxy-acetamide;
N-((R)-3-{2-Ethyl-6-methyl-4-[5-(2-methyl-6-propyl-pyridin-4-yl)-[1,3,4]oxadiazol-2-yl]-phenoxy}-2-hydroxy-propyl)-2-hydroxy-acetamide;
N-((S)-3-{2-Ethyl-6-methyl-4-[5-(2-methyl-6-propyl-pyridin-4-yl)-[1,3,4]oxadiazol-2-yl]-phenoxy}-2-hydroxy-propyl)-2-hydroxy-acetamide;
2-{2-Ethyl-4-[5-(2-isopropyl-6-methyl-pyridin-4-yl)-[1,2,4]oxadiazol-3-yl]-6-methyl-phenoxy}-ethanol;
(S)-3-{2-Ethyl-4-[5-(2-isopropyl-6-methyl-pyridin-4-yl)-[1,2,4]oxadiazol-3-yl]-6-methyl-phenoxy}-propane-1,2-diol;
N-(3-{2-Ethyl-4-[5-(2-isopropyl-6-methyl-pyridin-4-yl)-[1,2,4]oxadiazol-3-yl]-6-methyl-phenoxy}-2-hydroxy-propyl)-2-hydroxy-acetamide;
2-Hydroxy-N-((S)-2-hydroxy-3-{4-[5-(2-isopropyl-6-methyl-pyridin-4-yl)-[1,2,4]oxadiazol-3-yl]-2-methyl-6-propyl-phenoxy}-propyl)-acetamide;
N-((S)-3-{2-Ethyl-4-[5-(2-isopropyl-6-methyl-pyridin-4-yl)-[1,3,4]thiadiazol-2-yl]-6-methyl-phenoxy}-2-hydroxy-propyl)-2-hydroxy-acetamide;
3-{2-Chloro-4-[5-(2-isobutyl-6-methyl-pyridin-4-yl)-[1,2,4]oxadiazol-3-yl]-6-methyl-phenoxy}-propane-1,2-diol;
3-{2-Chloro-4-[5-(2-isobutyl-6-methyl-pyridin-4-yl)-[1,2,4]oxadiazol-3-yl]-6-methoxy-phenoxy}-propane-1,2-diol;
3-{2-Bromo-4-[5-(2-isobutyl-6-methyl-pyridin-4-yl)-[1,2,4]oxadiazol-3-yl]-phenoxy}-propane-1,2-diol;
1-{2-Chloro-4-[5-(2-isobutyl-6-methyl-pyridin-4-yl)-[1,2,4]oxadiazol-3-yl]-6-methoxy-phenoxy}-3-(2-hydroxy-ethylamino)-propan-2-ol;
2-Hydroxy-N-(2-hydroxy-3-{4-[5-(2-isobutyl-6-methyl-pyridin-4-yl)-[1,2,4]oxadiazol-3-yl]-3-methyl-phenoxy}-propyl)-acetamide;
N-(3-{2-Chloro-4-[5-(2-isobutyl-6-methyl-pyridin-4-yl)-[1,2,4]oxadiazol-3-yl]-6-methyl-phenoxy}-2-hydroxy-propyl)-2-hydroxy-acetamide;
N-(3-{2-Chloro-4-[5-(2-isobutyl-6-methyl-pyridin-4-yl)-[1,2,4]oxadiazol-3-yl]-6-methoxy-phenoxy}-2-hydroxy-propyl)-2-hydroxy-acetamide;
2-Chloro-4-[5-(2-isobutyl-6-methyl-pyridin-4-yl)-[1,2,4]oxadiazol-3-yl]-6-methoxy-phenol;
(S)-3-{4-[5-(2-Isobutyl-6-methyl-pyridin-4-yl)-[1,2,4]oxadiazol-3-yl]-2-methyl-6-propyl-phenoxy}-propane-1,2-diol;
2-Hydroxy-N-(2-hydroxy-3-{4-[5-(2-isobutyl-6-methyl-pyridin-4-yl)-[1,2,4]oxadiazol-3-yl]-3-methoxy-phenoxy}-propyl)-acetamide;
2-Hydroxy-N-((S)-2-hydroxy-3-{4-[5-(2-isobutyl-6-methyl-pyridin-4-yl)-[1,2,4]oxadiazol-3-yl]-2-methyl-6-propyl-phenoxy}-propyl)-acetamide;
2-Hydroxy-N-(2-hydroxy-3-{4-[5-(2-isobutyl-6-methyl-pyridin-4-yl)-[1,2,4]oxadiazol-3-yl]-2-methoxy-6-methyl-phenoxy}-propyl)-acetamide;
N-((R)-3-{2-Chloro-4-[5-(2-isobutyl-6-methyl-pyridin-4-yl)-[1,2,4]oxadiazol-3-yl]-6-methoxy-phenoxy}-2-hydroxy-propyl)-2-hydroxy-acetamide;
N-((S)-3-{2-Chloro-4-[5-(2-isobutyl-6-methyl-pyridin-4-yl)-[1,2,4]oxadiazol-3-yl]-6-methoxy-phenoxy}-2-hydroxy-propyl)-2-hydroxy-acetamide;
(R)-3-{2-Ethyl-4-[3-(2-isobutyl-6-methyl-pyridin-4-yl)-[1,2,4]oxadiazol-5-yl]-6-methyl-phenoxy}-propane-1,2-diol;
(S)-3-{2-Ethyl-4-[3-(2-isobutyl-6-methyl-pyridin-4-yl)-[1,2,4]oxadiazol-5-yl]-6-methyl-phenoxy}-propane-1,2-diol;
2-Hydroxy-N-((R)-2-hydroxy-3-{4-[5-(2-isobutyl-6-methyl-pyridin-4-yl)-[1,3,4]oxadiazol-2-yl]-2,6-dimethyl-phenoxy}-propyl)-acetamide;
2-Hydroxy-N-((S)-2-hydroxy-3-{4-[5-(2-isobutyl-6-methyl-pyridin-4-yl)-[1,3,4]oxadiazol-2-yl]-2,6-dimethyl-phenoxy}-propyl)-acetamide;
N-((R)-3-{2-Ethyl-4-[5-(2-isobutyl-6-methyl-pyridin-4-yl)-[1,3,4]oxadiazol-2-yl]-6-methyl-phenoxy}-2-hydroxy-propyl)-2-hydroxy-acetamide;
N-((S)-3-{2-Ethyl-4-[5-(2-isobutyl-6-methyl-pyridin-4-yl)-[1,3,4]oxadiazol-2-yl]-6-methyl-phenoxy}-2-hydroxy-propyl)-2-hydroxy-acetamide;
N-((S)-3-{2-Chloro-4-[5-(2-isobutyl-6-methyl-pyridin-4-yl)-[1,3,4]oxadiazol-2-yl]-6-methoxy-phenoxy}-2-hydroxy-propyl)-2-hydroxy-acetamide;
N-((S)-3-{2-Ethyl-4-[5-(2-isobutyl-6-methyl-pyridin-4-yl)-[1,3,4]thiadiazol-2-yl]-6-methyl-phenoxy}-2-hydroxy-propyl)-2-hydroxy-acetamide;
2-Ethyl-4-{5-[2-(1-ethyl-propyl)-6-methyl-pyridin-4-yl]-[1,2,4]oxadiazol-3-yl}-6-methyl-phenol;
(R)-3-(2-Ethyl-4-{5-[2-(1-ethyl-propyl)-6-methyl-pyridin-4-yl]-[1,2,4]oxadiazol-3-yl}-6-methyl-phenoxy) -propane-1,2-diol;

(S)-3-(2-Ethyl-4-{5-[2-(1-ethyl-propyl)-6-methyl-pyridin-4-yl]-[1,2,4]oxadiazol-3-yl}-6-methyl-phenoxy)-propane-1,2-diol;
(R)-3-(4-{5-[2-(1-Ethyl-propyl)-6-methyl-pyridin-4-yl]-[1,2,4]oxadiazol-3-yl}-2-methyl-6-propyl-phenoxy)-propane-1,2-diol;
(S)-3-(4-{5-[2-(1-Ethyl-propyl)-6-methyl-pyridin-4-yl]-[1,2,4]oxadiazol-3-yl}-2-methyl-6-propyl-phenoxy)-propane-1,2-diol;
N-[(R)-3-(2-Ethyl-4-{5-[2-(1-ethyl-propyl)-6-methyl-pyridin-4-yl]-[1,2,4]oxadiazol-3-yl}-6-methyl-phenoxy)-2-hydroxy-propyl]-2-hydroxy-acetamide;
N-[(S)-3-(2-Ethyl-4-{5-[2-(1-ethyl-propyl)-6-methyl-pyridin-4-yl]-[1,2,4]oxadiazol-3-yl}-6-methyl-phenoxy)-2-hydroxy-propyl]-2-hydroxy-acetamide;
N-[(R)-3-(4-{5-[2-(1-Ethyl-propyl)-6-methyl-pyridin-4-yl]-[1,2,4]oxadiazol-3-yl}-2-methyl-6-propyl-phenoxy)-2-hydroxy-propyl]-2-hydroxy-acetamide;
N-[(S)-3-(4-{5-[2-(1-Ethyl-propyl)-6-methyl-pyridin-4-yl]-[1,2,4]oxadiazol-3-yl}-2-methyl-6-propyl-phenoxy)-2-hydroxy-propyl]-2-hydroxy-acetamide;
3-{4-[5-(2,6-Diethyl-pyridin-4-yl)-[1,2,4]oxadiazol-3-yl]-2,6-dimethyl-phenoxy}-propane-1,2-diol;
3-{4-[5-(2,6-Diethyl-pyridin-4-yl)-[1,2,4]oxadiazol-3-yl]-2-ethyl-6-methyl-phenoxy}-propane-1,2-diol;
N-((S)-3-{4-[5-(2,6-Diethyl-pyridin-4-yl)-[1,3,4]oxadiazol-2-yl]-2,6-dimethyl-phenoxy}-2-hydroxy-propyl)-2-hydroxy-acetamide;
N-(3-{4-[5-(2-Ethoxy-6-methyl-pyridin-4-yl)-[1,2,4]oxadiazol-3-yl]-2,6-dimethyl-phenoxy}-2-hydroxy-propyl)-2-hydroxy-acetamide;
(R)-3-{2-Ethyl-4-[5-(2-isobutyl-6-methoxy-pyridin-4-yl)-[1,2,4]oxadiazol-3-yl]-6-methyl-phenoxy}-propane-1,2-diol;
(S)-3-{2-Ethyl-4-[5-(2-isobutyl-6-methoxy-pyridin-4-yl)-[1,2,4]oxadiazol-3-yl]-6-methyl-phenoxy}-propane-1,2-diol;
N-((R)-3-{2-Ethyl-4-[5-(2-isobutyl-6-methoxy-pyridin-4-yl)-[1,2,4]oxadiazol-3-yl]-6-methyl-phenoxy}-2-hydroxy-propyl)-2-hydroxy-acetamide;
N-((S)-3-{2-Ethyl-4-[5-(2-isobutyl-6-methoxy-pyridin-4-yl)-[1,2,4]oxadiazol-3-yl]-6-methyl-phenoxy}-2-hydroxy-propyl)-2-hydroxy-acetamide;
(R)-3-{4-[5-(2-Cyclopentyl-6-methyl-pyridin-4-yl)-[1,2,4]oxadiazol-3-yl]-2-ethyl-6-methyl-phenoxy}-propane-1,2-diol;
(S)-3-{4-[5-(2-Cyclopentyl-6-methyl-pyridin-4-yl)-[1,2,4]oxadiazol-3-yl]-2-ethyl-6-methyl-phenoxy}-propane-1,2-diol;
N-((R)-3-{4-[5-(2-Cyclopentyl-6-methyl-pyridin-4-yl)-[1,2,4]oxadiazol-3-yl]-2-ethyl-6-methyl-phenoxy}-2-hydroxy-propyl)-2-hydroxy-acetamide;
N-((S)-3-{4-[5-(2-Cyclopentyl-6-methyl-pyridin-4-yl)-[1,2,4]oxadiazol-3-yl]-2-ethyl-6-methyl-phenoxy}-2-hydroxy-propyl)-2-hydroxy-acetamide; and
(S)-3-{2-Ethyl-4-[5-(2-isobutyl-6-methyl-pyridin-4-yl)-oxazol-2-yl]-6-methyl-phenoxy}-propane-1,2-diol.

xxxviii) in another embodiment examples of pyridine compounds of Formula (I) are selected from:
N-((R)-3-{4-[5-(2-Chloro-6-methyl-pyridin-4-yl)-[1,2,4]oxadiazol-3-yl]-2,6-dimethyl-phenoxy}-2-hydroxy-propyl)-2-hydroxy-acetamide;
N-((S)-3-{4-[5-(2-Chloro-6-methyl-pyridin-4-yl)-[1,2,4]oxadiazol-3-yl]-2,6-dimethyl-phenoxy}-2-hydroxy-propyl)-2-hydroxy-acetamide;
(R)-3-{4-[5-(2-Chloro-6-isobutyl-pyridin-4-yl)-[1,2,4]oxadiazol-3-yl]-2,6-dimethyl-phenoxy}-propane-1,2-diol;
(S)-3-{4-[5-(2-Chloro-6-isobutyl-pyridin-4-yl)-[1,2,4]oxadiazol-3-yl]-2,6-dimethyl-phenoxy}-propane-1,2-diol;
N-((R)-3-{4-[5-(2-Chloro-6-isobutyl-pyridin-4-yl)-[1,2,4]oxadiazol-3-yl]-2,6-dimethyl-phenoxy}-2-hydroxy-propyl)-2-hydroxy-acetamide;
N-((S)-3-{4-[5-(2-Chloro-6-isobutyl-pyridin-4-yl)-[1,2,4]oxadiazol-3-yl]-2,6-dimethyl-phenoxy}-2-hydroxy-propyl)-2-hydroxy-acetamide;
(R)-3-{4-[5-(2-Ethyl-6-methyl-pyridin-4-yl)-[1,2,4]oxadiazol-3-yl]-2,6-dimethyl-phenoxy}-propane-1,2-diol;
(S)-3-{4-[5-(2-Ethyl-6-methyl-pyridin-4-yl)-[1,2,4]oxadiazol-3-yl]-2,6-dimethyl-phenoxy}-propane-1,2-diol;
(R)-3-{4-[5-(2-Isobutyl-6-methyl-pyridin-4-yl)-[1,2,4]oxadiazol-3-yl]-2,6-dimethyl-phenoxy}-propane-1,2-diol;
(S)-3-{4-[5-(2-isobutyl-6-methyl-pyridin-4-yl)-[1,2,4]oxadiazol-3-yl]-2,6-dimethyl-phenoxy}-propane-1,2-diol;
2-Hydroxy-N-((R)-2-hydroxy-3-{4-[5-(2-isobutyl-6-methyl-pyridin-4-yl)-[1,2,4]oxadiazol-3-yl]-2,6-dimethyl-phenoxy}-propyl)-acetamide;
2-Hydroxy-N-((S)-2-hydroxy-3-{4-[5-(2-isobutyl-6-methyl-pyridin-4-yl)-[1,2,4]oxadiazol-3-yl]-2,6-dimethyl-phenoxy}-propyl)-acetamide;
(R)-3-{2-Ethyl-4-[5-(2-isobutyl-6-methyl-pyridin-4-yl)-[1,2,4]oxadiazol-3-yl]-6-methyl-phenoxy}-propane-1,2-diol;
(S)-3-{2-Ethyl-4-[5-(2-isobutyl-6-methyl-pyridin-4-yl)-[1,2,4]oxadiazol-3-yl]-6-methyl-phenoxy}-propane-1,2-diol;
2-Ethyl-4-[5-(2-isobutyl-6-methyl-pyridin-4-yl)-[1,2,4]oxadiazol-3-yl]-6-methyl-phenol;
(R)-3-{2-Ethyl-4-[5-(2-isobutyl-6-methyl-pyridin-4-yl)-[1,2,4]oxadiazol-3-yl]-6-methyl-phenoxy}-propane-1,2-diol;
(S)-3-{2-Ethyl-4-[5-(2-isobutyl-6-methyl-pyridin-4-yl)-[1,2,4]oxadiazol-3-yl]-6-methyl-phenoxy}-propane-1,2-diol;
2-{2-Ethyl-4-[5-(2-isobutyl-6-methyl-pyridin-4-yl)-[1,2,4]oxadiazol-3-yl]-6-methyl-phenoxymethyl}-propane-1,3-diol;
2-{2-Ethyl-4-[5-(2-isobutyl-6-methyl-pyridin-4-yl)-[1,2,4]oxadiazol-3-yl]-6-methyl-phenoxy}-ethanol;
3-{2-Ethyl-4-[5-(2-isobutyl-6-methyl-pyridin-4-yl)-[1,2,4]oxadiazol-3-yl]-6-methyl-phenoxy}-propan-1-ol;
N-((R)-3-{2-Ethyl-4-[5-(2-isobutyl-6-methyl-pyridin-4-yl)-[1,2,4]oxadiazol-3-yl]-6-methyl-phenoxy}-2-hydroxy-propyl)-2-hydroxy-acetamide;
N-((S)-3-{2-Ethyl-4-[5-(2-isobutyl-6-methyl-pyridin-4-yl)-[1,2,4]oxadiazol-3-yl]-6-methyl-phenoxy}-2-hydroxy-propyl)-2-hydroxy-acetamide;
(R)-3-{4-[5-(2,6-Diisobutyl-pyridin-4-yl)-[1,2,4]oxadiazol-3-yl]-2,6-dimethyl-phenoxy}-propane-1,2-diol;
(S)-3-{4-[5-(2,6-Diisobutyl-pyridin-4-yl)-[1,2,4]oxadiazol-3-yl]-2,6-dimethyl-phenoxy}-propane-1,2-diol;
(R)-3-{4-[5-(2-Chloro-6-isopropoxy-pyridin-4-yl)-[1,2,4]oxadiazol-3-yl]-2,6-dimethyl-phenoxy}-propane-1,2-diol;
(S)-3-{4-[5-(2-Chloro-6-isopropoxy-pyridin-4-yl)-[1,2,4]oxadiazol-3-yl]-2,6-dimethyl-phenoxy}-propane-1,2-diol;
N-((R)-3-{4-[5-(2-Chloro-6-isopropoxy-pyridin-4-yl)-[1,2,4]oxadiazol-3-yl]-2,6-dimethyl-phenoxy}-2-hydroxy-propyl)-2-hydroxy-acetamide;
N-((S)-3-{4-[5-(2-Chloro-6-isopropoxy-pyridin-4-yl)-[1,2,4]oxadiazol-3-yl]-2,6-dimethyl-phenoxy}-2-hydroxy-propyl)-2-hydroxy-acetamide;
(R)-3-{4-[5-(2-Ethoxy-6-methyl-pyridin-4-yl)-[1,2,4]oxadiazol-3-yl]-2,6-dimethyl-phenoxy}-propane-1,2-diol;

(S)-3-{4-[5-(2-Ethoxy-6-methyl-pyridin-4-yl)-[1,2,4]oxadiazol-3-yl]-2,6-dimethyl-phenoxy}-propane-1,2-diol;

(R)-3-{4-[5-(2-Isopropoxy-6-methyl-pyridin-4-yl)-[1,2,4]oxadiazol-3-yl]-2,6-dimethyl-phenoxy}-propane-1,2-diol;

(S)-3-{4-[5-(2-Isopropoxy-6-methyl-pyridin-4-yl)-[1,2,4]oxadiazol-3-yl]-2,6-dimethyl-phenoxy}-propane-1,2-diol;

2-Hydroxy-N-((R)-2-hydroxy-3-{4-[5-(2-isopropoxy-6-methyl-pyridin-4-yl)-[1,2,4]oxadiazol-3-yl]-2,6-dimethyl-phenoxy}-propyl)-acetamide;

2-Hydroxy-N-((S)-2-hydroxy-3-{4-[5-(2-isopropoxy-6-methyl-pyridin-4-yl)-[1,2,4]oxadiazol-3-yl]-2,6-dimethyl-phenoxy}-propyl)-acetamide;

4-[5-(2-Ethyl-6-methyl-pyridin-4-yl)-[1,2,4]oxadiazol-3-yl]-2,6-dimethyl-phenol;

(R)-3-{4-[5-(2-Ethyl-6-methyl-pyridin-4-yl)-[1,2,4]oxadiazol-3-yl]-2,6-dimethyl-phenoxy}-propane-1,2-diol;

(R)-3-{2-Chloro-4-[5-(2-ethyl-6-methyl-pyridin-4-yl)-[1,2,4]oxadiazol-3-yl]-6-methyl-phenoxy}-propane-1,2-diol;

(S)-3-{4-[5-(2-Ethyl-6-methyl-pyridin-4-yl)-[1,2,4]oxadiazol-3-yl]-2,6-dimethyl-phenoxy}-propane-1,2-diol;

(S)-3-{2-Chloro-4-[5-(2-ethyl-6-methyl-pyridin-4-yl)-[1,2,4]oxadiazol-3-yl]-6-methyl-phenoxy}-propane-1,2-diol;

(S)-3-{2-Chloro-4-[5-(2-ethyl-6-methyl-pyridin-4-yl)-[1,2,4]oxadiazol-3-yl]-6-methoxy-phenoxy}-propane-1,2-diol;

N-((R)-3-{4-[5-(2-Ethyl-6-methyl-pyridin-4-yl)-[1,2,4]oxadiazol-3-yl]-2,6-dimethyl-phenoxy}-2-hydroxy-propyl)-2-hydroxy-acetamide;

N-((S)-3-{4-[5-(2-Ethyl-6-methyl-pyridin-4-yl)-[1,2,4]oxadiazol-3-yl]-2,6-dimethyl-phenoxy}-2-hydroxy-propyl)-2-hydroxy-acetamide;

N-((R)-3-{2-Ethyl-4-[5-(2-ethyl-6-methyl-pyridin-4-yl)-[1,2,4]oxadiazol-3-yl]-6-methyl-phenoxy}-2-hydroxy-propyl)-2-hydroxy-acetamide;

N-((S)-3-{2-Ethyl-4-[5-(2-ethyl-6-methyl-pyridin-4-yl)-[1,2,4]oxadiazol-3-yl]-6-methyl-phenoxy}-2-hydroxy-propyl)-2-hydroxy-acetamide;

N-((R)-3-{4-[5-(2-Ethyl-6-methyl-pyridin-4-yl)-[1,2,4]oxadiazol-3-yl]-2-methyl-6-propyl-phenoxy}-2-hydroxy-propyl)-2-hydroxy-acetamide;

N-((S)-3-{4-[5-(2-Ethyl-6-methyl-pyridin-4-yl)-[1,2,4]oxadiazol-3-yl]-2-methyl-6-propyl-phenoxy}-2-hydroxy-propyl)-2-hydroxy-acetamide;

N-((S)-3-{4-[5-(2-Ethyl-6-methyl-pyridin-4-yl)-[1,2,4]oxadiazol-3-yl]-2-methyl-6-propyl-phenoxy}-2-hydroxy-propyl)-2-hydroxy-acetamide;

N-((R)-3-{2-Chloro-4-[5-(2-ethyl-6-methyl-pyridin-4-yl)-[1,2,4]oxadiazol-3-yl]-6-methyl-phenoxy}-2-hydroxy-propyl)-2-hydroxy-acetamide;

N-((S)-3-{2-Chloro-4-[5-(2-ethyl-6-methyl-pyridin-4-yl)-[1,2,4]oxadiazol-3-yl]-6-methyl-phenoxy}-2-hydroxy-propyl)-2-hydroxy-acetamide;

N-((R)-3-{2-Chloro-4-[5-(2-ethyl-6-methyl-pyridin-4-yl)-[1,2,4]oxadiazol-3-yl]-6-methoxy-phenoxy}-2-hydroxy-propyl)-2-hydroxy-acetamide;

N-((S)-3-{2-Chloro-4-[5-(2-ethyl-6-methyl-pyridin-4-yl)-[1,2,4]oxadiazol-3-yl]-6-methoxy-phenoxy}-2-hydroxy-propyl)-2-hydroxy-acetamide;

N-((R)-3-{4-[5-(2-Ethyl-6-methyl-pyridin-4-yl)-[1,2,4]oxadiazol-3-yl]-2-methoxy-6-methyl-phenoxy}-2-hydroxy-propyl)-2-hydroxy-acetamide;

N-((S)-3-{4-[5-(2-Ethyl-6-methyl-pyridin-4-yl)-[1,2,4]oxadiazol-3-yl]-2-methoxy-6-methyl-phenoxy}-2-hydroxy-propyl)-2-hydroxy-acetamide;

N-((S)-3-{2-Ethyl-4-[3-(2-ethyl-6-methyl-pyridin-4-yl)-[1,2,4]oxadiazol-5-yl]-6-methyl-phenoxy}-2-hydroxy-propyl)-2-hydroxy-acetamide;

N-((S)-3-{4-[5-(2-Ethyl-6-methyl-pyridin-4-yl)-[1,3,4]oxadiazol-2-yl]-2,6-dimethyl-phenoxy}-2-hydroxy-propyl)-2-hydroxy-acetamide;

2,6-Dimethyl-4-[5-(2-methyl-6-propyl-pyridin-4-yl)-[1,2,4]oxadiazol-3-yl]-phenol;

2-Ethyl-6-methyl-4-[5-(2-methyl-6-propyl-pyridin-4-yl)-[1,2,4]oxadiazol-3-yl]-phenol;

(R)-3-{2,6-Dimethyl-4-[5-(2-methyl-6-propyl-pyridin-4-yl)-[1,2,4]oxadiazol-3-yl]-phenoxy}-propane-1,2-diol;

(S)-3-{2,6-Dimethyl-4-[5-(2-methyl-6-propyl-pyridin-4-yl)-[1,2,4]oxadiazol-3-yl]-phenoxy}-propane-1,2-diol;

(R)-3-{2-Ethyl-6-methyl-4-[5-(2-methyl-6-propyl-pyridin-4-yl)-[1,2,4]oxadiazol-3-yl]-phenoxy}-propane-1,2-diol;

(S)-3-{2-Ethyl-6-methyl-4-[5-(2-methyl-6-propyl-pyridin-4-yl)-[1,2,4]oxadiazol-3-yl]-phenoxy}-propane-1,2-diol;

(R)-3-{2-Chloro-6-methoxy-4-[5-(2-methyl-6-propyl-pyridin-4-yl)-[1,2,4]oxadiazol-3-yl]-phenoxy}-propane-1,2-diol;

(S)-3-{2-Chloro-6-methoxy-4-[5-(2-methyl-6-propyl-pyridin-4-yl)-[1,2,4]oxadiazol-3-yl]-phenoxy}-propane-1,2-diol;

N-((R)-3-{2,6-Dimethyl-4-[5-(2-methyl-6-propyl-pyridin-4-yl)-[1,2,4]oxadiazol-3-yl]-phenoxy}-2-hydroxy-propyl)-2-hydroxy-acetamide;

N-((S)-3-{2,6-Dimethyl-4-[5-(2-methyl-6-propyl-pyridin-4-yl)-[1,2,4]oxadiazol-3-yl]-phenoxy}-2-hydroxy-propyl)-2-hydroxy-acetamide;

N-((S)-3-{2,6-Dimethyl-4-[5-(2-methyl-6-propyl-pyridin-4-yl)-[1,2,4]oxadiazol-3-yl]-phenoxy}-2-hydroxy-propyl)-2-hydroxy-acetamide;

N-((R)-3-{2-Ethyl-6-methyl-4-[5-(2-methyl-6-propyl-pyridin-4-yl)-[1,2,4]oxa diazol-3-yl]-phenoxy}-2-hydroxy-propyl)-2-hydroxy-acetamide;

N-((S)-3-{2-Ethyl-6-methyl-4-[5-(2-methyl-6-propyl-pyridin-4-yl)-[1,2,4]oxadiazol-3-yl]-phenoxy}-2-hydroxy-propyl)-2-hydroxy-acetamide;

N-((R)-3-{2-Chloro-6-methoxy-4-[5-(2-methyl-6-propyl-pyridin-4-yl)-[1,2,4]oxadiazol-3-yl]-phenoxy}-2-hydroxy-propyl)-2-hydroxy-acetamide;

N-((S)-3-{2,6-Dimethyl-4-[5-(2-methyl-6-propyl-pyridin-4-yl)-[1,3,4]oxadiazol-2-yl]-phenoxy}-2-hydroxy-propyl)-2-hydroxy-acetamide;

N-((R)-3-{2-Ethyl-6-methyl-4-[5-(2-methyl-6-propyl-pyridin-4-yl)-[1,3,4]oxadiazol-2-yl]-phenoxy}-2-hydroxy-propyl)-2-hydroxy-acetamide;

N-((S)-3-{2-Ethyl-6-methyl-4-[5-(2-methyl-6-propyl-pyridin-4-yl)-[1,3,4]oxadiazol-2-yl]-phenoxy}-2-hydroxy-propyl)-2-hydroxy-acetamide;

2-{2-Ethyl-4-[5-(2-isopropyl-6-methyl-pyridin-4-yl)-[1,2,4]oxadiazol-3-yl]-6-methyl-phenoxy}-ethanol;

(S)-3-{2-Ethyl-4-[5-(2-isopropyl-6-methyl-pyridin-4-yl)-[1,2,4]oxadiazol-3-yl]-6-methyl-phenoxy}-propane-1,2-diol;

N-((R)-3-{2-Ethyl-4-[5-(2-isopropyl-6-methyl-pyridin-4-yl)-[1,2,4]oxadiazol-3-yl]-6-methyl-phenoxy}-2-hydroxy-propyl)-2-hydroxy-acetamide;

N-((S)-3-{2-Ethyl-4-[5-(2-isopropyl-6-methyl-pyridin-4-yl)-[1,2,4]oxadiazol-3-yl]-6-methyl-phenoxy}-2-hydroxy-propyl)-2-hydroxy-acetamide;

2-Hydroxy-N-((S)-2-hydroxy-3-{4-[5-(2-isopropyl-6-methyl-pyridin-4-yl)-[1,2,4]oxadiazol-3-yl]-2-methyl-6-propyl-phenoxy}-propyl)-acetamide;

N-((S)-3-{2-Ethyl-4-[5-(2-isopropyl-6-methyl-pyridin-4-yl)-[1,3,4]thiadiazol-2-yl]-6-methyl-phenoxy}-2-hydroxy-propyl)-2-hydroxy-acetamide;
(R)-3-{2-Chloro-4-[5-(2-isobutyl-6-methyl-pyridin-4-yl)-[1,2,4]oxadiazol-3-yl]-6-methyl-phenoxy}-propane-1,2-diol;
(S)-3-{2-Chloro-4-[5-(2-isobutyl-6-methyl-pyridin-4-yl)-[1,2,4]oxadiazol-3-yl]-6-methyl-phenoxy}-propane-1,2-diol;
(R)-3-{2-Chloro-4-[5-(2-isobutyl-6-methyl-pyridin-4-yl)-[1,2,4]oxadiazol-3-yl]-6-methoxy-phenoxy}-propane-1,2-diol;
(S)-3-{2-Chloro-4-[5-(2-isobutyl-6-methyl-pyridin-4-yl)-[1,2,4]oxadiazol-3-yl]-6-methoxy-phenoxy}-propane-1,2-diol;
(R)-3-{2-Bromo-4-[5-(2-isobutyl-6-methyl-pyridin-4-yl)-[1,2,4]oxadiazol-3-yl]-phenoxy}-propane-1,2-diol;
(S)-3-{2-Bromo-4-[5-(2-isobutyl-6-methyl-pyridin-4-yl)-[1,2,4]oxadiazol-3-yl]-phenoxy}-propane-1,2-diol;
(R)-1-{2-Chloro-4-[5-(2-isobutyl-6-methyl-pyridin-4-yl)-[1,2,4]oxadiazol-3-yl]-6-methoxy-phenoxy}-3-(2-hydroxy-ethylamino)-propan-2-ol;
(S)-1-{2-Chloro-4-[5-(2-isobutyl-6-methyl-pyridin-4-yl)-[1,2,4]oxadiazol-3-yl]-6-methoxy-phenoxy}-3-(2-hydroxy-ethylamino)-propan-2-ol;
2-Hydroxy-N-((R)-2-hydroxy-3-{4-[5-(2-isobutyl-6-methyl-pyridin-4-yl)-[1,2,4]oxadiazol-3-yl]-3-methyl-phenoxy}-propyl)-acetamide;
2-Hydroxy-N-((S)-2-hydroxy-3-{4-[5-(2-isobutyl-6-methyl-pyridin-4-yl)-[1,2,4]oxadiazol-3-yl]-3-methyl-phenoxy}-propyl)-acetamide;
N-((R)-3-{2-Chloro-4-[5-(2-isobutyl-6-methyl-pyridin-4-yl)-[1,2,4]oxadiazol-3-yl]-6-methyl-phenoxy}-2-hydroxy-propyl)-2-hydroxy-acetamide;
N-((S)-3-{2-Chloro-4-[5-(2-isobutyl-6-methyl-pyridin-4-yl)-[1,2,4]oxadiazol-3-yl]-6-methyl-phenoxy}-2-hydroxy-propyl)-2-hydroxy-acetamide;
N-((R)-3-{2-Chloro-4-[5-(2-isobutyl-6-methyl-pyridin-4-yl)-[1,2,4]oxadiazol-3-yl]-6-methoxy-phenoxy}-2-hydroxy-propyl)-2-hydroxy-acetamide;
N-((S)-3-{2-Chloro-4-[5-(2-isobutyl-6-methyl-pyridin-4-yl)-[1,2,4]oxadiazol-3-yl]-6-methoxy-phenoxy}-2-hydroxy-propyl)-2-hydroxy-acetamide;
2-Chloro-4-[5-(2-isobutyl-6-methyl-pyridin-4-yl)-[1,2,4]oxadiazol-3-yl]-6-methoxy-phenol;
(S)-3-{4-[5-(2-Isobutyl-6-methyl-pyridin-4-yl)-[1,2,4]oxadiazol-3-yl]-2-methyl-6-propyl-phenoxy}-propane-1,2-diol;
2-Hydroxy-N-((R)-2-hydroxy-3-{4-[5-(2-isobutyl-6-methyl-pyridin-4-yl)-[1,2,4]oxadiazol-3-yl]-3-methoxy-phenoxy}-propyl)-acetamide;
2-Hydroxy-N-((S)-2-hydroxy-3-{4-[5-(2-isobutyl-6-methyl-pyridin-4-yl)-[1,2,4]oxadiazol-3-yl]-3-methoxy-phenoxy}-propyl)acetamide;
2-Hydroxy-N-((S)-2-hydroxy-3-{4-[5-(2-isobutyl-6-methyl-pyridin-4-yl)-[1,2,4]oxadiazol-3-yl]-2-methyl-6-propyl-phenoxy}-propyl)-acetamide;
2-Hydroxy-N-((R)-2-hydroxy-3-{4-[5-(2-isobutyl-6-methyl-pyridin-4-yl)-[1,2,4]oxadiazol-3-yl]-2-methoxy-6-methyl-phenoxy}-propyl)-acetamide;
2-Hydroxy-N-((S)-2-hydroxy-3-{4-[5-(2-isobutyl-6-methyl-pyridin-4-yl)-[1,2,4]oxadiazol-3-yl]-2-methoxy-6-methyl-phenoxy}-propyl)-acetamide;
N-((R)-3-{2-Chloro-4-[5-(2-isobutyl-6-methyl-pyridin-4-yl)-[1,2,4]oxadiazol-3-yl]-6-methoxy-phenoxy}-2-hydroxy-propyl)-2-hydroxy-acetamide;
N-((S)-3-{2-Chloro-4-[5-(2-isobutyl-6-methyl-pyridin-4-yl)-[1,2,4]oxadiazol-3-yl]-6-methoxy-phenoxy}-2-hydroxy-propyl)-2-hydroxy-acetamide;
(R)-3-{2-Ethyl-4-[3-(2-isobutyl-6-methyl-pyridin-4-yl)-[1,2,4]oxadiazol-5-yl]-6-methyl-phenoxy}-propane-1,2-diol;
(S)-3-{2-Ethyl-4-[3-(2-isobutyl-6-methyl-pyridin-4-yl)-[1,2,4]oxadiazol-5-yl]-6-methyl-phenoxy}-propane-1,2-diol;
2-Hydroxy-N-((R)-2-hydroxy-3-{4-[5-(2-isobutyl-6-methyl-pyridin-4-yl)-[1,3,4]oxadiazol-2-yl]-2,6-dimethyl-phenoxy}-propyl)-acetamide;
2-Hydroxy-N-((S)-2-hydroxy-3-{4-[5-(2-isobutyl-6-methyl-pyridin-4-yl)-[1,3,4]oxadiazol-2-yl]-2,6-dimethyl-phenoxy}-propyl)-acetamide;
N-((R)-3-{2-Ethyl-4-[5-(2-isobutyl-6-methyl-pyridin-4-yl)-[1,3,4]oxadiazol-2-yl]-6-methyl-phenoxy}-2-hydroxy-propyl)-2-hydroxy-acetamide;
N-((S)-3-{2-Ethyl-4-[5-(2-isobutyl-6-methyl-pyridin-4-yl)-[1,3,4]oxadiazol-2-yl]-6-methyl-phenoxy}-2-hydroxy-propyl)-2-hydroxy-acetamide;
N-((S)-3-{2-Chloro-4-[5-(2-isobutyl-6-methyl-pyridin-4-yl)-[1,3,4]oxadiazol-2-yl]-6-methoxy-phenoxy}-2-hydroxy-propyl)-2-hydroxy-acetamide;
N-((S)-3-{2-Ethyl-4-[5-(2-isobutyl-6-methyl-pyridin-4-yl)-[1,3,4]thiadiazol-2-yl]-6-methyl-phenoxy}-2-hydroxy-propyl)-2-hydroxy-acetamide;
2-Ethyl-4-{5-[2-(1-ethyl-propyl)-6-methyl-pyridin-4-yl]-[1,2,4]oxadiazol-3-yl}-6-methyl-phenol;
(R)-3-(2-Ethyl-4-{5-[2-(1-ethyl-propyl)-6-methyl-pyridin-4-yl]-[1,2,4]oxadiazol-3-yl}-6-methyl-phenoxy)-propane-1,2-diol;
(S)-3-(2-Ethyl-4-{5-[2-(1-ethyl-propyl)-6-methyl-pyridin-4-yl]-[1,2,4]oxadiazol-3-yl}-6-methyl-phenoxy)-propane-1,2-diol;
(R)-3-(4-{5-[2-(1-Ethyl-propyl)-6-methyl-pyridin-4-yl]-[1,2,4]oxadiazol-3-yl}-2-methyl-6-propyl-phenoxy)-propane-1,2-diol;
(S)-3-(4-{5-[2-(1-Ethyl-propyl)-6-methyl-pyridin-4-yl]-[1,2,4]oxadiazol-3-yl}-2-methyl-6-propyl-phenoxy)-propane-1,2-diol;
N-[(R)-3-(2-Ethyl-4-{5-[2-(1-ethyl-propyl)-6-methyl-pyridin-4-yl]-[1,2,4]oxadiazol-3-yl}-6-methyl-phenoxy)-2-hydroxy-propyl]-2-hydroxy-acetamide;
N-[(S)-3-(2-Ethyl-4-{5-[2-(1-ethyl-propyl)-6-methyl-pyridin-4-yl]-[1,2,4]oxadiazol-3-yl}-6-methyl-phenoxy)-2-hydroxy-propyl]-2-hydroxy-acetamide;
N-[(R)-3-(4-{5-[2-(1-Ethyl-propyl)-6-methyl-pyridin-4-yl]-[1,2,4]oxadiazol-3-yl}-2-methyl-6-propyl-phenoxy)-2-hydroxy-propyl]-2-hydroxy-acetamide;
N-[(S)-3-(4-{5-[2-(1-Ethyl-propyl)-6-methyl-pyridin-4-yl]-[1,2,4]oxadiazol-3-yl}-2-methyl-6-propyl-phenoxy)-2-hydroxy-propyl]-2-hydroxy-acetamide;
(R)-3-{4-[5-(2,6-Diethyl-pyridin-4-yl)-[1,2,4]oxadiazol-3-yl]-2,6-dimethyl-phenoxy}-propane-1,2-diol;
(S)-3-{4-[5-(2,6-Diethyl-pyridin-4-yl)-[1,2,4]oxadiazol-3-yl]-2,6-dimethyl-phenoxy}-propane-1,2-diol;
(R)-3-{4-[5-(2,6-Diethyl-pyridin-4-yl)-[1,2,4]oxadiazol-3-yl]-2-ethyl-6-methyl-phenoxy}-propane-1,2-diol;
(S)-3-{4-[5-(2,6-Diethyl-pyridin-4-yl)-[1,2,4]oxadiazol-3-yl]-2-ethyl-6-methyl-phenoxy}-propane-1,2-diol;
N-((S)-3-{4-[5-(2,6-Diethyl-pyridin-4-yl)-[1,3,4]oxadiazol-2-yl]-2,6-dimethyl-phenoxy}-2-hydroxy-propyl)-2-hydroxy-acetamide;
N-((R)-3-{4-[5-(2-Ethoxy-6-methyl-pyridin-4-yl)-[1,2,4]oxadiazol-3-yl]-2,6-dimethyl-phenoxy}-2-hydroxy-propyl)-2-hydroxy-acetamide;

N-((S)-3-{4-[5-(2-Ethoxy-6-methyl-pyridin-4-yl)-[1,2,4] oxadiazol-3-yl]-2,6-dimethyl-phenoxy}-2-hydroxy-propyl)-2-hydroxy-acetamide;

(R)-3-{2-Ethyl-4-[5-(2-isobutyl-6-methoxy-pyridin-4-yl)-[1,2,4]oxadiazol-3-yl]-6-methyl-phenoxy}-propane-1,2-diol;

(S)-3-{2-Ethyl-4-[5-(2-isobutyl-6-methoxy-pyridin-4-yl)-[1,2,4]oxadiazol-3-yl]-6-methyl-phenoxy}-propane-1,2-diol;

N-((R)-3-{2-Ethyl-4-[5-(2-isobutyl-6-methoxy-pyridin-4-yl)-[1,2,4]oxadiazol-3-yl]-6-methyl-phenoxy}-2-hydroxy-propyl)-2-hydroxy-acetamide;

N-((S)-3-{2-Ethyl-4-[5-(2-isobutyl-6-methoxy-pyridin-4-yl)-[1,2,4]oxadiazol-3-yl]-6-methyl-phenoxy}-2-hydroxy-propyl)-2-hydroxy-acetamide;

(R)-3-{4-[5-(2-Cyclopentyl-6-methyl-pyridin-4-yl)-[1,2,4] oxadiazol-3-yl]-2-ethyl-6-methyl-phenoxy}-propane-1,2-diol;

(S)-3-{4-[5-(2-Cyclopentyl-6-methyl-pyridin-4-yl)-[1,2,4] oxadiazol-3-yl]-2-ethyl-6-methyl-phenoxy}-propane-1,2-diol;

N-((R)-3-{4-[5-(2-Cyclopentyl-6-methyl-pyridin-4-yl)-[1,2,4]oxadiazol-3-yl]-2-ethyl-6-methyl-phenoxy}-2-hydroxy-propyl)-2-hydroxy-acetamide;

N-((S)-3-{4-[5-(2-Cyclopentyl-6-methyl-pyridin-4-yl)-[1,2,4]oxadiazol-3-yl]-2-ethyl-6-methyl-phenoxy}-2-hydroxy-propyl)-2-hydroxy-acetamide; and (S)-3-{2-Ethyl-4-[5-(2-isobutyl-6-methyl-pyridin-4-yl)-oxazol-2-yl]-6-methyl-phenoxy}-propane-1,2-diol.

xxxix) A further aspect of the invention relates to compounds of Formula (II)

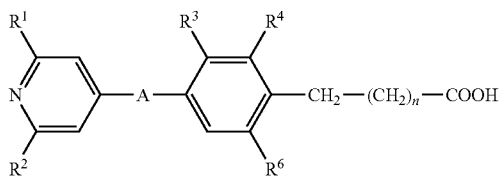

Formula (II)

wherein A, $R^1$, $R^2$, $R^3$, $R^4$, $R^6$, and n are as defined in claim 1.

The compounds of Formula (I) and their pharmaceutically acceptable salts can be used as medicaments, e.g. in the form of pharmaceutical compositions for enteral or parental administration.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy*, 20th Edition, Philadelphia College of Pharmacy and Science) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of Formula (I) are useful for the prevention and/or treatment of diseases or disorders associated with an activated immune system.

Such diseases or disorders are selected from the group consisting of rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveo-meningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' opthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; aneryth-roplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of Formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveoretinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

The present invention also relates to a method for the prevention or treatment of a disease or disorder mentioned herein comprising administering to a subject a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of Formula (I) for the preparation of a pharmaceutical composition, optionally for use in combination with one or several immunomodulating agents, for the prevention or treatment of the diseases and disorders mentioned herein.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

Structure 1

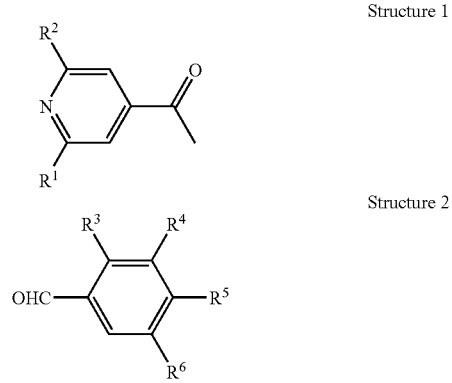

Structure 2

In case A represents —CO—CH═CH—, the compounds of Formula (I) may be prepared by reacting a compound of Structure 1 with a compound of Structure 2 in the presence of a base or an acid. The functional groups present in the residues $R^3$ to $R^6$ may require temporary protection or may even be introduced in additional steps that follow the condensation reaction. Compounds of Formula (I) wherein A represents —CO—CH$_2$—CH$_2$— may be prepared by reacting a compound of Formula (I) wherein A represents —CO—CH═CH— with hydrogen in the presence of a catalyst such as Pd/C, Pt/C, PtO$_2$, etc. in a solvent such as EtOH, MeOH, THF, etc. or mixtures thereof.

Structure 3

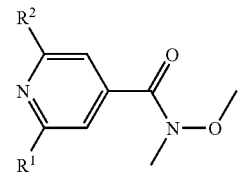

Structure 4

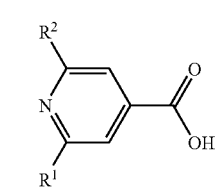

A compound of Structure 1 may be prepared by reacting a compound of Structure 3 with a methyl Grignard reagent or by treating a compound of Structure 4 with 2 equivalents of methyllithium in a solvent such as ether, THF, etc. at temperatures between −20 and 50° C. The Weinreb amide compound of Structure 3 is prepared by treating a compound of Structure 4 with N,O-dimethylhydroxylamine hydrochloride in the presence of coupling reagent such as EDC, DCC, etc. (M. Mentzel, H. M. R. Hoffmann, N-Methoxy N-methyl amides (Weinreb amides) in modern organic synthesis, *Journal fuer Praktische Chemie/Chemiker-Zeitung* 339 (1997), 517-524; J. Singh, N. Satyamurthi, I. S. Aidhen, The growing synthetic utility of Weinreb's amide, *Journal fuer Praktische Chemie* (Weinheim, Germany) 342 (2000) 340-347; V. K. Khlestkin, D. G. Mazhukin, Recent advances in the application of N,O-dialkylhydroxylamines in organic chemistry, Current Organic Chemistry 7 (2003), 967-993).

Structure 5

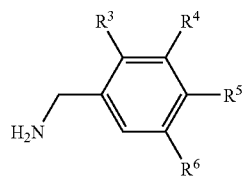

Compounds of Formula (I) wherein A represents —CO—NH—CH$_2$— may be prepared by coupling a compound of Structure 5 with a compound with Structure 4 by using a coupling reagent such as EDC, DCC, TBTU, PyBOP, etc. or by coupling a compound of Structure 5 with the corresponding acid chloride or bromide of a compound of Structure 4.

Compounds of Formula (I) which represent a 5-pyridin-4-yl-[1,2,4]oxadiazole derivative, are prepared by reacting a compound of Structure 6 in a solvent such as xylene, toluene, benzene, pyridine, DMF, THF, dioxane, DME, dichloromethane, acetic acid, trifluoroacetic acid, etc. at rt or elevated temperatures in the presence or absence of auxiliaries such as acids (e.g. TFA, acetic acid, HCl, etc.), bases (e.g. NaH, NaOAc, Na$_2$CO$_3$, K$_2$CO$_3$, NEt$_3$, etc.), tetraalkylammonium salts, or water removing agents (e.g. oxalyl chloride, a carboxylic acid anhydride, POCl₃, PCl₅, P₄O₁₀, molecular sieves, Burgess reagent, etc.) (Lit: e.g. A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Deprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292).

e.g. E. Meyer, A. C. Joussef, H. Gallardo, *Synthesis* 2003, 899-905, WO 2004/035538 (Merck & Co., Inc., USA)).

Structure 10

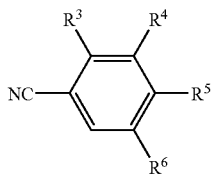

Structure 11

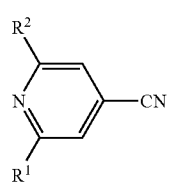

Structure 6

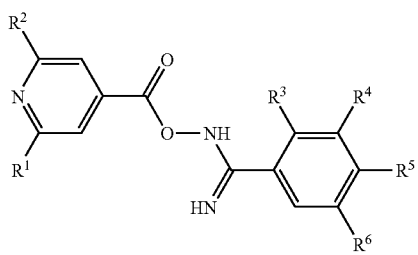

Compounds of Structure 6 may be prepared by reacting a compound of Structure 4 with a compound of Structure 7 in a solvent such as DMF, THF, DCM, etc. in the presence or absence of one or more coupling agents such as TBTU, DCC, EDC, HBTU, CDI, etc. and in the presence or absence of a base such as NEt₃, DIPEA, NaH, K₂CO₃, etc. (Lit: e.g. A. Hamze, J.-F. Hernandez, P. Fulcrand, J. Martinez, *J. Org. Chem.* 68 (2003) 7316-7321; and the literature cited above).

Depending on the nature of the functionalities present in the residues $R^3$ to $R^6$ in Structures 2, 5, 6, 7, 9, and 10, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, 3$^{rd}$ Edition, Wiley New York, 1991; P. J. Kocienski, Protecting Groups, Thieme Stuttgart, 1994). Alternatively, the desired residues $R^3$ to $R^6$, in particular $R^5$, may also be introduced in later steps that follow the coupling of the pyridine compounds of Structure 1, 4, 8 or 11 with the phenyl derivatives of Structure 2, 5, 7, 9 or 10 by using a suitable precursor of a compound of Structure 2, 5, 7, 9 and 10. The phenyl compounds of Structure 2, 5, 7, 9 and 10 or their precursors are either commercially available or are prepared according to procedures known to a person skilled in the art.

Structure 7

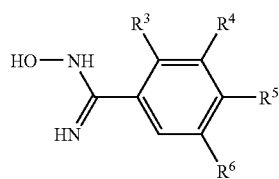

Compounds of Formula (I) which represent a 3-pyridin-4-yl-[1,2,4]oxadiazole derivative, are prepared in an analogous fashion (Lit. e.g. C. T. Brain, J. M. Paul, Y. Loong, P. J. Oakley, *Tetrahedron Lett.* 40 (1999) 3275-3278) by reacting a compound of Structure 8 with a compound of Structure 9 and subsequent cyclisation of the corresponding hydroxyamidine ester intermediate.

Structure 12

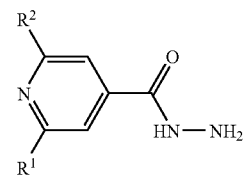

Structure 13

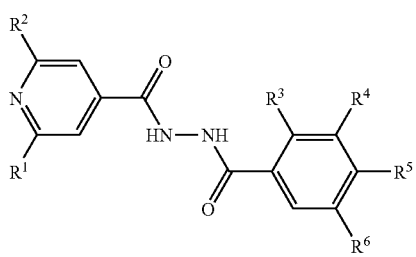

Structure 8

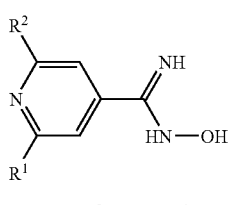

Structure 9

Compounds of Formula (I) which represent a 2-pyridin-4-yl-[1,3,4]oxadiazole or a 2-pyridin-4-yl-[1,3,4]thiadiazole derivative, are prepared similarly by reacting a compound of Structure 4 with hydrazine (by using a coupling reagent such as TBTU, DCC, EDC, HBTU, PyBOP, CDI, etc.) to form a compound of Structure 12 which is then coupled with a compound of Structure 9 to give a compound of Structure 13. A compound of Structure 13 can also be prepared by following the reverse reaction order i.e. by first coupling a compound of Structure 9 with hydrazine followed by reacting the corresponding hydrazide intermediate with a compound of Structure 4. Dehydration of a compound of Structure 13 to form the desired 2-pyridin-4-yl-[1,3,4]oxadiazole derivative is affected by treating a compound of Structure 13 with a Compounds of Structure 7 and 8 may be prepared by reacting a compound of Structure 10 and 11, respectively, with hydroxylamine or one of its salts in a solvent such as MeOH, EtOH, pyridine, etc. in the presence or absence of a base such as Na₂CO₃, K₂CO₃, potassium tert.butylate, NEt₃, etc. (Lit:

reagent such as POCl₃, CCl₄ or CBr₄ in combination with PPh₃, P₂O₅, Burgess reagent, etc. in a solvent such as toluene, MeCN, dioxane, THF, CHCl₃, etc. at temperatures between 20 and 120° C. in the presence or absence of microwave irradiation. (Lit. e.g. M. A. Garcia, S. Martin-Santamaria, M. Cacho, F. Moreno de la Llave, M. Julian, A. Martinez, B. De Pascual-Teresa, A. Ramos, *J. Med. Chem.* 48 (2005) 4068-4075, C. T. Brain, J. M. Paul, Y. Loong, P. J. Oakley, *Tetrahedron Lett.* 40 (1999) 3275-3278). Likewise, 2-pyridin-4-yl-[1,3,4]thiadiazole derivatives are obtained by cyclising a compound of Structure 13 with Lawesson's reagent optionally in combination with P₂S₅ in the presence or absence of a solvent such as pyridine, toluene, THF, MeCN, etc. at elevated temperatures with or without microwave irradiation (Lit. e.g. A. A. Kiryanov, P. Sampson, A. J. Seed, *J. Org. Chem.* 66 (2001) 7925-7929).

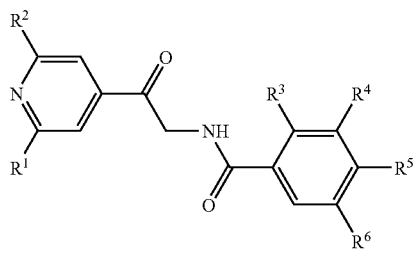

Structure 14

Compounds of Formula (I) which represent a 5-pyridin-4-yl-oxazole or a 5-pyridin-4-yl-thiazole derivative, are prepared by treating a compound of Structure 14 either with POCl₃, PCl₅, I₂ in combination with PPh₃ and NEt₃, Burgess reagent, trifluoracetic anhydride, etc. in a solvent such as toluene, benzene, dioxane, THF, etc. at temperatures between 20 and 120° C. or with Lawesson's reagent optionally in combination with P₂S₅ in the presence or absence of a solvent such as pyridine, toluene, THF, MeCN, etc. at elevated temperatures with or without microwave irradiation as mentioned above (Lit. e.g. N. Sato, T. Shibata, M. Jitsuoka, T. Ohno, T. Takahashi, T. Hirohashi, T. Kanno, H. Iwaasa, A. Kanatani, T. Fukami, Takehiro *Bioorg. & Med. Chem. Lett.* 14 (2004) 1761-1764). The compounds of Structure 14 are prepared by reacting a compound of Structure 15 with a compound of Structure 9. The aminoketon of Structure 15 can be prepared from a compound of Structure 1 by procedures given in the literature (e.g. J. L. LaMattina, *J. Heterocyclic Chem.* (1983) 533-538; M. Pesson, M. Antoine, P. Girard, J. L. Benichon, S. Chabassier, P. De Lajudie, S. Patte, F. Roquet, G. Montay, *Eur. J. Med. Chem.* 15 (1980) 263-268).

Compounds of Formula (I) which represent a 2-pyridin-4-yl-oxazole or a 2-pyridin-4-yl-thiazole derivative, are prepared in an analogous fashion from a compound of Structure 16 and a compound of Structure 4.

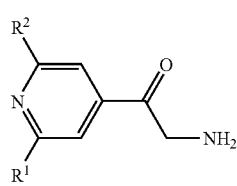

Structure 15

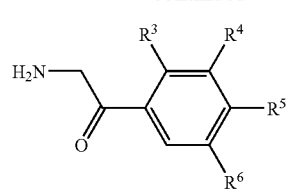

Structure 16

Alternatively, the bonds between the pyridine or the phenyl ring and the central 5-membered heteroaromatic ring can also be formed by applying palladium catalysed cross coupling reactions.

Methods that effect the transformation of a compound of Structure 4 into a compound of Structure 11, or the opposite, are known to a person skilled in the art.

Compounds of Structure 4 may be prepared by reacting a 2,6-dichloro-isonicotinic acid ester with an alkyl Grignard reagent in the presence of Fe(acac)₃ in a solvent such as THF, dioxane, DMF, NMP, etc., or combinations thereof, at temperatures ranging from −78 to 25° C. (Fürstner conditions, Lit. e.g. A. Fürstner, A. Leitner, M. Mendez, H. Krause *J. Am. Chem. Soc.* 124 (2002) 13856-13863; A. Fürstner, A. Leitner *Angew. Chem.* 114 (2002) 632-635). The reaction conditions can be chosen such that either the 2-chloro-6-alkyl-isonicotinic acid ester or the 2,6-dialkyl-isonicotinic acid ester is obtained as the main product. The two chlorine atoms in a 2,6-dichloro-isonicotinic acid ester may also be substituted either sequentially or in one step by two alk-1-enyl groups, which may be the same or different, by treating 2,6-dichloro-isonicotinic acid ester with the appropriate alkenyl boron derivative under Suzuki coupling conditions known to a person skilled in the art. The obtained 2,6-di-alkenyl-isonicotinic acid ester is hydrogenated to the corresponding 2,6-dialkyl-isonicotinic acid ester. In addition, a procedure in which the Fürstner and the Suzuki conditions are employed sequentially can be envisaged. The 2,6-dichloro-isonicotinic acid esters or the 2-chloro-6-alkyl-isonicotinic acid esters may also be treated with an alcohol or an alcoholate at elevated temperatures to furnish the corresponding 2-chloro-6-alkoxy-isonicotinic acid esters or 2-alkoxy-6-alkyl-isonicotinic acid esters (Lit. e.g. N. Wild, U. Groth *Eur. J. Org. Chem.* 2003, 4445-4449). Finally, cleavage of the ester functionality delivers the compounds of Structure 4.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as NEt₃, diethylamine) and eluent B (hexane), at a flow rate of 0.8 to 150 mL/min.

Experimental Part

I) Chemistry

The following examples illustrate the invention but do not at all limit the scope thereof.

All temperatures are stated in ° C. Compounds are characterized by ¹H-NMR (300 MHz) or ¹³C-NMR (75 MHz) (Varian Oxford; chemical shifts are given in ppm relative to the solvent used; multiplicities: s=singlet, d=doublet, t=triplet, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 µm, 120 Å, gradient: 5-95% MeCN in water, 1 min, with 0.04% trifluoroacetic acid, flow: 4.5 mL/min), $t_R$ is given in min, (retention times marked with * or as LC-MS* refer to LC run under basic conditions, i.e. eluting with a gradient of MeCN in water containing 13 mM of ammonium hydroxide, otherwise identical conditions); by TLC (TLC-plates from Merck, Silica gel 60 $F_{254}$); or by melting point. Compounds are purified by preparative HPLC (column: X-terra RP18, 50×19 mm, 5 µm, gradient: 10-95% MeCN in water containing 0.5% of formic acid) or by MPLC (Labomatic MD-80-100 pump, Linear UVIS-201 detector, column: 350×18 mm, Labogel-RP-18-5s-100, gradient: 10% MeOH in water to 100% MeOH).

Abbreviations (as Used Herein)
aq. aqueous
atm atmosphere
BSA bovine serum albumin
Burgess reagent methoxycarbonylsulfamoyl triethylammonium hydroxide
CC column chromatography
CDI carbonyl diimidazole
DCC dicyclohexyl carbodiimide
DCM dichloromethane
DEAD diethyl-diazodicarboxylate
DIPEA Hüning's base, diethylisopropylamine
DME 1,2-dimethoxyethane
DMF dimethylformamide
DMSO dimethylsulfoxide
dppf 1,1'-bis(diphenylphosphino)ferrocene
EA ethyl acetate
EDC N-(3-dimethylaminopropyl)-N'-ethyl-carbodiimide
ether diethyl ether
EtOH ethanol
Fe(acac)$_3$ iron(III) acetylacetone-complex
h hour(s)
HBTU O-(benzotriazol-1-yl)-N,N,N',N'-tetramethyluronium hexafluorophosphate
HOBt 1-hydroxy-benzotriazole
HPLC high performance liquid chromatography
HV high vacuum conditions
Lawesson's reagent 2,4-bis(4-methoxyphenyl)-1,3,2,4-dithiadiphosphetane-2,4-disulfide
LC-MS liquid chromatography-mass spectrometry
MeCN acetonitrile
MeOH methanol
min minute(s)
MPLC medium pressure liquid chromatography
NaOAc sodium acetate
NEt$_3$ triethylamine
NMO N-methyl-morpholine-N-oxide
NMP 1-methyl-2-pyrrolidone
OAc acetate
org. organic
Ph phenyl
PPh$_3$ triphenylphosphine
PyBOP benzotriazol-1-yl-oxy-tris-pyrrolidino-phosphonium-hexafluoro-phosphate
prep. preparative
rac racemic
rt room temperature
sat. saturated
S1P sphingosine 1-phosphate
TBME tert.-butyl methyl ether
TBTU 2-(1H-benzotriazole-1-yl)-1,2,3,3-tetramethyluronium tetrafluoroborate
tert. tertiary
TFA trifluoroacetic acid
THF tetrahydrofuran
TLC thin layer chromatography
$t_R$ retention time Preparation of Intermediates Isonicotinic Acid 1

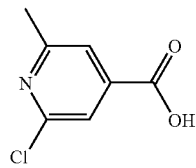

2-Chloro-6-methyl-isonicotinic acid is commercially available.

Isonicotinic Acid 2

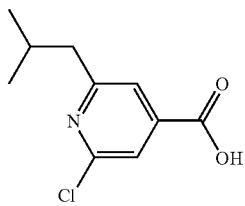

a) A suspension of 2,6-dichloroisonicotinic acid (5.23 g, 27.24 mmol) in toluene (100 mL) is heated to 80° C. and then slowly treated with N,N-dimethylformamide di-tert. butylacetal (19.94 g, 98.0 mmol). The mixture becomes slightly yellow and clear. Heating and stirring is continued for 3 h before the solution is cooled to rt, diluted with ether and washed with sat. aq. Na$_2$CO$_3$-solution. The org. extract is dried over MgSO$_4$, filtered and the solvent is evaporated to give 2,6-isonicotinic acid tert.-butyl ester (6.97 g) which solidifies as beige fine needles. $^1$H NMR (CDCl$_3$): δ 1.60 (s, 6 H), 7.73 (s, 1 H).

b) To a solution of 2,6-dichloro-isonicotinic acid tert.-butyl ester (1.74 g, 7.0 mmol), Fe(acac)$_3$ (706 mg, 2.0 mmol) and NMP (1.0 g, 10 mmol) in THF (250 mL), a solution of isobutylmagnesium chloride (1.15 g, 9.8 mmol) in THF is slowly added at −77° C. The brown solution turns turbid and black. Stirring is continued for 1 h at −72° C. before it is warmed to rt. The mixture is again cooled to −40° C. and then stirred for 16 h. The reaction is carefully quenched with 0.5 N aq. HCl (100 mL) and diluted with ether. The org. layer is separated and the aq. phase is extracted five more times with ether. The combined org. extracts are dried over MgSO$_4$, filtered and evaporated. The crude product is purified by MPLC on silica gel to give 2-chloro-6-isobutylisonicotinic acid tert.-butyl ester as a pale yellow oil (1.70 g) which contains 2,6-di-isobutylisonicotinic acid tert.-butyl ester as an impurity; LC-MS: $t_R$=1.12 min, $[M+1]^+$=270.07.

c) A solution of 2-chloro-6-isobutylisonicotinic acid tert.-butyl ester (1.70 g, 6.3 mmol) in 4 N HCl in dioxane (50 mL) is stirred at 60° C. for 30 h. The solvent is evaporated and the crude product is purified by MPLC on silica gel (heptane:EA gradient) to give 2-chloro-6-isobutylisonicotinic acid hydrochloride (0.81 g) as a beige resin; LC-MS: $t_R$=0.89 min, $[M+1]^+$=214.02.

Isonicotinic Acid 3

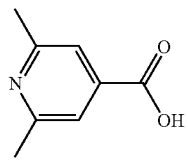

a) To a solution of 2,6-dichloro-isonicotinic acid tert.-butyl ester (3.35 g, 13.5 mmol), Fe(acac)$_3$ (512 mg, 1.45 mmol) and NMP (1.58 g, 16.0 mmol) in THF (400 mL), a solution of methylmagnesium iodide (11.67 g, 70.2 mmol) in THF is slowly added at −77° C. The brown solution turns green-grey. After the addition of about half of the Grignard reagent the dark brown suspension is warmed to it and stirred for 30 min before it is again cooled to −70° C. The other half of the Grignard reagent is added, the mixture turns dark green-brown and is warmed to it and stirred for 16 h. The mixture is cooled to −50° C. and another portion of the Grignard reagent (2.24 g, 13.5 mmol) is added. The reaction mixture is warmed to rt, stirred for 16 h and then carefully quenched with 1 N aq. HCl (100 mL) and diluted with ether. The org. layer is separated and the aq. phase is extracted with ether. The combined org. extracts are dried over MgSO$_4$, filtered and evaporated. The crude product is purified by MPLC on silica gel to give 2,6-dimethylisonicotinic acid tert.-butyl ester (2.37 g) as a pale yellow oil; LC-MS: $t_R$=0.65 min, [M+1]$^+$=208.29.

b) A solution of 2,6-dimethylisonicotinic acid tert.-butyl ester (2.37 g, 11.44 mmol) in 5 N HCl in isopropanol (40 mL) is stirred at 80° C. for 3 h. The solvent is evaporated and the crude product is purified by MPLC on silica gel (heptane:EA gradient) to give 2,6-dimethylisonicotinic acid hydrochloride as a beige resin; $^1$H NMR (CD$_3$OD): δ 8.16 (s, 2H), 2.84 (s, 6H).

Isonicotinic Acid 4

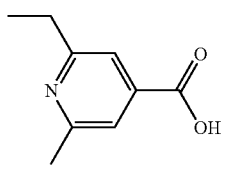

a) A suspension of 2-chloro-6-methyl-isonicotinic acid (7.0 g, 40.9 mmol) in toluene (100 mL) is heated to 80° C. and then slowly treated with N,N-dimethylformamide di-tert. butylacetal (21.2 g, 104.3 mmol). The mixture becomes clear. Heating and stirring is continued for 20 h before another portion N,N-dimethylformamide di-tert. butylacetal (8.32 g, 40.9 mmol) is added. Stirring is continued at 80° C. for 72 h. The reaction mixture is cooled to rt, diluted with ether and washed with sat. aq. Na$_2$CO$_3$-solution. The org. extract is dried over MgSO$_4$, filtered and the solvent is carefully evaporated. The crystalline material that formed is collected, carefully washed with cold heptane and dried to give 2-chloro-6-methyl-isonicotinic acid tert.-butyl ester (6.29 g) as colourless fine needles; LC-MS: $t_R$=1.01 min, [M+1]$^+$=228.11; $^1$H NMR (CDCl$_3$): δ 7.61 (s, 1H), 7.56 (s, 1H), 2.59 (s, 3H), 1.29 (s, 9H).

b) To a red solution of 2-chloro-6-methyl-isonicotinic acid tert.-butyl ester (2.95 g, 13.0 mmol), Fe(acac)$_3$ (512 mg, 1.45 mmol) and NMP (1.58 g, 16.0 mmol) in THF (400 mL), a solution of ethylmagnesium bromide (1.81 g, 13.6 mmol) in THF is slowly added at −77° C. The brown solution turns green-grey. The suspension is warmed to rt, stirred for 30 min before the yellow solution is again cooled to −70° C. and another portion of the Grignard reagent (1.38 g, 10.4 mmol) is added. The reaction mixture is warmed to rt, stirred for 16 h and then carefully quenched with 1 N aq. HCl (100 mL) and diluted with ether. The org. layer is separated and the aq. phase is extracted with ether. The combined org. extracts are dried over MgSO$_4$, filtered and evaporated. The crude product is purified by MPLC on silica gel to give 2-ethyl-6-methylisonicotinic acid tert.-butyl ester as a yellow oil which is dissolved in 4 N HCl in dioxane (50 mL). The solution is stirred at 50° C. for 16 h before the solvent is evaporated to give 2-ethyl-6-methylisonicotinic acid hydrochloride as a beige powder; LC-MS: $t_R$=0.28 min, [M+1]$^+$=166.25; $^1$H NMR (CDCl$_3$): δ 8.19 (s, 2H), 3.12 (q; J=7.6 Hz, 2H), 2.84 (s, 3H), 1.43 (t, J=7.6 Hz, 3H).

Isonicotinic Acid 5

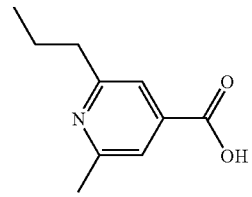

a) A solution of 2-chloro-6-methylisonicotinic acid (15.5 g, 90.3 mmol, 1 equivalent) in EtOH (200 mL) and a few drops of concentrated sulfuric acid is stirred at 75° C. for 24 h. The solvent is evaporated and the residue is dissolved in ethyl acetate (200 mL) and washed with a solution of sat. aq. NaHCO$_3$ (70 mL) and water (2×70 mL). The org. extract is dried over MgSO$_4$, filtered and evaporated to give 2-chloro-6-methylisonicotinic acid ethyl ester (16.3 g) as a pink powder; LC-MS: $t_R$=0.92 min, [M+1]$^+$=200.17.

b) To a solution of 2-chloro-6-methylisonicotinic acid ethyl ester (2.0 g, 10.0 mmol), and trans-propenyl boronic acid (1.30 g, 15.13 mmol) in DME (20 mL), a solution of 2 M aq. K$_2$CO$_3$ (3 mL) followed by Pd(PPh$_3$)$_4$ (150 mg, 0.205 mmol) and PPh$_3$ (265 mg, 0.99 mmol) is added. The mixture is stirred at 100° C. for 15 h before it is cooled to rt, diluted with ether and washed with sat. aq. Na$_2$CO$_3$ (2×30 mL). The org. extract is dried over Na$_2$SO$_4$, filtered and evaporated. The crude product is purified by CC on silica gel eluting with heptane:EA 4:1 to give 2-propenyl-6-methylisonicotinic acid ethyl ester (2.25 g) as a colourless oil; LC-MS: $t_R$=0.65 min, [M+1]$^+$=206.33.

c) 2-propenyl-6-methylisonicotinic acid ethyl ester (2.25 g, 10.9 mmol) is dissolved in THF (100 mL), Pd/C (300 mg, 10% Pd) is added and the mixture is stirred under 1 atm H$_2$ at rt for 15 h. The catalyst is filtered off and the filtrate is evaporated to give 2-propyl-6-methylisonicotinic acid ethyl ester (2.30 g) as a colourless oil; LC-MS: $t_R$=0.65 min, [M+1]$^+$=208.12 d) A solution of 2-propyl-6-methylisonicotinic acid ethyl ester (2.30 g, 11.0 mmol) in 6 N aq. HCl (40 mL) is stirred at 65° C. for 24 h before it is cooled to rt and extracted with ether (2×50 mL). The aq. phase is evaporated and the residue is dried under HV to give 2-propyl-6-methylisonicotinic acid hydrochloride (2.0 g) as a colourless solid, LC-MS: $t_R$=0.44 min; [M+1]$^+$=180.09; $^1$H NMR (D$_6$-DMSO): δ 8.02 (s, 1H), 7.99 (s, 1H), 3.04 (t, J=7.5 Hz, 2H), 2.78 (s, 3H), 1.82-1.72 (m, 2H), 0.93 (t, J=7.3 Hz, 3H).

Isonicotinic Acid 6

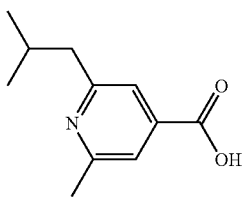

a) To a solution of 2-chloro-6-methylisonicotinic acid ethyl ester (9.92 g, 49.7 mmol), 2,4,6-tri-(2-methyl-propenyl)-cycloboroxane pyridine complex (13.0 g, 49.7 mmol, prepared in analogy to a procedure given by F. Kerins, D. F. O'Shea *J. Org. Chem.* 67 (2002) 4968-4971), and PPh$_3$ (1.39 g, 8.60 mmol) in DME (120 mL), a solution of 2 M aq. K$_2$CO$_3$ (40 mL) is added. The mixture is degassed and flushed with N$_2$ before Pd(PPh$_3$)$_4$ (580 mg, 0.793 mmol) is added. The mixture is stirred at 100° C. for 20 h before it is cooled to rt, diluted with EA and washed with sat. aq. NaHCO$_3$ (2×200 mL). The org. extract is dried over MgSO$_4$, filtered and evaporated. The crude product is purified by CC on silica gel eluting with heptane:EA 15:1 to give 2-methyl-6-(2-methyl-propenyl)-isonicotinic acid ethyl ester (9.90 g) as a yellow oil; LC-MS: $t_R$=0.44 min, $^1$H NMR (CDCl$_3$): δ 1.43 (m, 3 H), 1.98 (s, 3 H), 2.09 (s, 3 H), 2.63 (s, 3 H), 4.34-4.46 (m, 2 H), 6.39 (s, 1 H), 7.50 (s, 1 H), 7.56 (s, 1 H).

b) 2-Methyl-6-(2-methyl-propenyl)-isonicotinic acid ethyl ester (9.90 g, 45.2 mmol) is dissolved in THF (100 mL) and MeOH (100 mL), Pd/C (800 mg, 10% Pd) is added and the mixture is stirred under 1 atm H$_2$ at rt for 5 h. The catalyst is filtered off and the filtrate is evaporated. The crude product is purified by CC on silica gel eluting with hexane:EA 1:1 to give 2-methyl-6-(2-methyl-propyl)-isonicotinic acid ethyl ester (9.78 g) as a colourless oil; LC-MS: $t_R$=0.71 min.

c) A solution of 2-methyl-6-(2-methyl-propyl)-isonicotinic acid ethyl ester (9.78 g, 45.1 mmol) in 6 N aq. HCl (20 mL) is stirred at 95° C. for 20 h before the solvent is evaporated. The residue is dried under HV to give 2-methyl-6-(2-methyl-propyl)-isonicotinic acid hydrochloride (9.56 g) as a colourless solid, LC-MS: $t_R$=0.52 min.

Isonicotinic Acid 7

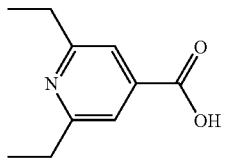

a) To a solution of 2,6-dichloro-isonicotinic acid tert.-butyl ester (780 mg, 3.14 mmol), and 2,4,6-trivinylcyclotriboroxane pyridine complex (640 mg, 2.66 mmol, prepared according to F. Kerins, D. F. O'Shea *J. Org. Chem.* 67 (2002) 4968-4971) in DME (12 mL), a solution of 2 M aq. K$_2$CO$_3$ (3 mL) followed by Pd(PPh$_3$)$_4$ (30 mg, 0.041 mmol) and PPh$_3$ (50 mg, 0.187 mmol) is added. The mixture is stirred at 100° C. for 15 h before it is cooled to rt, diluted with ether and washed with 1 N aq. NaOH solution (3×30 mL). The aq. phase is extracted once more with ether and the combined org. extracts are dried over Na$_2$SO$_4$, filtered and evaporated. The crude product is purified by CC on silica gel eluting with heptane:EA 5:1 to give 2,6-divinyl-isonicotinic acid tert-butyl ester (703 mg) as a colourless oil; LC-MS: $t_R$=1.03 min, [M+1]$^+$=232.01.

b) To a solution of 2,6-divinyl-isonicotinic acid tert-butyl ester (703 mg, 3.04 mmol) in MeOH (15 mL), Pd/C (50 mg, 10% Pd) is added and the mixture is stirred under 1 atm of H$_2$ at rt for 15 h. The catalyst is filtered off and the filtrate is evaporated. The remaining residue is purified by CC on silica gel eluting with heptane:EA 5:1 to give 2,6-diethyl-isonicotinic acid tert-butyl ester (635 mg) as a colourless oil; LC-MS: $t_R$=1.05 min, [M+1]$^+$=236.13.

c) A solution of 2,6-diethyl-isonicotinic acid tert-butyl ester (635 mg, 2.70 mmol) in 6 N aq. HCl (10 mL) is stirred at 95° C. for 15 h before the solvent is evaporated. The residue is dried under HV to give 2,6-diethyl-isonicotinic acid hydrochloride (523 mg) as a colourless solid, LC-MS: $t_R$=0.42 min, [M+1]$^+$=180.31; $^1$H NMR (D$_6$-DMSO): δ 7.95 (s, 2H), 3.05 (q, J=7.5 Hz, 4H), 1.31 (t, J=7.5 Hz, 6H).

Isonicotinic Acid 8

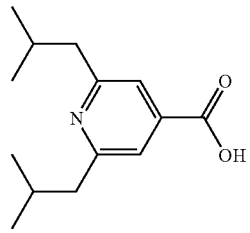 [SMILES: CC(C)Cc1cc(C(=O)O)cc(CC(C)C)n1]

2,6-Diisobutyl-isonicotinic acid hydrochloride is prepared starting from 2,6-dichloro-isonicotinic acid tert.-butyl ester and 2,4,6-tri-(2-methyl-propenyl)-cycloboroxane pyridine complex in analogy to isonicotinic acid 7; LC-MS: $t_R$=0.68 min; [M+1]$^+$=236.40; $^1$H NMR (D$_6$-DMSO): δ 7.90 (s, 2H), 2.92 (d, J=6.3 Hz, 4H), 2.10 (hept, J=6.8 Hz, 2H), 0.90 (t, J=6.5 Hz, 6H).

Isonicotinic Acid 9

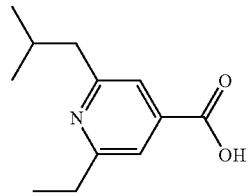

a) To a solution of 2,6-dichloro-isonicotinic acid tert.-butyl ester (500 mg, 2.02 mmol), and 2,4,6-trivinylcyclotriboroxane pyridine complex (170 mg, 0.706 mmol) in DME (12 mL), a solution of 2 M aq. K$_2$CO$_3$ (3 mL) followed by Pd(PPh$_3$)$_4$ (30 mg, 0.041 mmol) and PPh$_3$ (50 mg, 0.187 mmol) is added. The mixture is stirred at 45° C. for 15 h. 2,4,6-Tri-(2-methyl-propenyl)-cycloboroxane pyridine complex (594 mg, 1.83 mmol) is then added to the mixture and stirring is continued at 100° C. for 15 h. The mixture is cooled to rt, diluted with 1 N aq. NaOH solution and extracted twice with ether. The org. extracts are washed with 1 N aq. NaOH solution (2×30 mL), and brine, dried over Na$_2$SO$_4$, filtered and evaporated. The remaining residue is purified by CC on silica gel eluting with heptane:EA 5:1 to give 2-(2-methyl-propenyl)-6-vinyl-isonicotinic acid tert-butyl ester (780 mg) as a colourless oil containing 2,6-di-(2-methyl-propenyl)-isonicotinic acid tert.-butyl ester as impurity; LC-MS: $t_R$=1.01 min, [M+1]$^+$=260.14.

b) To a solution of the above 2-(2-methyl-propenyl)-6-vinyl-isonicotinic acid tert-butyl ester (444 mg, 1.71 mmol) in MeOH (15 mL), Pd/C (50 mg, 10% Pd) is added and the mixture is stirred under 1 atm of H$_2$ at rt for 15 h. The catalyst is filtered off and the filtrate is evaporated. The remaining residue is purified by CC on silica gel eluting with heptane:EA 5:1 to give 2-ethyl-6-isobutyl-isonicotinic acid tert-butyl ester (391 mg) as a colourless oil; LC-MS: $t_R$=1.15 min, $[M+1]^+$=264.11.

c) A solution of 2-ethyl-6-isobutyl-isonicotinic acid tert-butyl ester (391 mg, 1.49 mmol) in 6 N aq. HCl (15 mL) is stirred at 65° C. for 2 days before the solvent is evaporated. The residue is dried under HV to give 2-ethyl-6-isobutyl-isonicotinic acid hydrochloride (334 mg) as a colourless solid, LC-MS: $t_R$=0.58 min, $[M+1]^+$=208.04.

Isonicotinic Acid 10

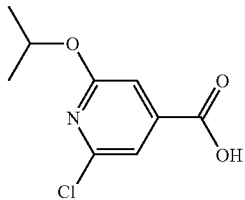

To a solution of K-tert.-butylate (3.72 g, 33.1 mmol) in isopropanol (20 mL) 2,6-dichloro-isonicotinic acid is added. The clear, colourless solution is stirred at 80° C. for 24 h. The mixture is cooled to rt, diluted with 1 N aq. HCl and extracted with ether (6×50 mL). The org. extracts are combined, dried over $Na_2SO_4$, filtered and concentrated. The residue is suspended in MeOH, filtered and the filtrate is evaporated to give 2-chloro-6-isopropoxy-isonicotinic acid (380 mg) as a beige solid, LC-MS: $t_R$=0.92 min, $[M+1]^+$=215.89.

Isonicotinic Acid 11

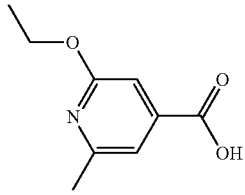

To a solution of K-tert.-butylate (1.99 g, 17.7 mmol) in EtOH (25 mL), 2-chloro-6-methyl-isonicotinic acid is added. The reaction mixture is stirred at 90° C. for 7 days. The mixture is cooled to rt, diluted with water and extracted with ether (3×50 mL). The aq. phase is acidified by adding 1 N aq. HCl and is then extracted three more times with ether (3×30 mL). The org. extracts are combined, dried over $Na_2SO_4$, filtered and concentrated. The crude product is purified by CC on silica gel eluting with heptane:EA 1:1 to give 2-ethoxy-6-methyl-isonicotinic acid (237 mg) as a white powder, LC-MS: $t_R$=0.60 min; $[M+1]^+$=182.24; $^1$H NMR ($CD_3OD$): δ 7.27 (s, 1 H), 7.04 (s, 1 H), 4.33 (q, J=7.0 Hz, 2 H), 2.46 (s, 3 H), 1.37 (t, J=7.0 Hz, 3 H).

Isonicotinic Acid 12

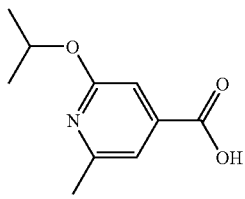

2-Isopropoxy-6-methyl-isonicotinic acid is prepared starting from 2-chloro-6-methyl-isonicotinic acid in analogy to isonicotinic acid 11 using isopropanol as solvent; LC-MS: $t_R$=0.70 min, $[M+1]^+$=196.04.

Isonicotinic Acid 13

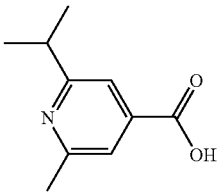

The title compound is prepared in analogy to 2-methyl-6-(2-methyl-propyl)-isonicotinic acid using 2,4,6-triisopropenyl-cyclotriboroxane; LC-MS: $t_R$=0.23 min; $[M+1]^+$=180.44.

Isonicotinic Acid 14

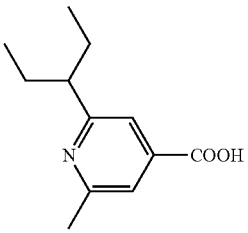

a) To a suspension of 2-chloro-6-methyl-isonicotinic acid (20.0 g, 117 mmol) in isopropanol (80 mL), $H_2SO_4$ (5 mL) is added dropwise. The mixture becomes warm (40° C.). The mixture is stirred for 24 h at rt, then at 90° C. for 28 h before the solvent is removed in vacuo. The residue is dissolved in ether (200 mL), washed with sat. aq. $NaHCO_3$-solution (3×50 mL) followed by brine (3×50 mL), dried over $Na_2SO_4$, filtered and concentrated to give 2-chloro-6-methyl-isonicotinic acid isopropyl ester (21.0 g) as a colourless oil which slowly crystallises; LC-MS: $t_R$=0.97 min, $[M+1]^+$=214.05.

b) A solution of 2-chloro-6-methyl-isonicotinic acid isopropyl ester (2.0 g, 9.36 mmol) in dioxane (75 mL) is degassed and put under argon before Pd(dppf) (229 mg, 0.281 mmol) is added. At rt, a 0.5 M solution of 1-ethyl-propylzinc bromide in THF (46.8 mL, 23.4 mmol) is added dropwise to the mixture. The mixture is stirred at 80° C. for 16 h before the reaction is quenched by adding ice-cold water (200 mL). A precipitate forms and the mixture is diluted with EA (200 mL) and filtered through celite. The filtrate is transferred into a separatory funnel. The org. phase is collected and the aq. phase is extracted with EA (120 mL). The combined org. extracts are dried over $MgSO_4$, filtered and concentrated. The crude product is purified by CC on silica gel eluting with heptane:EA 9:1 to 4:1 to give 2-(1-ethyl-propyl)-6-methyl-isonicotinic acid isopropyl ester (1.6 g) as a yellow oil; LC-MS: $t_R$=0.79 min, $[M+1]^+$=250.14; $^1$H NMR ($D_6$-DMSO): δ 0.70 (t, J=7.3 Hz, 6 H), 1.33 (d, J=6.3 Hz, 6 H), 1.58-1.70 (m, 4 H), 2.51 (s, 3 H), 2.55-2.63 (m, 1 H), 5.15 (hept, J=5.8 Hz), 7.39 (s, 1 H), 7.49 (s, 1 H).

c) A solution of 2-(1-ethyl-propyl)-6-methyl-isonicotinic acid isopropyl ester (1.54 g, 6.18 mmol) in 25% aq. HCl (60 mL) is stirred at 65° C. for 16 h. The solvent is removed in vacuo and the residue is dissolved in dioxane and concentrated again to give 2-(1-ethyl-propyl)-6-methyl-isonicotinic acid hydrochloride (1.70 g) as a brownish solid; LC-MS: $t_R$=0.62 min, $[M+1]^+$=208.52.

Isonicotinic Acid 15

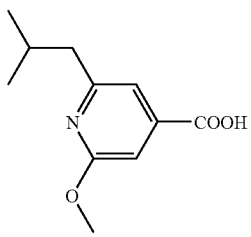

a) To a suspension of 2-chloro-6-methoxy-isonicotinic acid (2.00 g, 10.7 mmol) in MeOH (100 mL), $H_2SO_4$ (2 mL) is added. The mixture is stirred at 65° C. for 20 h. The solution is cooled to rt. A precipitate forms. The solid material is collected, washed with MeOH and dried to give 2-chloro-6-methoxy-isonicotinic acid methyl ester (1.66 g) as a white solid; LC-MS: $t_R$=1.29 min; $[M+1]^+$=202.00.

b) To a solution of 2-chloro-6-methoxy-isonicotinic acid methyl ester (1.66 g, 8.23 mmol) in dry THF (50 mL), NMP (1.1 mL, 11.5 mmol) is added. The mixture is cooled to −74° C. before a 2 M solution of isobutylmagnesium chloride (7 mL, 14.0 mmol) in THF is added. Stirring is continued at −75° C. for 1 h, before the mixture is warmed to 0° C. The reaction is quenched by carefully adding water. The mixture is diluted with EA, washed with water followed by brine, dried over $MgSO_4$, filtered and concentrated to give crude 2-isobutyl-6-methoxy-isonicotinic acid methyl ester (1.20 g) as an oil; LC-MS: $t_R$=1.37 min; $[M+1]^+$=224.12.

c) A solution of 2-isobutyl-6-methoxy-isonicotinic acid methyl ester (1.20 g, 5.38 mmol) in 25% aq. HCl (60 mL) is stirred at 65° C. for 16 h. The solvent is removed in vacuo and the residue is dried under HV to give 2-isobutyl-6-methoxy-isonicotinic acid hydrochloride (1.20 g) as a solid; LC-MS*: $t_R$=0.48 min, $[M+1]^+$=210.1.

Isonicotinic Acid 16

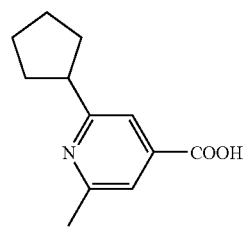

a) Under argon, Pd(dppf) (200 mg, 0.245 mmol) is added to a solution of 2-chloro-isonicotinic acid ethyl ester (4.80 g, 24.0 mmol) in dioxane (60 mL). A solution of cyclopentyl zinc chloride (50 mL, 24.0 mmol, ~2 M solution in THF) is added dropwise. The mixture is stirred at 75° C. for 2 h before it is cooled to rt, carefully diluted with water and extracted twice with EA. The combined org. extracts are dried over $MgSO_4$, filtered and concentrated. The crude product is purified by CC on silica gel eluting with heptane:EA 9:1 to give 2-cyclopentyl-6-methyl-isonicotinic acid ethyl ester (3.96 g) as an oil; LC-MS: $t_R$=0.72 min, $[M+1]^+$=234.11.

b) A solution of 2-cyclopentyl-6-methyl-isonicotinic acid ethyl ester (3.96 g, 17.0 mmol) in 25% aq. HCl (50 mL) is stirred at 75° C. for 16 h. The solvent is removed in vacuo and the remaining residue is dried under HV to give 2-cyclopentyl-6-methyl-isonicotinic acid hydrochloride (4.12 mg) as a white solid; LC-MS: $t_R$=0.54 min, $[M+1]^+$=206.08.

2-Ethyl-N-hydroxy-6-methyl-isonicotinamidine

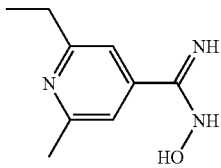

The title compound is prepared from isonicotinic acid 4 in analogy to steps e) to g) of the preparation of 3-[2-ethyl-4-(N-hydroxycarbamimidoyl)-6-methyl-phenyl]-propionic acid tert-butyl ester; LC-MS: $t_R$=0.23 min; $[M+1]^+$=180.07; $^1$H NMR ($d_6$-dmso): δ 1.22 (t, J=7.0 Hz, 3H), 2.44 (s, 3 H), 2.70 (q, J=7.8 Hz, 2H), 5.89 (s, 2 H), 7.31 (s, 2 H), 9.88 (s, 1 H).

N-Hydroxy-2-isobutyl-6-methyl-isonicotinamidine

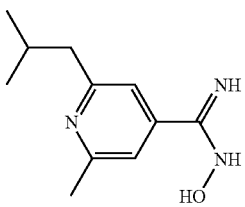

The title compound is prepared from isonicotinic acid 6 in analogy to steps e) to g) of the preparation of 3-[2-ethyl-4-(N-hydroxycarbamimidoyl)-6-methyl-phenyl]-propionic acid tert-butyl ester; LC-MS: $t_R$=0.52 min; $[M+1]^+$=208.12; $^1$H NMR (CDCl$_3$): δ 0.94 (d, J=6.5 Hz, 6 H), 2.06-2.17 (m, 1 H), 2.59 (s, 3 H), 2.68 (d, J=7.0 Hz, 2 H), 4.91 (s br, 2 H), 7.17 (s, 1 H), 7.22 (s, 1H), 8.97 (s br, 1 H).

4-Allyloxy-N-hydroxy-benzamidine

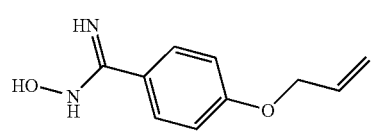

The title compound is prepared in analogy to 4-allyloxy-N-hydroxy-3,5-dimethyl-benzamidine by allylating commercially available 4-hydroxy-benzonitrile followed by transforming the nitrile to the hydroxyamidine; LC-MS: $t_R$=0.59 min, $[M+1]^+$=193.58.

4-Allyloxy-N-hydroxy-2-methyl-benzamidine

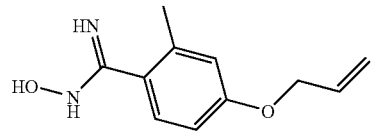

The title compound is prepared in analogy to 4-allyloxy-3-ethyl-N-hydroxy-5-methyl-benzamidine starting from commercially available 4-hydroxy-2-methyl-benzaldehyde; LC-MS: $t_R$=0.62 min, $[M+1]^+$=207.10; $^{13}$C NMR (CDCl$_3$): δ 20.72, 68.91, 104.72, 112.75, 116.45, 118.32, 118.53, 132.25, 134.19, 144.09, 161.71.

4-Allyloxy-N-hydroxy-2-methoxy-benzamidine

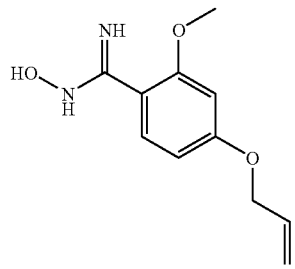 [SMILES: C=CCOc1ccc(C(=N)NO)c(OC)c1]

The title compound is prepared from commercially available 4-hydroxy-2-methoxy-benzaldehyde following literature procedures (references cited for 3-ethyl-4,N-dihydroxy-5-methyl-benzamidine); LC-MS: $t_R$=0.64 min; [M+1]$^+$=223.24; $^1$H NMR (D$_6$-DMSO): δ 9.33 (s br, 1H), 7.30 (d, J=8.2 Hz, 1H), 6.60 (d, J=2.3 Hz, 1H), 6.50 (dd, J=2.3, 8.2 Hz, 1H), 6.10-5.94 (m, 1H), 5.50 (s, 2H), 5.40 (d, J=17.0 Hz, 1H), 5.24 (d, J=10.6 Hz, 1H), 4.57 (d, J=4.7 Hz, 2H), 3.76 (s, 3H).

4-Allyloxy-N-hydroxy-3-methoxy-benzamidine

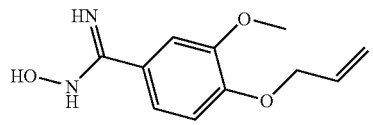 [SMILES: C=CCOc1ccc(C(=N)NO)cc1OC]

The title compound is prepared in analogy to 4-allyloxy-N-hydroxy-3,5-dimethyl-benzamidine by allylating commercially available 4-hydroxy-3-methoxy-benzonitrile followed by transforming the nitrile to the hydroxyamidine; LC-MS: $t_R$=0.59 min, [M+1]$^+$=223.18.

4-Allyloxy-3-chloro-N-hydroxy-5-methyl-benzamidine

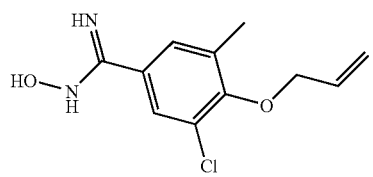 [SMILES: C=CCOc1c(C)cc(C(=N)NO)cc1Cl]

The title compound is prepared in analogy to 4-allyloxy-3-ethyl-N-hydroxy-5-methyl-benzamidine starting from commercially available 3-chloro-4-hydroxy-5-methyl-benzaldehyde; LC-MS: $t_R$=0.69 min, [M+1]$^+$=241.10.

4-Allyloxy-3-chloro-N-hydroxy-5-methoxy-benzamidine

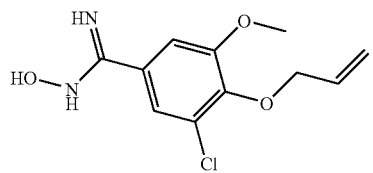 [SMILES: C=CCOc1c(Cl)cc(C(=N)NO)cc1OC]

The title compound is prepared in analogy to 4-allyloxy-N-hydroxy-3,5-dimethyl-benzamidine by allylating commercially available 3-chloro-4-hydroxy-5-methoxy-benzonitrile followed by transforming the nitrile to the hydroxyamidine; LC-MS: $t_R$=0.69 min, [M+1]$^+$=257.26, $^1$H NMR (CDCl$_3$): δ 3.92 (s, 3H), 4.65 (dt, J=6.0, 1.3 Hz, 2H), 5.26-5.30 (m, 1 H), 5.36-5.42 (m, 1H), 6.04-6.15 (m, 1 H), 7.07 (d, J=2.0 Hz, 1 H), 7.34 (d, J=1.8 Hz, 1 H).

4-Allyloxy-3-bromo-N-hydroxy-benzamidine

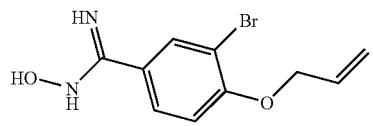

The title compound is prepared in analogy to 4-allyloxy-N-hydroxy-3,5-dimethyl-benzamidine by allylating commercially available 3-brome-4-hydroxy-benzonitrile followed by transforming the nitrile to the hydroxyamidine; LC-MS: $t_R$=0.68 min, [M+1]$^+$=270.96.

4-Allyloxy-N-hydroxy-3,5-dimethyl-benzamidine

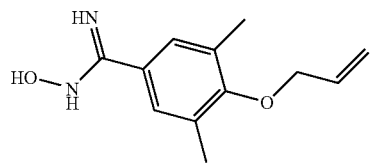 [SMILES: C=CCOc1c(C)cc(C(=N)NO)cc1C]

The title compound is prepared by allylating commercially available 4-hydroxy-3,5-dimethyl-benzonitrile with allylbromide in the presence of NaOH in isopropanol at rt. The nitrile is then transformed to the hydroxyamidine according to literature procedures (e.g. E. Meyer, A. C. Joussef, H. Gallardo, *Synthesis* 2003, 899-905); $^1$H NMR (CD$_3$OD): δ 7.27 (s, 2 H), 6.10 (m, 1 H), 5.42 (m, 1 H), 5.26 (m, 1H), 4.31 (dt, J=5.6, 1.5 Hz, 2 H), 2.29 (s, 6 H).

4-Allyloxy-3-ethyl-N-hydroxy-5-methyl-benzamidine

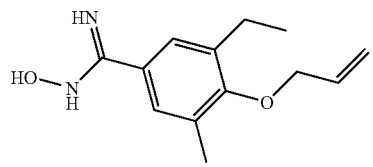 [SMILES: C=CCOc1c(C)cc(C(=N)NO)cc1CC]

The title compound is prepared by allylating 3-ethyl-4-hydroxy-5-methyl-benzaldehyde which is prepared from 2-ethyl-6-methyl-phenol following literature procedures (see 3-ethyl-4,N-dihydroxy-5-methyl-benzamidine). The aldehyde is then transformed into the corresponding hydroxyamidine according to literature procedures (see 3-ethyl-4,N-dihydroxy-5-methyl-benzamidine); LC-MS: $t_R$=0.72 min; [M+1]$^+$=235.09; $^1$H NMR (CD$_3$OD): δ 7.31 (s, 1 H), 7.29 (s, 1 H), 6.10 (m, 1 H), 5.43 (dd, J=17.0, 1.5 Hz, 1 H), 5.27 (dd, J=10.3, 1.2 Hz, 1 H), 4.81 (s br, 3 H), 4.31 (d, J=5.6 Hz, 2H), 2.67 (q, J=7.6 Hz, 2 H), 2.30 (s, 3 H), 1.23 (t, J=7.6 Hz, 4 H).

4,N-Dihydroxy-2-methoxy-benzamidine

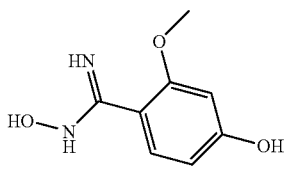

The title compound is prepared form commercially available 4-hydroxy-2-methoxy-benzaldehyde in analogy to 3-chloro-4,N-dihydroxy-5-methoxy-benzamidine; LC-MS: $t_R$=0.42 min; [M+1]$^+$=183.04.

4,N-Dihydroxy-3,5-dimethyl-benzamidine

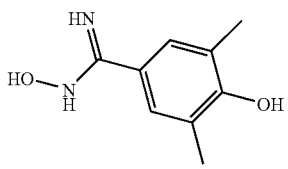

The title compound is prepared from commercially available 4-hydroxy-3,5-dimethyl-benzonitrile according to literature procedures (e.g. E. Meyer, A. C. Joussef, H. Gallardo, Synthesis 2003, 899-905); $^1$H NMR (CD$_3$OD): δ 7.20 (s, 2H), 2.20 (s, 6H).

3-Ethyl-4,N-dihydroxy-5-methyl-benzamidine

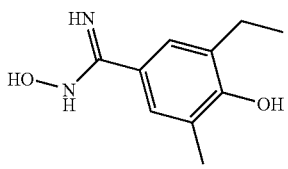

The title compound is prepared from commercially available 2-ethyl-6-methyl-phenol following literature procedures (G. Trapani, A. Latrofa, M. Franco, C. Altomare, E. Sanna, M. Usala, G. Biggio, G. Liso, J. Med. Chem. 41 (1998) 1846-1854; A. K. Chakraborti, G. Kaur, Tetrahedron 55 (1999) 13265-13268; E. Meyer, A. C. Joussef, H. Gallardo, Synthesis 2003, 899-905); LC-MS: $t_R$=0.55 min; $^1$H NMR (D$_6$-DMSO): δ 9.25 (s br, 1H), 7.21 (s, 2H), 5.56 (s, 2H), 2.55 (q, J=7.6 Hz, 2H), 2.15 (s, 3H), 1.10 (t, J=7.6 Hz, 3H).

4,N-Dihydroxy-3-methyl-5-propyl-benzamidine

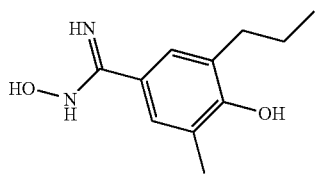

The title compound is prepared from commercially available 2-methyl-6-propyl-phenol in analogy to literature procedures (e.g B. Roth et al. J. Med. Chem. 31 (1988) 122-129; and literature cited for 3-ethyl-4,N-dihydroxy-5-methyl-benzamidine); LC-MS: $t_R$=0.54 min; [M+1]$^+$=209.43; $^1$H NMR (D$_6$-DMSO): δ 0.90 (t, J=7.3 Hz, 3 H), 1.48-1.59 (m, 3 H), 2.19 (s, 3 H), 2.56 (t, J=7.3 Hz, 2H), 7.37 (s, 1 H), 7.40 (s, 1 H), 9.34 (s, 1 H).

3,5-Diethyl-4,N-dihydroxy-benzamidine

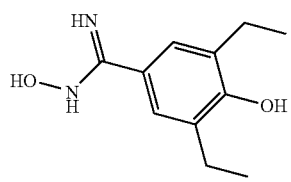

The title compound is prepared from commercially available 2,6-diethylaniline following literature procedures (G. G. Ecke, J. P. Napolitano, A. H. Filbey, A. J. Kolka, J. Org. Chem. 22 (1957) 639-642; and literature cited for 3-ethyl-4,N-dihydroxy-5-methyl-benzamidine); LC-MS: $t_R$=0.60 min; [M+1]$^+$=209.46.

3-Chloro-4,N-dihydroxy-5-methyl-benzamidine

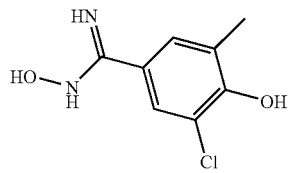

The title compound is prepared from commercially available 2-chloro-6-methyl-phenol in analogy to literature procedures (e.g B. Roth et al. J. Med. Chem. 31 (1988) 122-129; and literature cited for 3-ethyl-4,N-dihydroxy-5-methyl-benzamidine); 3-chloro-4-hydroxy-5-methyl-benzaldehyde: LC-MS: $t_R$=0.49 min; [M+1]$^+$=201.00; $^1$H NMR δ 2.24 (s, 2 H), 2.35 (s, 4 H), 5.98 (s br, 1 H), 7.59 (d, J=1.8 Hz, 1 H), 7.73 (d, J=1.8 Hz, 1 H), 9.80 (s, 1 H); 3-chloro-4,N-dihydroxy-5-methyl-benzamidine: $^1$H NMR (D$_6$-DMSO): δ 2.21 (s, 3 H), 5.72 (s br, 2 H), 7.40 (s, 1 H), 7.48 (s, 1 H), 9.29 (s br, 1 H), 9.48 (s br, 1 H).

3-Chloro-4,N-dihydroxy-5-methoxy-benzamidine

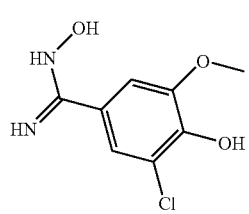

The title compound is prepared from commercially available 3-chloro-4-hydroxy-5-methoxy-benzaldehyde in analogy to the literature cited for 3-ethyl-4,N-dihydroxy-5-methyl-benzamidine; LC-MS: $t_R$=0.49 min; [M+1]$^+$=216.96; $^1$H NMR (D$_6$-DMSO): δ 3.84 (s, 3 H), 5.79 (s, 2 H), 7.22 (d, J=1.5 Hz, 1 H), 7.27 (d, J=1.8 Hz, 1 H), 9.52 (s, 1 H), 9.58 (s br, 1 H).

4,N-Dihydroxy-3-methoxy-5-methyl-benzamidine

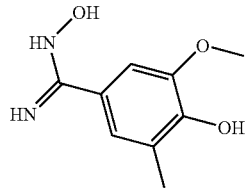

The title compound is prepared from commercially available 2-methoxy-6-methyl-phenol in analogy to literature procedures (e.g B. Roth et al. *J. Med. Chem.* 31 (1988) 122-129; and literature cited for 3-ethyl-4,N-dihydroxy-5-methyl-benzamidine); LC-MS: t$_R$=0.50 min; [M+1]$^+$=197.23.

[4-(N-Hydroxycarbamimidoyl)-phenyl]-acetic acid

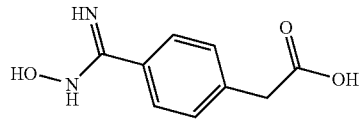 [SMILES: N=C(NO)c1ccc(CC(=O)O)cc1]

a) To a solution of methyl (4-cyanophenyl)acetate (4.00 g, 27.8 mmol) in MeOH (20 mL), hydroxylamine hydrochloride (3.17 g, 45.7 mmol) and NaHCO$_3$ (3.84 g, 45.7 mmol) is added. The suspension is stirred at 60° C. for 18 h before it is filtered and the filtrate is concentrated. The residue is dissolved in DCM, washed with water followed by brine, dried over MgSO$_4$, filtered, concentrated and dried to give methyl [4-(N-hydroxycarbamimidoyl)-phenyl]-acetate (3.67 g) as a colourless oil; LC-MS: t$_R$=0.50 min, [M+1]$^+$=209.05.

b) A solution of methyl [4-(N-hydroxycarbamimidoyl)-phenyl]-acetate (3.67 g, 17.6 mmol) in 25% aq. HCl (15 mL) is stirred at 65° C. for 4 h. The solvent is removed in vacuo and the residue is dried under high vacuum to give [4-(N-hydroxycarbamimidoyl)-phenyl]-acetic acid (3.80 g, presumably as hydrochloride) as a yellow solid; LC-MS: t$_R$=0.34 min, [M+1]$^+$=195.05.

{4-[5-(2-Isobutyl-6-methyl-pyridin-4-yl)-[1,2,4]oxadiazol-3-yl]-phenyl}-acetic acid

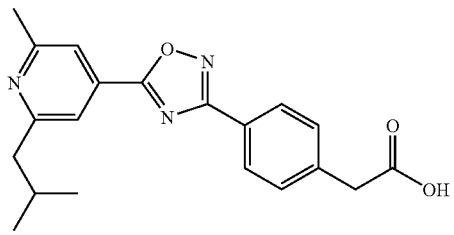 [SMILES: Cc1cc(-c2nc(-c3ccc(CC(=O)O)cc3)no2)cc(CC(C)C)n1]

The title compound is prepared starting from isonicotinic acid 6 and [4-(N-hydroxycarbamimidoyl)-phenyl]-acetic acid in analogy to Example 10; LC-MS: t$_R$=0.81 min, [M+1]$^+$=351.12.

3-Ethyl-4-hydroxy-5-methyl-benzoic acid

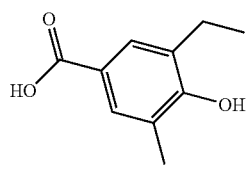

a) To an ice-cold solution of H$_2$SO$_4$ (150 mL) in water (250 mL) 2-ethyl-6-methylaniline (15.0 g, 111 mmol) is added. The solution is treated with ice (150 g) before a solution of NaNO$_2$ (10.7 g, 155 mmol) in water (150 mL) and ice (50 g) is added dropwise. The mixture is stirred at 0° C. for 1 h. 50% aq. H$_2$SO$_4$ (200 mL) is added and stirring is continued at rt for 18 h. The mixture is extracted with DCM, the org. extracts are dried over MgSO$_4$ and evaporated. The crude product is purified by CC on silica gel eluting with heptane:EA 9:1 to give 2-ethyl-6-methyl-phenol (8.6 g) as a crimson oil; LC-MS: t$_R$=0.89 min; $^1$H NMR (CDCl$_3$): δ 7.03-6.95 (m, 2H), 6.80 (t, J=7.6 Hz, 1H), 4.60 (s, 1H), 2.64 (q, J=7.6 Hz, 2H), 2.25 (s, 3H), 1.24 (t, J=7.6 Hz, 3H).

b) A solution of 2-ethyl-6-methyl-phenol (8.40 g, 61.7 mmol) and hexamethylene tetraamine (12.97 g, 92.5 mmol) in acetic acid (60 mL) and water (14 mL) is heated to 115° C. The water is distilled off at 117° C. and collected with a Dean-Stark apparatus. Then the water separator is replaced by a reflux condensor and the mixture is refluxed for 3 h. The mixture is cooled to rt, diluted with water (100 mL) and extracted with EA. The org. extract is washed with sat. aq. NaHCO$_3$, dried over MgSO$_4$ and evaporated. The remaining solid is dissolved in EA and treated with heptane to initialize crystallisation. The solid material is collected and dried to give 3-ethyl-4-hydroxy-5-methyl-benzaldehyde (3.13 g) as a colourless crystalline powder, $^1$H NMR (CDCl$_3$): δ 9.83 (s, 1H), 7.58-7.53 (m, 2H), 5.30 (s br, 1H), 2.69 (q, J=7.6 Hz, 2H), 2.32 (s, 3H), 1.28 (t, J=7.6 Hz, 3H).

c) To a solution of 3-ethyl-4-hydroxy-5-methyl-benzaldehyde (78.8 g, 0.48 mol) in DMSO (585 mL), a solution of NaH$_2$PO$_4$ dihydrate (17.3 g, 0.144 mol) in water (160 mL) is added over a period of 13 min. The mixture is stirred at rt an a solution of NaClO$_2$ (65.17 g, 0.577 mol) in water (160 mL) is added while the mixture is cooled with an ice-bath. The mixture is stirred for 1 h before a second portion of NaClO$_2$ (43.44 g, 0.480 mol) in water (100 mL) is added while the temperature is kept between 25 and 40° C. with an ice-bath. The yellow suspension is stirred at rt for 24 h before it is acidified with 32% aq. HCl to pH 2-3. The mixture is extracted with TBME (250 mL), the org. extract is washed with water, and the washings are extracted back with TBME. The solvent of the combined org. extracts is evaporated to give crude 3-ethyl-4-hydroxy-5-methyl-benzoic acid (80.3 g) as a yellow solid.

3-[2-Ethyl-4-(N-hydroxycarbamimidoyl)-6-methylphenyl]-propionic acid tert-butyl ester

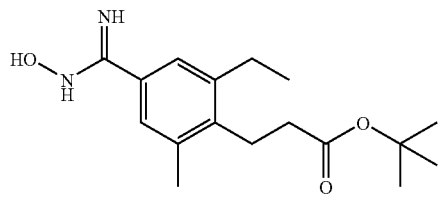 [SMILES: CCc1cc(C(=N)NO)cc(C)c1CCC(=O)OC(C)(C)C]

a) To a solution of 3-ethyl-4-hydroxy-5-methyl-benzoic acid (80.3 g, 0.446 mol) is DMF (500 mL), KHCO$_3$ (53.5 g, 0.535 mol) followed by benzylbromide (114.3 g, 0.668 mol) is added. The mixture is stirred at 50° C. for 18 h before it is cooled to rt, diluted with water (250 mL), and extracted with TBME (2×250 mL). The org. extracts are washed with water, and then concentrated. The crude product is purified by CC on silica gel eluting with heptane:EA 19:1 to 9:1 to give 3-ethyl-4-hydroxy-5-methyl-benzoic acid benzyl ester (108.5 g) as a beige solid; $^1$H NMR (CDCl$_3$): δ 1.28 (t, J=7.5 Hz, 3 H), 2.30 (s, 3 H), 2.68 (q, J=7.8 Hz, 2 H), 5.24 (s, 1 H), 5.37 (s, 2 H), 7.33-7.45 (m, 3 H), 7.45-7.50 (m, 2 H), 7.77 (s, 1 H), 7.79 (s, 1 H).

b) To a solution of 3-ethyl-4-hydroxy-5-methyl-benzoic acid benzyl ester (97.5 g, 0.361 mol) and pyridine (57.1 g, 0.721 mol) in DCM (1000 mL), a solution of trifluoromethanesulfonic anhydride (122.1 g, 0.433 mol) in DCM (100 mL) is added dropwise at 0° C. After complete addition, the mixture is stirred at rt for 2 h before it is washed with 2 N aq. HCl (500 mL) followed by water (500 mL). The org. extract is concentrated and dried to give 3-ethyl-5-methyl-4-trifluoromethanesulfonyloxy-benzoic acid (140.5 g) as an orange oil; $^1$H NMR δ 1.30 (t, J=7.5 Hz, 3 H), 2.46 (s, 3 H), 2.83 (q, J=7.5 Hz, 2 H), 5.39 (s, 2 H), 7.35-7.50 (m, 5 H), 7.87 (s, 1 H), 7.91 (s, 1 H).

c) To a solution of 3-ethyl-5-methyl-4-trifluoromethanesulfonyloxy-benzoic acid (10.0 g, 25 mmol), tert.-butyl acrylate (6.37 g, 50 mmol), NEt$_3$ (5.03 g, 50 mmol), and DPPP (0.82 g, 2 mmol) in DMF (100 mL), Pd(OAc)$_2$ (0.45 g, 2 mmol) is added under a N$_2$-atmosphere. The mixture is stirred at 115° C. for 3 h before is cooled to rt, filtered over a celite pad. The pad is washed with TBME (250 mL) and water (500 mL) is added to the filtrate. The layers are separated and the org. layer is washed twice with water (2×500 mL), dried over MgSO$_4$ and evaporated to dryness. To the crude product is added EtOH (100 mL). A thick suspension forms. The solid material is collected, washed with ice-cold EtOH (10 mL) to give 4-(2-tert-butoxycarbonyl-vinyl)-3-ethyl-5-methyl-benzoic acid benzyl ester (3.8 g) as an off-white solid.

d) To a solution of 4-(2-tert-butoxycarbonyl-vinyl)-3-ethyl-5-methyl-benzoic acid benzyl ester (10.0 g, 26 mmol) in THF 100 mL), Pd/C (0.5 g, 20% Pd) is added under nitrogen. The mixture is stirred at rt for 48 h under 1 bar of H$_2$. The catalyst is filtered off over a celite pad and the filtrate is concentrated to dryness to give 4-(2-tert-butoxycarbonyl-ethyl)-3-ethyl-5-methyl-benzoic acid (7.64 g) as a white solid; $^1$H NMR δ 1.29 (t, J=7.5 Hz, 3 H), 1.49 (s, 9 H), 2.36-2.41 (m, 2 H), 2.74 (q, J=7.5 Hz, 2 H), 2.99-3.05 (m, 2 H), 7.77 (s, 1 H), 7.80 (s, 1 H).

e) To a solution of 4-(2-tert-butoxycarbonyl-ethyl)-3-ethyl-5-methyl-benzoic acid (36.0 g, 123 mmol) in isopropanol (400 mL), HOBT (18.3 g, 135 mmol) followed by EDC HCl (27.1 g, 142 mmol) is added. The mixture is stirred at rt for 1 h before aq. ammonia (69 mL of 25% solution) is added. Stirring is continued for 1 h before the mixture is diluted with DCM (500 mL) and washed with half sat. aq. NaHCO$_3$ solution (3×400 mL), followed by water (400 mL). The org. extract is dried over MgSO$_4$, filtered and concentrated. The crude product is trituated with TBME 8250 mL). The solid material is collected, washed with additional TBME (50 mL) and dried under high vacuum to give 3-(4-carbamoyl-2-ethyl-6-methyl-phenyl)-propionic acid tert-butyl ester (31.91 g) as a white solid.

f) To a solution of 3-(4-carbamoyl-2-ethyl-6-methyl-phenyl)-propionic acid tert-butyl ester (30.0 g, 103 mmol) and NEt$_3$ (31.3 g, 309 mmol) in DCM (300 mL), trifluoroacetic anhydride (23.8 g, 113 mmol) is added slowly. The exothermic reaction is kept below 5° C. with cooling. After complete addition, the mixture is stirred at rt for 1 h. The mixture is washed twice with water (2×300 mL) and the org. extract is evaporated to dryness to give 3-(4-cyano-2-ethyl-6-methyl-phenyl)-propionic acid tert-butyl ester (28.4 g) as a pale yellow oil; $^1$H NMR δ 1.25 (t, J=7.5 Hz, 3 H), 1.48 (s, 9 H), 2.32-2.37 (m, 2 H), 2.38 (s, 3 H), 2.70 (q, J=7.5 Hz, 2 H), 2.95-3.02 (m, 2 H), 7.30 (s, 1 H), 7.34 (s, 1 H).

g) A solution of 3-(4-cyano-2-ethyl-6-methyl-phenyl)-propionic acid tert-butyl ester (37.0 g, 135 mmol), hydroxylamine hydrochloride (14.1 g, 203 mmol) and NEt$_3$ (27.4 g, 271 mmol) in MeOH (400 mL) is heated to reflux for 7 h before it is cooled to rt. The solvent is evaporated and the residue is taken up in isopropylacetate (500 mL) and washed twice with water (500 mL). The org. extract is dried over MgSO$_4$, filtered, evaporated and dried to give 3-[2-ethyl-4-(N-hydroxycarbamimidoyl)-6-methyl-phenyl]-propionic acid tert-butyl ester (40.8 g) as a pale yellow solid; $^1$H NMR δ 1.26 (t, J=7.5 Hz, 3 H), 1.49 (s, 9 H), 2.33-2.41 (m, 5 H), 2.66-2.74 (m, 2 H), 2.93-3.01 (m, 2 H), 4.85 (s, 1 H), 7.28 (s, 2 H).

3-{2-Ethyl-4-[5-(2-ethyl-6-methyl-pyridin-4-yl)-[1,2,4]oxadiazol-3-yl]-6-methyl-phenyl}-propionic acid

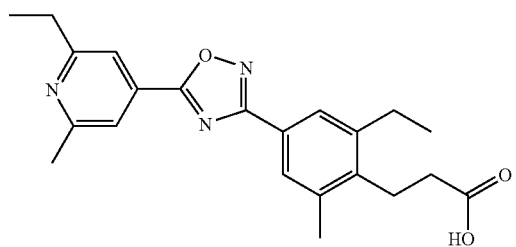 [SMILES: CCc1cc(-c2nc(-c3cc(C)c(CCC(=O)O)c(CC)c3)no2)cc(C)n1]

a) To a solution of isonicotinic acid 4 (100 mg, 0.496 mmol) and DIPEA (193 mg, 1.49 mmol) in DMF (2 mL), PyBOP (273 mg, 0.525 mmol) is added at 0° C. The mixture is stirred at 0° C. for 15 min before 3-[2-ethyl-4-(N-hydroxycarbamimidoyl)-6-methyl-phenyl]-propionic acid tert-butyl ester (152 mg, 0.496 mmol) is added. The mixture is stirred at rt for 1 h before it is diluted with water and aq. NaHCO$_3$ solution. The mixture is extracted twice with ether. The combined org. extracts are dried over MgSO$_4$, filtered and concentrated to give the crude hydroxyamidine ester intermediate (420 mg); LC-MS: $t_R$=0.90 min, [M+1]$^+$=454.47. This material is dissolved in dioxane and then stirred at 80° C. for 5 h. The solvent is evaporated to give crude 3-{2-ethyl-4-[5-(2-ethyl-6-methyl-pyridin-4-yl)-[1,2,4]oxadiazol-3-yl]-6-methyl-phenyl}-propionic acid tert. butyl ester; LC-MS: $t_R$=1.07 min, [M+1]$^+$=436.25.

b) A solution of the above 3-{2-ethyl-4-[5-(2-ethyl-6-methyl-pyridin-4-yl)-[1,2,4]oxadiazol-3-yl]-6-methyl-phenyl}-propionic acid tert. butyl ester in 6 N aq. HCl (10 mL) is stirred at 65° C. for 18 h. The solvent is evaporated and the residue is suspended in MeCN. The solid material is collected, washed with additional MeCN and dried under high vacuum to give 3-{2-ethyl-4-[5-(2-ethyl-6-methyl-pyridin-4-yl)-[1,2,4]oxadiazol-3-yl]-6-methyl-phenyl}-propionic acid (135 mg) as a white powder; LC-MS: $t_R$=0.86 min, [M+1]$^+$=380.13.

3-{2-Ethyl-4-[5-(2-isobutyl-6-methyl-pyridin-4-yl)-[1,2,4]oxadiazol-3-yl]-6-methyl-phenyl}-propionic acid

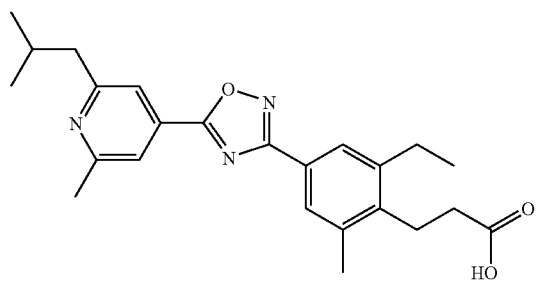 [SMILES: CCc1cc(-c2noc(-c3cc(C)nc(CC(C)C)c3)n2)cc(C)c1CCC(=O)O]

The title compound is prepared in analogy to 3-{2-ethyl-4-[5-(2-ethyl-6-methyl-pyridin-4-yl)-[1,2,4]oxadiazol-3-yl]-6-methyl-phenyl}-propionic acid starting from isonicotinic acid 6 and 3-[2-ethyl-4-(N-hydroxycarbamimidoyl)-6-methyl-phenyl]-propionic acid tert-butyl ester; LC-MS: $t_R$=0.93 min, [M+1]$^+$=408.22.

3-[4-(N-Hydroxycarbamimidoyl)-2,6-dimethyl-phenyl]-propionic acid tert-butyl ester

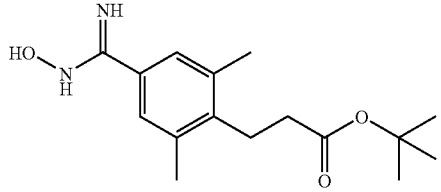 [SMILES: Cc1cc(C(=N)NO)cc(C)c1CCC(=O)OC(C)(C)C]

The title compound is prepared starting from 3,5-dimethyl-4-hydroxybenzonitrile following steps b), c), d), and g) of the preparation of 3-[2-ethyl-4-(N-hydroxycarbamimidoyl)-6-methyl-phenyl]-propionic acid tert-butyl ester; LC-MS: $t_R$=0.75 min, [M+1]$^+$=293.09.

3-{4-[5-(2-Isobutyl-6-methyl-pyridin-4-yl)-[1,2,4]oxadiazol-3-yl]-2,6-dimethyl-phenyl}-propionic acid

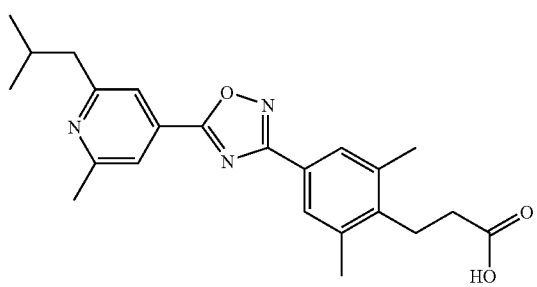 [SMILES: Cc1cc(-c2nc(-c3cc(C)c(CCC(=O)O)c(C)c3)no2)cc(CC(C)C)n1]

The title compound is prepared in analogy to 3-{2-ethyl-4-[5-(2-isobutyl-6-methyl-pyridin-4-yl)-[1,2,4]oxadiazol-3-yl]-6-methyl-phenyl}-propionic acid starting from 3-{4-[5-(2-isobutyl-6-methyl-pyridin-4-yl)-[1,2,4]oxadiazol-3-yl]-2,6-dimethyl-phenyl}-propionic acid and isonicotinic acid 6; LC-MS: $t_R$=0.89 min, [M+1]$^+$=394.11; $^1$H NMR (D$_6$-DMSO): δ 0.94 (d, J=6.5 Hz, 6 H), 2.11-2.22 (m, 1 H), 2.40 (s, 6 H), 2.76 (s, 3 H), 2.87-2.97 (m, 4 H), 3.65-3.74 (m, 2 H), 7.75 (s, 2 H), 8.09 (s, 1 H), 8.15 (s, 1 H).

4-Allyloxy-3,5-dimethyl-benzoic acid hydrazide

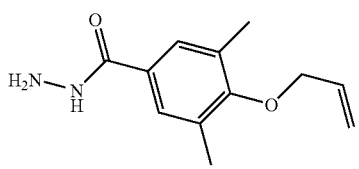 [SMILES: C=CCOc1c(C)cc(C(=O)NN)cc1C]

The title compound is prepared in analogy to 4-benzyloxy-3,5-dimethyl-benzoic acid hydrazide; LC-MS: $t_R$=0.71 min, [M+1]$^+$=221.20; $^1$H NMR (D$_6$-DMSO): δ 2.22 (s, 6 H), 4.28-4.33 (m, 2 H), 4.39 (s br, 2 H), 5.20-5.27 (m, 1 H), 5.37-5.46 (m, 1 H), 6.00-6.14 (m, 1 H), 7.49 (s, 2 H), 9.55 (s, 1 H).

4-Benzyloxy-3,5-dimethyl-benzoic acid hydrazide

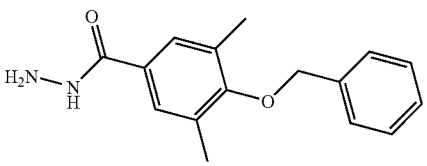 [SMILES: Cc1cc(C(=O)NN)cc(C)c1OCc1ccccc1]

To a solution of 4-benzyloxy-3,5-dimethyl-benzoic acid (10.9 g, 42.5 mmol) in CHCl$_3$ (140 mL) is added thionylchloride (33.1 g, 278 mmol) and the mixture is heated at reflux for 2 h. The mixture is evaporated and the residue dissolved in THF (300 mL) and then added to a cooled (−78° C.) solution of 1M hydrazine in THF (175 mL). The mixture is slowly warmed to rt during 15 h, diluted with ether (150 mL) and washed with 1M aq. HCl (5×50 mL). The combined org. extracts are washed with 33% aq. KOH, dried over MgSO$_4$, filtered and evaporated The crude product is purified by MPLC on reverse phase silica gel eluting with water/MeOH to give the title compound (2.97 g) as a white solid; LC-MS: $t_R$=0.81 min; [M+1]$^+$=271.41.

4-Benzyloxy-3-ethyl-5-methyl-benzoic acid hydrazide

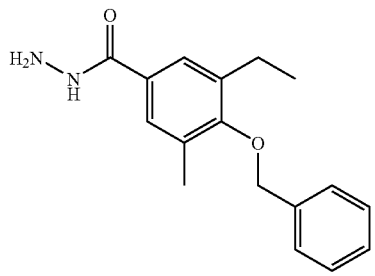 [SMILES: CCc1cc(C(=O)NN)cc(C)c1OCc1ccccc1]

a) To a solution of 3-ethyl-4-hydroxy-5-methyl-benzaldehyde (34.9 g, 0.213 mol, prepared from 2-ethyl-6-methyl-phenol according to the literature cited for 3-ethyl-4,N-dihydroxy-5-methyl-benzamidine) in MeCN (350 mL), K$_2$CO$_3$ (58.7 g, 0.425 mol) and benzylbromide (36.4 g, 0.213 mol) is added. The mixture is stirred at 60° C. for 2 h before it is cooled to rt, diluted with water and extracted twice with EA. The org. extracts are washed with water and concentrated to give crude 4-benzyloxy-3-ethyl-5-methyl-benzaldehyde (45 g) as an orange oil. $^1$H NMR (CDCl$_3$): δ 1.29 (t, J=7.5 Hz, 3 H), 2.40 (s, 3 H), 2.77 (q, J=7.8 Hz, 2 H), 4.90 (s, 2 H), 7.31-7.52 (m, 5 H), 7.62 (d, J=1.5 Hz, 1 H), 7.66 (d, J=1.8 Hz, 1 H), 9.94 (s, 1 H).

b) To a mixture of 4-benzyloxy-3-ethyl-5-methyl-benzaldehyde (132 g, 0.519 mol) and 2-methyl-2-butene (364 g, 5.19 mol) in tert.-butanol (1500 mL), a solution of NaH$_2$PO$_4$ dihydrate (249 g, 2.08 mol) in water (1500 mL) is added. To this mixture, NaClO$_2$ (187.8 g, 2.08 mol) is added in portions. The temperature of the reaction mixture is kept below 30° C., and evolution of gas is observed. Upon completion of the addition, the orange bi-phasic mixture is stirred well for 3 h before it is diluted with TBME (1500 mL). The org. layer is separated and washed with 20% aq. NaHS solution (1500 mL) and water (500 mL). The org. phase is then extracted three times with 0.5 N aq. NaOH (1000 mL), the aq. phase is acidified with 25% aq. HCl (500 mL) and extracted twice with TBME (1000 mL). These org. extracts are combined and evaporated to dryness to give 4-benzyloxy-3-ethyl-5-methyl-benzoic acid; $^1$H NMR (D$_6$-DMSO): δ 1.17 (t, J=7.5 Hz, 3H), 2.31 (s, 3 H), 2.67 (q, J=7.5 Hz, 2 H), 4.86 (s, 2 H), 7.34-7.53 (m, 5 H), 7.68 (s, 2 H), 12.70 (s, 1 H).

c) 4-Benzyloxy-3-ethyl-5-methyl-benzoic acid is converted to 4-benzyloxy-3-ethyl-5-methyl-benzoic acid hydrazide following step c) of the preparation of 4-allyloxy-3,5-dimethyl-benzoic acid hydrazide; LC-MS: $t_R$=0.82 min, [M+1]$^+$=285.44.

4-Benzyloxy-3-chloro-5-methoxy-benzoic acid hydrazide

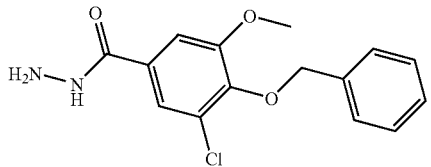 [SMILES: COc1cc(C(=O)NN)cc(Cl)c1OCc1ccccc1]

The title compound is prepared in analogy to 4-benzyloxy-3-ethyl-5-methyl-benzoic acid hydrazide from 3-chloro-4-hydroxy-5-methoxy-benzaldehyde; LC-MS: $t_R$=0.82 min, [M+1]$^+$=307.01.

Methanesulfonic acid 2,2-dimethyl-[1,3]dioxan-5-ylmethyl ester

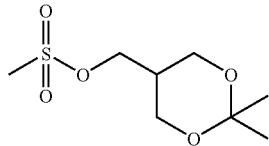

The title compound is prepared following the procedures given in B. Xu, A. Stephens, G. Kirschenheuter, A. F. Greslin, X. Cheng, J. Sennelo, M. Cattaneo, M. L. Zighetti, A. Chen, S.-A. Kim, H. S. Kim, N. Bischofberger, G. Cook, K. A. Jacobson, *J. Med. Chem.* 45 (2002) 5694-5709.

PREPARATION OF EXAMPLES

Example 1

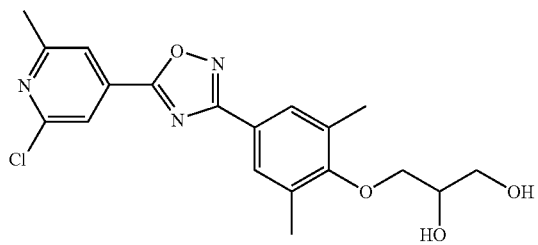 [SMILES: Cc1cc(-c2nc(-c3cc(C)c(OCC(O)CO)c(C)c3)no2)cc(Cl)n1]

a) A solution of 2-chloro-6-methyl-isonicotinic acid (227 mg, 1.33 mmol), PyBOP (700 mg, 1.34 mmol), DIPEA (860 mg, 6.64 mmol), and 4-allyloxy-N-hydroxy-3,5-dimethyl-benzamidine (410 mg, 1.86 mmol) in DCM (7 mL) is stirred at rt for 1 h. The mixture is diluted with ether, washed with 1 N aq. HCl (2×25 mL), 1 N aq. KHSO$_4$ solution (2×25 mL) and brine (25 mL), dried over Na$_2$SO$_4$, filtered and concentrated. The crude product is purified by MPLC on silica gel eluting with a gradient of EA in heptane to give 2-chloro-6-methyl-isonicotinic acid (4-allyloxy-N-hydroxy-3,5-dimethyl-benzamidine) ester (142 mg) as a colourless resin; LC-MS: $t_R$=1.04 min, [M+1]$^+$=374.10.

b) A solution of 2-chloro-6-methyl-isonicotinic acid (4-allyloxy-N-hydroxy-3,5-dimethyl-benzamidine) ester (142 mg, 0.38 mmol) in dioxane (6 mL) is stirred at 90° C. for 16 h. The solvent is evaporated to give 4-[3-(4-allyloxy-3,5-dimethyl-phenyl)-[1,2,4]oxadiazol-5-yl]-2-chloro-6-methyl-pyridine (137 mg) as a beige solid; LC-MS: $t_R$=1.22 min, [M+1]$^+$=356.35.

c) To a solution of 4-[3-(4-allyloxy-3,5-dimethyl-phenyl)-[1,2,4]oxadiazol-5-yl]-2-chloro-6-methyl-pyridine (137 mg, 0.385 mmol) in acetone (6 mL) and water (1 mL), NMO (385 mg, 2.80 mmol) followed by OsO$_4$ (48 mg, 0.189 mmol, 2.5% in tert.-butanol) is added. The mixture is stirred at rt for 16 h before it is diluted with 1 N aq. KHSO$_4$-solution and extracted with ether (3×50 mL). The combined org. extracts are dried over Na$_2$SO$_4$, filtered and concentrated. A sample (10 mg) of the crude product (146 mg) is purified by chromatography on prep. TLC plates with heptane:EA 1:3 to give (RS)-3-{4-[5-(2-chloro-6-methyl-pyridin-4-yl)-[1,2,4]oxadiazol-3-yl]-2,6-dimethyl-phenoxy}-propane-1,2-diol (5 mg) as a colourless resin; LC-MS: $t_R$=0.95 min, [M+1]$^+$=390.10.

Example 2

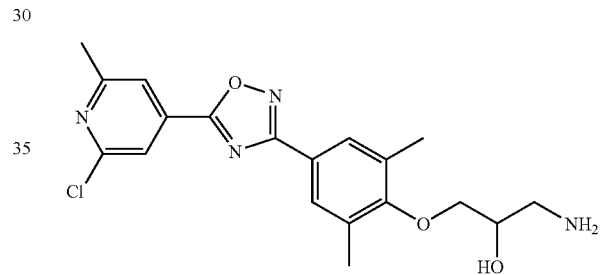

To a solution of (RS)-3-{4-[5-(2-chloro-6-methyl-pyridin-4-yl)-[1,2,4]oxadiazol-3-yl]-2,6-dimethyl-phenoxy}-propane-1,2-diol (134 mg, 0.345 mmol) in THF (5 mL), DIPEA (89 mg, 0.69 mmol) followed by methanesulfonylchloride (43 mg, 0.379 mmol) is added at 0° C. The mixture is stirred at it for 2 h before 7 M NH$_3$ in MeOH (1.2 mL) is added. The mixture is stirred at 65° C. for 16 h before the solvent is removed in vacuo to give crude (RS)-1-amino-3-{4-[5-(2-chloro-6-methyl-pyridin-4-yl)-[1,2,4]oxadiazol-3-yl]-2,6-dimethyl-phenoxy}-propan-2-ol as beige resin; LC-MS: $t_R$=0.80 min, [M+1]$^+$=388.96.

Example 3

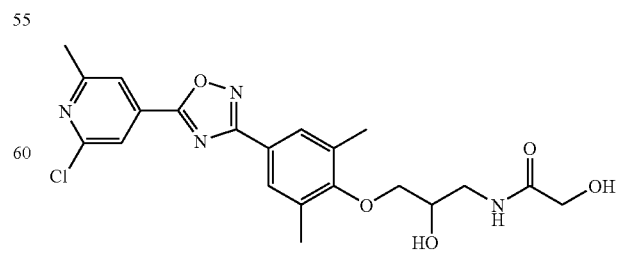

To a solution of (RS)-1-amino-3-{4-[5-(2-chloro-6-methyl-pyridin-4-yl)-[1,2,4]oxadiazol-3-yl]-2,6-dimethyl-phenoxy}-propan-2-ol (134 mg, 0.345 mmol) in DCM (10 mL), glycolic acid (54 mg, 0.707 mmol) and DIPEA (132 mg, 1.02 mmol) is added. The mixture is cooled to 0° C. and TBTU (134 mg, 0.416 mmol) is added. The mixture is stirred at 0° C. for 1 h, then at rt for 16 h before it is diluted with EA (250 mL), washed with 1 N aq. NaOH solution (3×25 mL), 1 N aq. KHSO$_4$ (25 mL) and brine (25 mL), dried over Na$_2$SO$_4$, filtered and concentrated. The crude product is purified by prep. HPLC to give N-((RS)-3-{4-[5-(2-chloro-6-methyl-pyridin-4-yl)-[1,2,4]oxadiazol-3-yl]-2,6-dimethyl-phenoxy}-2-hydroxy-propyl)-2-hydroxy-acetamide (23 mg) as a colourless resin; LC-MS: $t_R$=0.91 min, [M+1]$^+$=447.44.

Example 4

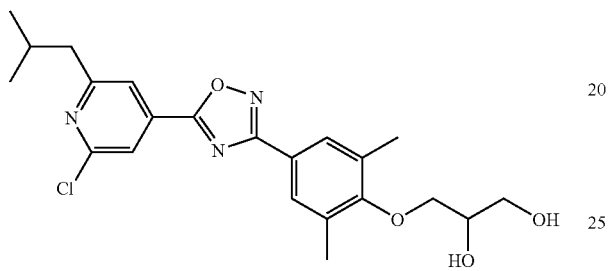

(RS)-3-{4-[5-(2-Chloro-6-isobutyl-pyridin-4-yl)-[1,2,4]oxadiazol-3-yl]-2,6-dimethyl-phenoxy}-propane-1,2-diol is prepared in analogy to Example 1; LC-MS: $t_R$=1.06 min, [M+1]$^+$=432.15.

Example 5

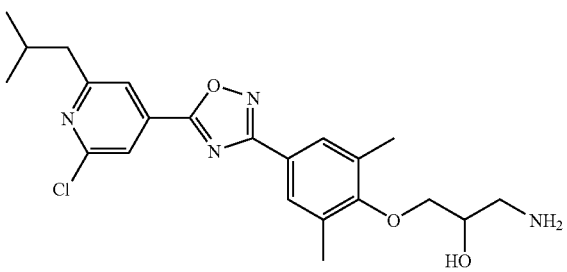

(RS)-1-Amino-3-{4-[5-(2-chloro-6-isobutyl-pyridin-4-yl)-[1,2,4]oxadiazol-3-yl]-2,6-dimethyl-phenoxy}-propan-2-ol is prepared in analogy to Example 2; LC-MS: $t_R$=0.91 min, [M+1]$^+$=431.38.

Example 6

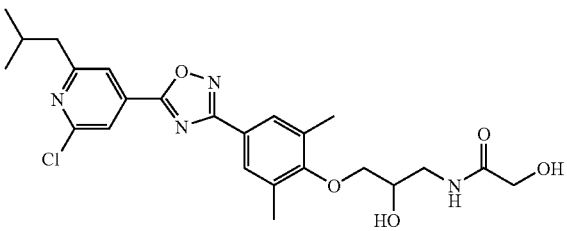

N-((RS)-3-{4-[5-(2-Chloro-6-isobutyl-pyridin-4-yl)-[1,2,4]oxadiazol-3-yl]-2,6-dimethyl-phenoxy}-2-hydroxy-propyl)-2-hydroxy-acetamide is prepared in analogy to Example 3; LC-MS: $t_R$=1.01 min, [M+1]$^+$=489.26.

Example 7

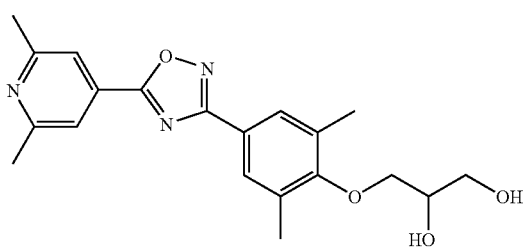 [SMILES: Cc1cc(-c2nc(-c3cc(C)c(OCC(O)CO)c(C)c3)no2)cc(C)n1]

(RS)-3-{4-[5-(2,6-Dimethyl-pyridin-4-yl)-[1,2,4]oxadiazol-3-yl]-2,6-dimethyl-phenoxy}-propane-1,2-diol is prepared in analogy to Example 1; LC-MS: $t_R$=1.01 min, [M+1]$^+$=489.26.

Example 8

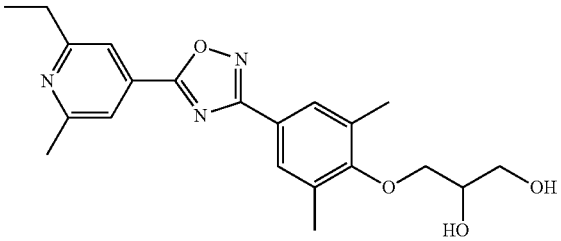 [SMILES: CCc1cc(-c2nc(-c3cc(C)c(OCC(O)CO)c(C)c3)no2)cc(C)n1]

(RS)-3-{4-[5-(2-Ethyl-6-methyl-pyridin-4-yl)-[1,2,4]oxadiazol-3-yl]-2,6-dimethyl-phenoxy}-propane-1,2-diol is prepared in analogy to Example 1; LC-MS: $t_R$=0.73 min; [M+1]$^+$=383.45; $^1$H NMR (CDCl$_3$): δ 7.87 (s, 1 H), 7.86 (s, 1H), 7.75 (s, 1 H), (7.73 (s, 1H), 4.12-4.21 (m, 1 H), 3.81-3.98 (m, 4 H), 2.98-2.91 (m, 2H), 2.78 (s br, 1 H), 2.69 (s, 3 H), 2.41 (s, 6 H), 2.15 (s br, 1H), 1.42-1.36 (m, 3H).

Example 9

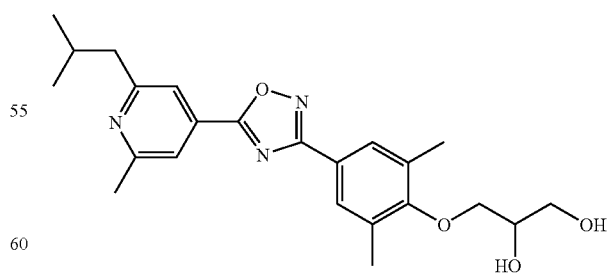

(RS)-3-{4-[5-(2-Isobutyl-6-methyl-pyridin-4-yl)-[1,2,4]oxadiazol-3-yl]-2,6-dimethyl-phenoxy}-propane-1,2-diol is prepared in analogy to Example 1; LC-MS: $t_R$=0.81 min; [M+1]$^+$=412.15; $^1$H NMR (CD$_3$OD): δ 7.85 (s, 1 H), 7.83 (s, 2 H), 7.79 (s, 1 H), 4.00-4.08 (m, 1 H), 3.92-3.99 (m, 1 H), 3.83-3.91 (m, 1 H), 3.67-3.80 (m, 2 H), 2.78 (d, J=7.3 Hz, 2 H), 2.67 (s, 3 H), 2.40 (s, 6 H), 2.14 (hept, J=6.5 Hz, 1 H), 1.00 (d, J=6.5 Hz, 6 H).

Example 10

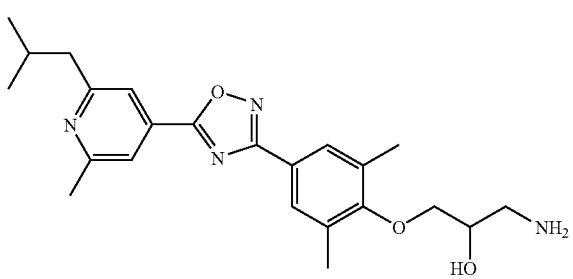 [SMILES: Cc1cc(-c2nc(-c3cc(C)c(OCC(O)CN)c(C)c3)no2)cc(CC(C)C)n1]

(RS)-1-Amino-3-{4-[5-(2-isobutyl-6-methyl-pyridin-4-yl)-[1,2,4]oxadiazol-3-yl]-2,6-dimethyl-phenoxy}-propan-2-ol is prepared in analogy to Example 2; LC-MS: $t_R$=0.72 min, [M+1]$^+$=411.20.

Example 11

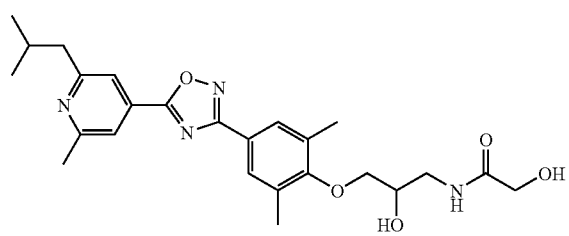

2-Hydroxy-N-((RS)-2-hydroxy-3-{4-[5-(2-isobutyl-6-methyl-pyridin-4-yl)-[1,2,4]oxadiazol-3-yl]-2,6-dimethyl-phenoxy}-propyl)-acetamide is prepared in analogy to Example 3; LC-MS: $t_R$=0.79 min, [M+1]$^+$=469.32.

Example 12

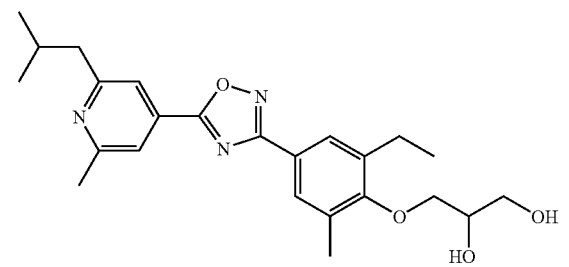 [SMILES: CCc1cc(-c2noc(-c3cc(C)nc(CC(C)C)c3)n2)cc(C)c1OC[C@@H](O)CO]

(RS)-3-{2-Ethyl-4-[5-(2-isobutyl-6-methyl-pyridin-4-yl)-[1,2,4]oxadiazol-3-yl]-6-methyl-phenoxy}-propane-1,2-diol is prepared in analogy to Example 1; LC-MS: $t_R$=0.84 min; [M+1]$^+$=426.16; $^{13}$C NMR (CDCl$_3$): δ 14.8, 16.4, 22.4, 22.9, 24.6, 29.2, 47.5, 63.7, 71.0, 73.8, 118.1, 118.2, 122.4, 126.6, 128.3, 131.4, 131.7, 137.7, 157.4, 159.4, 162.7, 168.9, 174.3.

Example 13

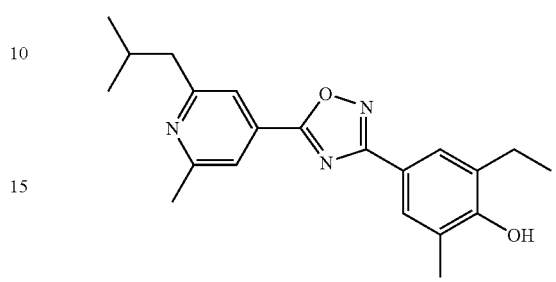

To a solution of 2-isobutyl-6-methyl-isonicotinic acid hydrochloride (2.18 g, 9.53 mmol) and DIPEA (3.69 g, 28.6 mmol) in DCM (10 mL), TBTU (3.67 g, 11.44 mmol) is added. The mixture is stirred for 5 min before 3,5-diethyl-4,N-dihydroxy-benzamidine (1.85 g, 9.53 mmol) is added. The mixture is stirred at rt for 1 h. The mixture is diluted with DCM, washed with sat. aq. NaHCO$_3$ solution, dried over MgSO$_4$, filtered and concentrated. The crude 2-isobutyl-6-methyl-isonicotinic acid (3-ethyl-4,N-dihydroxy-5-methyl-benzamidine) ester (LC-MS: $t_R$=0.79 min, [M+1]$^+$=370.06) is dissolved in dioxane (50 mL) and heated to 100° C. for 4 h. The solvent is evaporated and the crude product is purified by CC on silica gel eluting with heptane:EA 9:1 to give 2-ethyl-4-[5-(2-isobutyl-6-methyl-pyridin-4-yl)-[1,2,4]oxadiazol-3-yl]-6-methyl-phenol (1.97 g) as a colourless oil; LC-MS: $t_R$=0.93 min; [M+1]$^+$=352.16; $^1$H NMR (CDCl$_3$): δ 7.85 (s, 2 H), 7.75 (s, 1 H), 7.70 (s, 1 H), 5.05 (s br, 1H), 2.78 (d, J=7.5 Hz, 2H), 2.74 (q, J=7.5 Hz, 2H), 2.69 (s, 3H), 2.37 8 s, 3H), 2.19 (hept, J=7.5 Hz, 1H), 1.34 (t, J=7.5 Hz, 3H), 1.00 (d, J=6.5 Hz, 6H).

Example 14

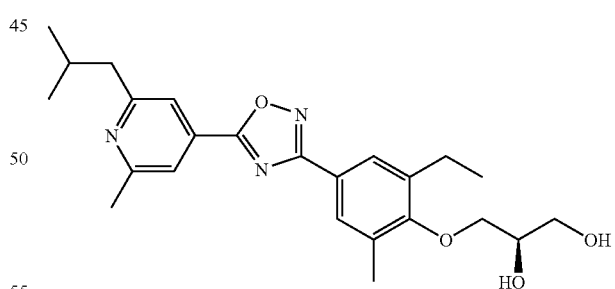

To a solution of 2-ethyl-4-[5-(2-isobutyl-6-methyl-pyridin-4-yl)-[1,2,4]oxadiazol-3-yl]-6-methyl-phenol (200 mg, 0.569 mmol) in isopropanol (10 mL) and 3 N aq. NaOH (3 mL), (R)-3-chloro-1,2-propanediol (252 mg, 2.28 mmol) is added. The mixture is stirred at 60° C. for 24 h before another portion of (R)-3-chloro-1,2-propanediol (252 mg, 2.28 mmol) is added. Stirring is continued at 60° C. for 6 days. The mixture is diluted with EA and washed with sat. aq. NaHCO$_3$ solution. The org. extract is dried over MgSO$_4$, filtered and evaporated. The crude product is purified by chromatography on prep. TLC plates with EA to give 3-{2-ethyl-4-[5-(2- isobutyl-6-methyl-pyridin-4-yl)-[1,2,4]oxadiazol-3-yl]-6-methyl-phenoxy}-(R)-propane-1,2-diol (40 mg) as a pale yellow oil; LC-MS: $t_R$=0.84 min; [M+1]$^+$=426.16; $^1$H NMR (CDCl$_3$): δ 7.90 (s, 1H), 7.88 (s, 1H), 7.76 (s, 1H), 7.70 (s, 1H), 4.20-4.14 (m, 1H), 3.95-3.85 (m, 4H), 2.80-2.74 (m, 4H), 2.70 (s, 3H), 2.42 (s, 3H), 2.24-2.16 (m, 1H), 1.34 (t, J=7.5 Hz, 3H), 1.00 (d, J=6.5 Hz, 6 H).

Example 15

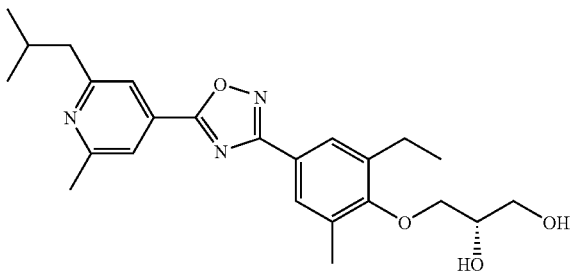

3-{2-Ethyl-4-[5-(2-isobutyl-6-methyl-pyridin-4-yl)-[1,2,4]oxadiazol-3-yl]-6-methyl-phenoxy}-(S)-propane-1,2-diol is prepared in analogy to Example 14 using (S)-3-chloro-1,2-propanediol as the alkylating agent; LC-MS: $t_R$=0.84 min, [M+1]$^+$=426.13.

Example 16

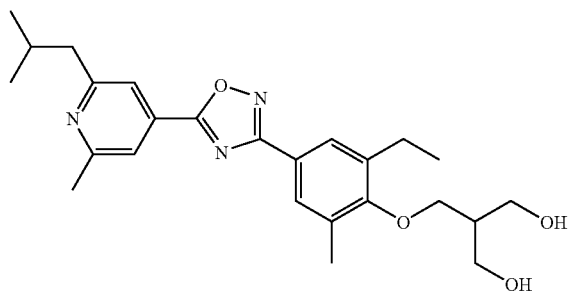 [SMILES: CCc1cc(-c2noc(-c3cc(C)nc(CC(C)C)c3)n2)cc(C)c1OCC(CO)CO]

To a solution of 2-ethyl-4-[5-(2-isobutyl-6-methyl-pyridin-4-yl)-[1,2,4]oxadiazol-3-yl]-6-methyl-phenol (200 mg, 0.569 mmol) in isopropanol (10 mL) and 3 N aq. NaOH (3 mL), methanesulfonic acid 2,2-dimethyl-[1,3]dioxan-5-ylmethyl ester (290 mg, 1.71 mmol) is added. The mixture is stirred at 60° C. for 24 h. The mixture is diluted with EA and washed with sat. aq. NaHCO$_3$ solution. The org. extract is dried over MgSO$_4$, filtered and evaporated. The crude product is purified by chromatography on prep. TLC plates with heptane:EA 3:1 to give 4-{3-[4-(2,2-dimethyl-[1,3]dioxan-5-ylmethoxy)-3-ethyl-5-methyl-phenyl]-[1,2,4]oxadiazol-5-yl}-2-isobutyl-6-methyl-pyridine which is dissolved in THF (5 mL), water (0.5 mL) and TFA (0.25 mL). The solution is stirred at rt for 1 h before the solvent is evaporated. The remaining residue is separated by chromatography on prep. TLC plates with DCM containing 10% of MeOH to give 2-{2-ethyl-4-[5-(2-isobutyl-6-methyl-pyridin-4-yl)-[1,2,4]oxadiazol-3-yl]-6-methyl-phenoxymethyl}-propane-1,3-diol (20 mg) as a colourless oil; LC-MS: $t_R$=0.86 min, [M+1]$^+$=440.12.

Examples 17 to 19

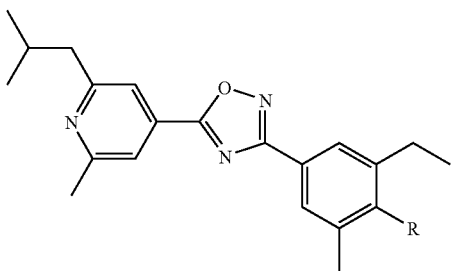

The following examples are prepared by alkylating 2-ethyl-4-[5-(2-isobutyl-6-methyl-pyridin-4-yl)-[1,2,4]oxadiazol-3-yl]-6-methyl-phenol in analogy to Example 14 with the appropriate alkylating agent.

| | | LC-MS | |
|---|---|---|---|
| Example | R | $t_R$ [min] | [M + H]$^+$ |
| 17 | ～O～OH | 0.91 | 396.18 |
| 18 | ～O～～OH | 0.94 | 410.14 |
| 19 | ～O～～N(CH$_3$)$_2$ | 0.78 | 423.26 |

Example 20

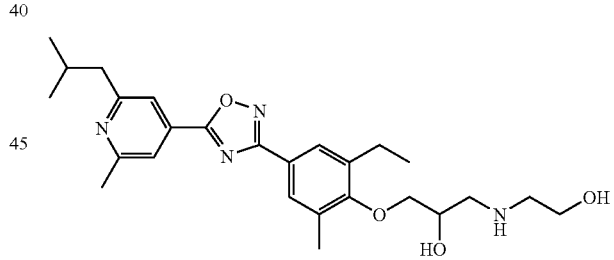

a) In analogy to Example 14, 2-ethyl-4-[5-(2-isobutyl-6-methyl-pyridin-4-yl)-[1,2,4]oxadiazol-3-yl]-6-methyl-phenol is alkylated with epichlorhydrine to give (RS)-4-[3-(3-ethyl-5-methyl-4-oxiranylmethoxy-phenyl)-[1,2,4]oxadiazol-5-yl]-2-isobutyl-6-methyl-pyridine as a colourless oil; LC-MS: $t_R$=1.00 min, [M+1]$^+$=408.18.

b) A solution of the above epoxide (60 mg, 0.147 mmol) and ethanolamine (36 mg, 0.589 mmol) in EtOH (5 mL) is stirred at 60° C. for 20 h. The mixture is diluted with EA and washed with sat. aq. NaHCO$_3$. The org. extract is evaporated and the residue is purified by chromatography on prep. TLC plates with DCM containing 5% of MeOH to give (RS)-1-{2-ethyl-4-[5-(2-isobutyl-6-methyl-pyridin-4-yl)-[1,2,4]oxadiazol-3-yl]-6-methyl-phenoxy}-3-(2-hydroxy-ethylamino)-propan-2-ol (61 mg) as a yellow solid; LC-MS: $t_R$=0.72 min, [M+1]$^+$=469.64.

Example 21

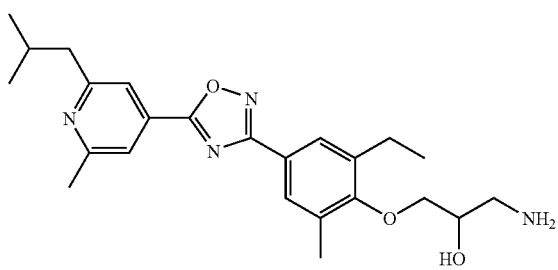

(RS)-1-Amino-3-{2-ethyl-4-[5-(2-isobutyl-6-methyl-pyridin-4-yl)-[1,2,4]oxadiazol-3-yl]-6-methyl-phenoxy}-propan-2-ol is prepared in analogy to Example 2; LC-MS: $t_R$=0.74 min, [M+1]$^+$=425.21.

Example 22

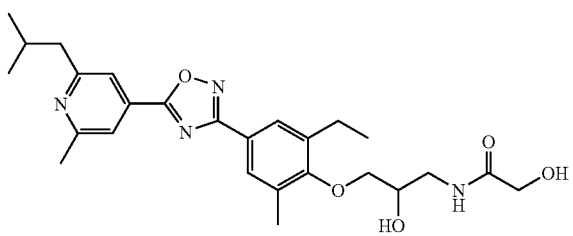 [SMILES: CCc1cc(-c2noc(-c3cc(C)nc(CC(C)C)c3)n2)cc(C)c1OCC(O)CNC(=O)CO]

N-((RS)-3-{2-Ethyl-4-[5-(2-isobutyl-6-methyl-pyridin-4-yl)-[1,2,4]oxadiazol-3-yl]-6-methyl-phenoxy}-2-hydroxypropyl)-2-hydroxy-acetamide is prepared from Example 21 in analogy to Example 3; LC-MS: $t_R$=0.81 min, [M+1]$^+$=483.21;

Example 23

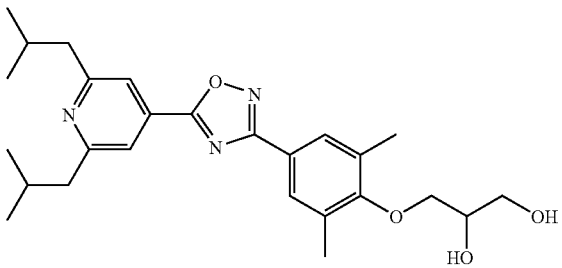 [SMILES: Cc1cc(-c2noc(-c3cc(CC(C)C)nc(CC(C)C)c3)n2)cc(C)c1OCC(O)CO]

(RS)-3-{4-[5-(2,6-Diisobutyl-pyridin-4-yl)-[1,2,4]oxadiazol-3-yl]-2,6-dimethyl-phenoxy}-propane-1,2-diol is prepared in analogy to Example 1; LC-MS: $t_R$=0.93 min, [M+1]$^+$=454.21.

Example 24

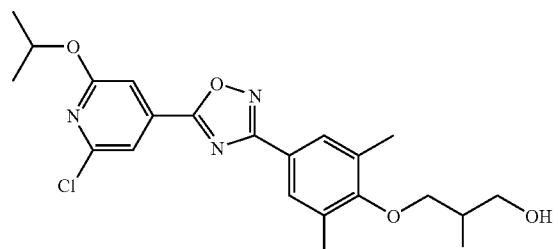

(RS)-3-{4-[5-(2-Chloro-6-isopropoxy-pyridin-4-yl)-[1,2,4]oxadiazol-3-yl]-2,6-dimethyl-phenoxy}-propane-1,2-diol is prepared in analogy to Example 1; LC-MS: $t_R$=1.12 min, [M+1]$^+$=434.46.

Example 25

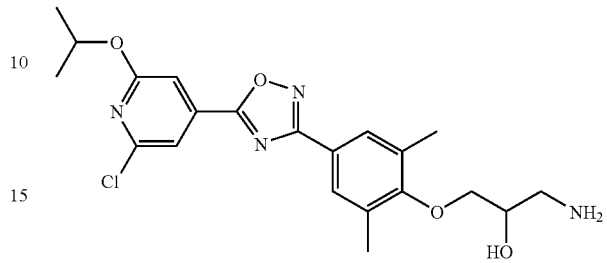

(RS)-1-Amino-3-{4-[5-(2-chloro-6-isopropoxy-pyridin-4-yl)-[1,2,4]oxadiazol-3-yl]-2,6-dimethyl-phenoxy}-propan-2-ol is prepared in analogy to Example 2; LC-MS: $t_R$=0.94 min, [M+1]$^+$=433.36.

Example 26

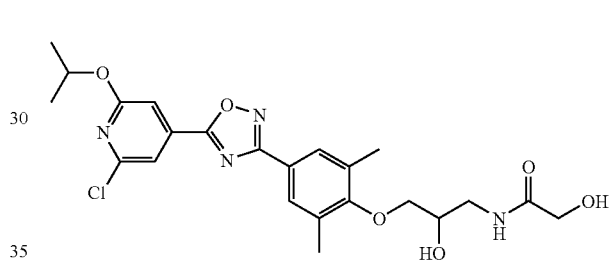

N-((RS)-3-{4-[5-(2-Chloro-6-isopropoxy-pyridin-4-yl)-[1,2,4]oxadiazol-3-yl]-2,6-dimethyl-phenoxy}-2-hydroxypropyl)-2-hydroxy-acetamide is prepared in analogy to Example 3; LC-MS: $t_R$=1.04 min; [M+1]$^+$=491.18; $^1$H NMR (CD$_3$OD): δ 7.76 (s, 2H), 7.58 (d, J=1.0 Hz, 1H), 7.31 (d, J=1.0 Hz, 1H), 5.33 (hept, J=6.3 Hz, 1H), 4.16-4.10 (m, 1H), 4.04 (s, 2H), 3.90-3.82 (m, 2H), 3.66 (dd, J=13.6, 4.8 Hz, 1H), 3.46 (dd, J=13.6, 7.0 Hz, 1H), 2.37 (s, 6H), 1.40 (t, J=6.0 Hz, 6H).

Example 27

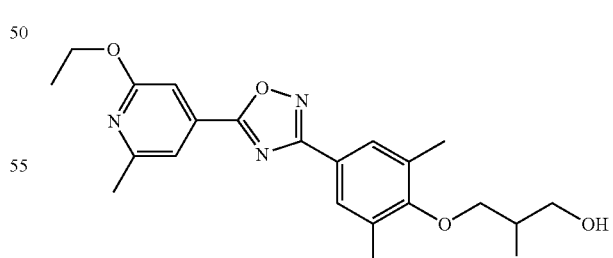

(RS)-3-{4-[5-(2-Ethoxy-6-methyl-pyridin-4-yl)-[1,2,4]oxadiazol-3-yl]-2,6-dimethyl-phenoxy}-propane-1,2-diol is prepared in analogy to Example 1; LC-MS: $t_R$=1.03 min, [M+1]$^+$=400.48, $^1$H NMR (CDCl$_3$): 7.85 (s, 2H), 7.47 (s, 1H), 7.29 (s, 1H), 4.65 (s br, 2H), 4.43 (q, J=7.0 Hz, 2H), 4.19-4.13 (m, 1H), 3.96-3.82 (m, 4H), 2.57 (s, 3H), 2.39 (s, 6H), 1.45 (t, J=7.0 Hz, 3H).

Example 28

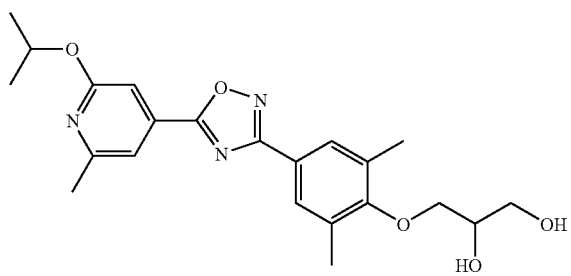

(RS)-3-{4-[5-(2-Isopropoxy-6-methyl-pyridin-4-yl)-[1,2,4]oxadiazol-3-yl]-2,6-dimethyl-phenoxy}-propane-1,2-diol is prepared in analogy to Example 1; LC-MS: $t_R$=1.05 min, [M+1]$^+$=414.04.

Example 29

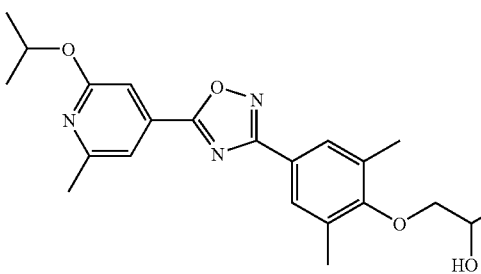

(RS)-1-Amino-3-{4-[5-(2-isopropoxy-6-methyl-pyridin-4-yl)-[1,2,4]oxadiazol-3-yl]-2,6-dimethyl-phenoxy}-propan-2-ol is prepared in analogy to Example 2; LC-MS: $t_R$=0.87 min, [M+1]$^+$=413.10.

Example 30

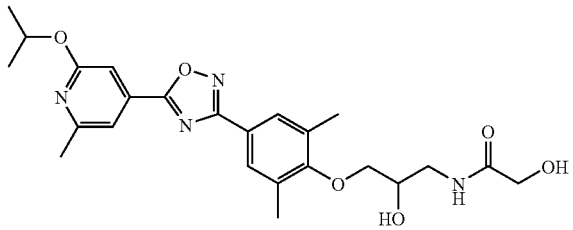 [SMILES: Cc1cc(-c2noc(-c3cc(Cl)nc(OC(C)C)c3)n2)cc(C)c1OCC(O)CNC(=O)CO]

2-Hydroxy-N-((RS)-2-hydroxy-3-{4-[5-(2-isopropoxy-6-methyl-pyridin-4-yl)-[1,2,4]oxadiazol-3-yl]-2,6-dimethyl-phenoxy}-propyl)-acetamide is prepared in analogy to Example 3; LC-MS: $t_R$=1.00 min; [M+1]$^+$=471.21; $^1$H NMR (CD$_3$OD): δ 7.80 (s, 2H), 7.46 (s, 1H), 7.19 (s, 1H), 5.37 (hept, J=6.5 Hz, 1H), 4.17-4.10 (m, 1H), 4.04 (s, 2H), 3.91-3.84 (m, 2H), 3.66 (dd, J=13.8, 4.5 Hz, 1H), 3.47 (dd, J=13.6, 7.0 Hz, 1H), 2.54 (s, 3H), 2.38 (s, 6H), 1.39 (d, J=6.9 Hz, 6H).

Examples 31 to 36

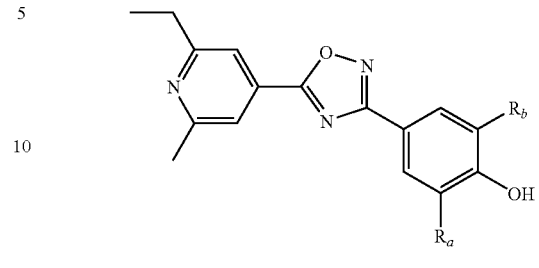

The following Examples are prepared in analogy to Example 10 starting from isonicotinic acid 4 and the appropriate N-hydroxybenzamidines.

| | | | LC-MS | |
|---|---|---|---|---|
| Example | $R_a$ | $R_b$ | $t_R$ [min] | [M + H]$^+$ |
| 31 | CH$_3$ | CH$_3$ | 0.83 | 310.11 |
| 32 | CH$_3$ | CH$_2$CH$_3$ | 0.86 | 324.44 |
| 33 | CH$_3$ | CH$_2$CH$_2$CH$_3$ | 0.90 | 338.10 |
| 34 | CH$_3$ | Cl | 0.63* | 329.83 |
| 35 | Cl | OCH$_3$ | 0.82 | 346.02 |
| 36 | CH$_3$ | OCH$_3$ | 0.82 | 326.08 |

Example 34

$^1$H NMR (CDCl$_3$): δ1.39 (t, J=7.5 Hz, 3 H), 2.39 (s, 3 H), 2.68 (s, 3 H), 2.94 (q, J=7.5 Hz, 2 H), 6.20 (s br, 1 H), 7.73 (s, 2 H), 7.89 (s, 1 H), 8.03 (s, 1 H).

Example 37 to 44

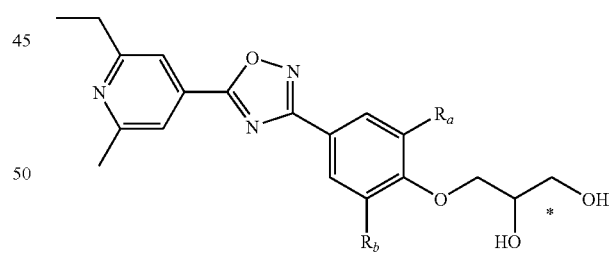

The following Examples are prepared in analogy to Example 14 using either (R)- or (S)-3-chloro-1,2-propanediol.

| | | | | LC-MS | |
|---|---|---|---|---|---|
| Example | $R_a$ | $R_b$ | *Chirality | $t_R$ [min] | [M + H]$^+$ |
| 37 | CH$_3$ | CH$_3$ | R | 0.86* | 384.24 |
| 38 | CH$_3$ | CH$_2$CH$_3$ | R | 0.90* | 398.22 |
| 39 | CH$_3$ | Cl | R | 0.77 | 404.05 |

-continued

| Example | $R_a$ | $R_b$ | *Chirality | LC-MS $t_R$ [min] | [M + H]$^+$ |
|---|---|---|---|---|---|
| 40 | Cl | OCH$_3$ | R | 0.75 | 420.09 |
| 41 | CH$_3$ | CH$_3$ | S | 0.87* | 384.23 |
| 42 | CH$_3$ | CH$_2$CH$_3$ | S | 0.90* | 398.22 |
| 43 | CH$_3$ | Cl | S | 0.77 | 404.05 |
| 44 | Cl | OCH$_3$ | S | 0.76 | 420.06 |

Example 44

$^1$H NMR (D$_6$-DMSO): δ1.29 (t, J=7.3 Hz, 3 H), 2.60 (s, 3 H), 2.88 (q, J=7.3 Hz, 2 H), 3.42-3.56 (m, 2 H), 3.78-3.85 (m, 1 H), 3.97 (s, 3 H), 3.99-4.10 (m, 2 H), 4.60 (t br, J=5.5 Hz), 4.85 (d br, J=4.0 Hz), 7.65 (s, 1 H), 7.74 (s, 1 H), 7.80 (s, 1 H), 7.82 (s, 1 H).

Examples 45

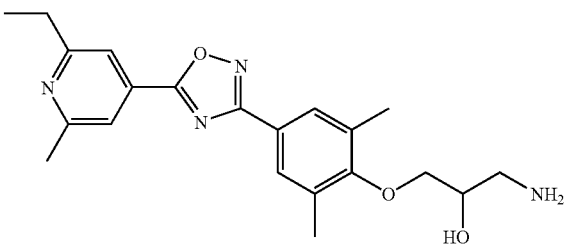 [SMILES: CCc1cc(-c2nc(-c3cc(C)c(OCC(O)CN)c(C)c3)no2)cc(C)n1]

(RS)-1-Amino-3-{4-[5-(2-ethyl-6-methyl-pyridin-4-yl)-[1,2,4]oxadiazol-3-yl]-2,6-dimethyl-phenoxy}-propan-2-ol is prepared in analogy to Example 2 starting from isonicotinic acid 4 and 4-allyloxy-N-hydroxy-3,5-dimethyl-benzamidine; LC-MS: $t_R$=0.65 min.

Example 46

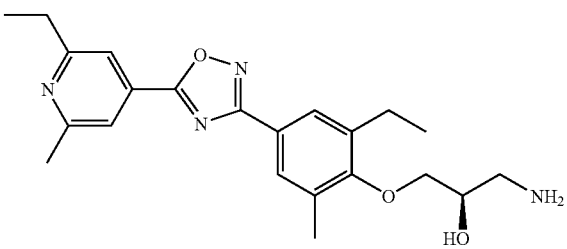 [SMILES: CCc1cc(-c2nc(-c3cc(C)c(OC[C@H](O)CN)c(CC)c3)no2)cc(C)n1]

a) To a solution of 2-ethyl-4-[5-(2-ethyl-6-methyl-pyridin-4-yl)-[1,2,4]oxadiazol-3-yl]-6-methyl-phenol (150 mg, 0.464 mmol) in THF (10 mL), PPh$_3$ (146 mg, 0.557 mmol) and (S)-glycidol (52 mg, 0.696 mmol) is added. The mixture is cooled to 0° C. before DEAD (303 mg, 0.696 mmol, 320 µL of a 40% solution in toluene) is added. The mixture is warmed to rt and stirred for 1 h. The solvent is evaporated and the residue is purified by chromatography on prep. TLC plates with heptane:EA 1:1 to give (R)-2-ethyl-4-[3-(3-ethyl-5-methyl-4-oxiranylmethoxy-phenyl)-[1,2,4]oxadiazol-5-yl]-6-methyl-pyridine (201 mg) as a white solid; LC-MS*: $t_R$=1.10* min; [M+1]$^+$=380.42.

b) A solution of (R)-2-ethyl-4-[3-(3-ethyl-5-methyl-4-oxiranylmethoxy-phenyl)-[1,2,4]oxadiazol-5-yl]-6-methyl-pyridine (201 mg, 0.531 mmol) in 7 N NH$_3$ in MeOH (20 mL) is stirred at 65° C. for 24 h. The solvent is evaporated and the residue is dried under HV to give (R)-1-amino-3-{2-ethyl-4-[5-(2-ethyl-6-methyl-pyridin-4-yl)-[1,2,4]oxadiazol-3-yl]-6-methyl-phenoxy}-propan-2-ol (183 mg) as a pale yellow oil; LC-MS: $t_R$=0.69 min; [M+1]$^+$=397.18.

Example 47

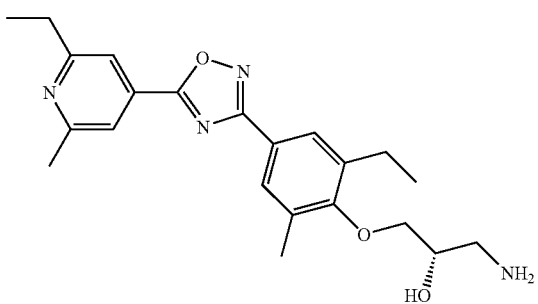 [SMILES: CCc1cc(-c2nc(-c3cc(C)c(OC[C@@H](O)CN)c(CC)c3)no2)cc(C)n1]

a) To a solution of 2-ethyl-4-[5-(2-ethyl-6-methyl-pyridin-4-yl)-[1,2,4]oxadiazol-3-yl]-6-methyl-phenol (89 mg, 0.276 mmol) in 3 N aq. NaOH (1 mL) and isopropanol (4 mL), (R)-epichlorohydrine (142 mg, 1.53 mmol) is added. The mixture is stirred at rt for 24 h before another portion of (R)-epichlorohydrine (142 mg; 1.53 mmol) is added. Stirring is continued for another 24 h at rt. The mixture is diluted with EA (50 mL) and washed with 1M aq. NaOH (10 mL) and brine (10 mL). The org. phase is dried over MgSO$_4$, filtered and evaporated to give crude (S)-2-ethyl-4-[3-(3-ethyl-5-methyl-4-oxiranylmethoxy-phenyl)-[1,2,4]oxadiazol-5-yl]-6-methyl-pyridine; LC-MS*: $t_R$=1.11* min; [M+1]$^+$=380.24.

b) (S)-2-ethyl-4-[3-(3-ethyl-5-methyl-4-oxiranylmethoxy-phenyl)-[1,2,4]oxadiazol-5-yl]-6-methyl-pyridine is treated with ammonia in MeOH as described in Example 46 step b) to give (R)-1-amino-3-{2-ethyl-4-[5-(2-ethyl-6-methyl-pyridin-4-yl)-[1,2,4]oxadiazol-3-yl]-6-methyl-phenoxy}-propan-2-ol.

Examples 48 to 54

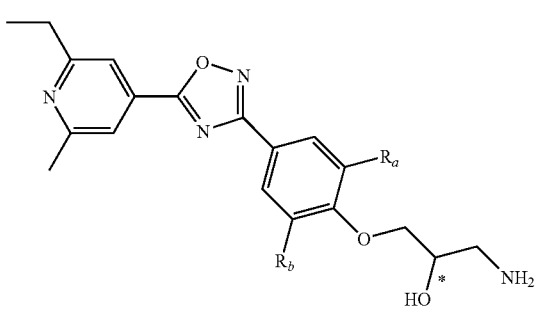

The following Examples are prepared in analogy to Example 46 or 47.

| Example | $R_a$ | $R_b$ | *Chirality | LC-MS $t_R$ [min] | $[M + H]^+$ |
|---|---|---|---|---|---|
| 48 | $CH_3$ | $CH_2CH_2CH_3$ | rac | 0.71 | 411.07 |
| 49 | $CH_3$ | $CH_2CH_2CH_3$ | S | 1.17* | 411.14 |
| 50 | $CH_3$ | Cl | R | | |
| 51 | $CH_3$ | Cl | S | | |
| 52 | Cl | $OCH_3$ | R | 0.68 | 418.95 |
| 53 | Cl | $OCH_3$ | S | 0.67 | 418.99 |
| 54 | $CH_3$ | $OCH_3$ | rac | 0.66 | 399.10 |

Example 52

$^1$H NMR (CDCl$_3$): δ1.40 (t, J=7.5 Hz, 3 H), 2.70 (s, 3 H), 2.91-3.01 (m, 4 H), 3.94-4.00 (m, 1H), 4.02 (s, 3 H), 4.05-4.18 (m, 1H), 4.24-4.31 (m, 1 H), 7.65 (s, 1 H), 7.75 (s, 2 H), 7.89 (s, 1 H).

Examples 55 to 64

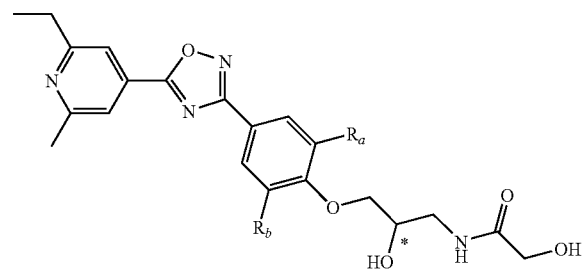

The following Examples are prepared in analogy to Example 3 by treating the corresponding amines with glycolic acid.

| Example | $R_a$ | $R_b$ | *Chirality | LC-MS $t_R$ [min] | $[M + H]^+$ |
|---|---|---|---|---|---|
| 55 | $CH_3$ | $CH_3$ | rac | 0.80* | 441.18 |
| 56 | $CH_3$ | $CH_2CH_3$ | R | 0.74 | 455.23 |
| 57 | $CH_3$ | $CH_2CH_3$ | S | 0.84* | 455.21 |
| 58 | $CH_3$ | $CH_2CH_2CH_3$ | rac | 0.78 | 469.20 |
| 59 | $CH_3$ | $CH_2CH_2CH_3$ | S | 0.85* | 469.18 |
| 60 | $CH_3$ | Cl | R | 0.74 | 461.13 |
| 61 | $CH_3$ | Cl | S | 0.74 | 461.13 |
| 62 | $CH_3$ | $OCH_3$ | R | 0.74 | 477.17 |
| 63 | Cl | $OCH_3$ | S | 0.74 | 477.19 |
| 64 | $CH_3$ | $OCH_3$ | rac | 0.71 | 457.18 |

Example 57

$^1$H NMR (D$_6$-DMSO): δ 1.19-1.32 (m, 6 H), 2.35 (s, 3H), 2.60 (s, 3 H), 2.73 (q, J=7.3 Hz, 2H), 2.87 (q, J=7.5 Hz, 2 H), 3.20-3.29 (m, 1 H), 3.39-3.48 (m, 1 H), 3.70-3.80 (m, 2 H), 3.84 (d, J=5.5 Hz, 2 H), 3.93-4.00 (m, 1 H), 5.31 (d, J=5.0 Hz, 1 H), 5.55 (t, J=5.8 Hz, 1 H), 7.70 (t br, J=5.5 Hz, 1 H), 7.77 (s, 1 H), 7.80 (s, 3 H).

Example 65

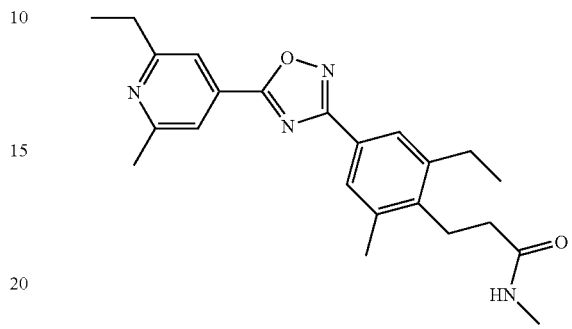

To a solution of 3-{2-ethyl-4-[5-(2-ethyl-6-methyl-pyridin-4-yl)-[1,2,4]oxadiazol-3-yl]-6-methyl-phenyl}-propionic acid (26 mg, 69 μmol) and DIPEA (27 mg, 207 μmol) in DMF (3 mL) is added PyBOP (40 mg, 76 μmol) at 0° C. The mixture is stirred for 15 min at 0° C. before methylamine (2.4 mg, 76 μmol, 38 μL of a 2 M solution in THF) is added. Stirring is continued for 1 h at 0° C. The reaction is quenched with water (2 mL), and the mixture is diluted with sat. aq. NaHCO$_3$ solution. The mixture is extracted twice with ether. The combined org. extracts are dried over MgSO$_4$, filtered and concentrated. The crude product is purified on prep. TLC plates with heptane:EA 1:4 to give 3-{2-ethyl-4-[5-(2-ethyl-6-methyl-pyridin-4-yl)-[1,2,4]oxadiazol-3-yl]-6-methyl-phenyl}-N-methyl-propionamide (21 mg) as a white solid; LC-MS: $t_R$=0.90 min; [M+1]$^+$=393.45; $^1$H NMR δ 1.32 (t, J=7.5 Hz, 3 H), 1.40 (t, J=7.8 Hz, 3 H), 2.34-2.41 (m, 2 H), 2.45 (s, 3 H), 2.69 (s, 3 H), 2.77 (q, J=7.5 Hz, 2 H), 2.85 (d, J=4.8 Hz, 3 H), 2.95 (q, J=7.8 Hz, 2 H), 3.07-3.13 (m, 2H), 5.41 (s br, 1 H), 7.76 (s, 2 H), 7.84 (s, 1 H), 7.86 (s, 1 H).

Example 66

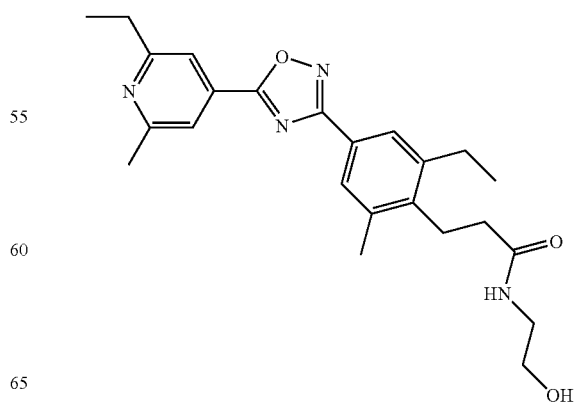

3-{2-Ethyl-4-[5-(2-ethyl-6-methyl-pyridin-4-yl)-[1,2,4]oxadiazol-3-yl]-6-methyl-phenyl}-N-(2-hydroxy-ethyl)-propionamide is prepared in analogy to Example 65 using ethanolamine; LC-MS: $t_R$=0.83 min; [M+1]$^+$=423.36.

Example 67

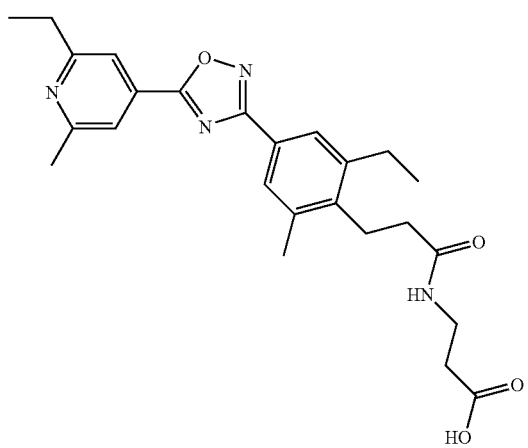 [SMILES: CCc1cc(-c2nc(-c3cc(C)c(CCC(=O)NCCC(=O)O)c(CC)c3)no2)cc(C)n1]

3-(3-{2-Ethyl-4-[5-(2-ethyl-6-methyl-pyridin-4-yl)-[1,2,4]oxadiazol-3-yl]-6-methyl-phenyl}-propionylamino)-propionic acid is obtained by coupling 3-{2-ethyl-4-[5-(2-ethyl-6-methyl-pyridin-4-yl)-[1,2,4]oxadiazol-3-yl]-6-methyl-phenyl}-propionic acid with 3-amino-propionic acid tert-butyl ester in analogy to Example 65, followed by cleaving the tert-butyl ester with 4 N HCl in dioxane at rt; LC-MS: $t_R$=0.80 min; [M+1]$^+$=451.20.

Example 68

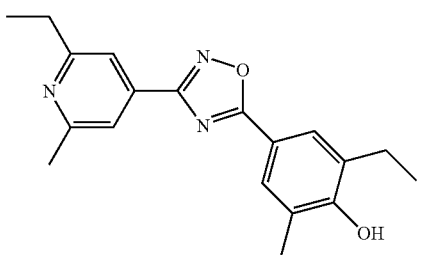 [SMILES: CCc1cc(-c2noc(-c3cc(C)c(O)c(CC)c3)n2)cc(C)n1]

2-Ethyl-4-[3-(2-ethyl-6-methyl-pyridin-4-yl)-[1,2,4]oxadiazol-5-yl]-6-methyl-phenol is prepared in analogy to Example 10 by coupling and cyclising 2-ethyl-N-hydroxy-6-methyl-isonicotinamidine with 3-ethyl-4-hydroxy-5-methyl-benzoic acid; LC-MS: $t_R$=0.83 min; [M+1]$^+$=324.15.

Examples 69 to 74

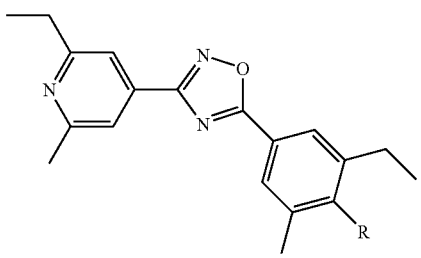

The following examples are prepared in analogy to previous examples starting from 2-ethyl-4-[3-(2-ethyl-6-methyl-pyridin-4-yl)-[1,2,4]oxadiazol-5-yl]-6-methyl-phenol.

| | in analogy to | | LC-MS | |
| --- | --- | --- | --- | --- |
| Example | Example | R | $t_R$ [min] | [M + H]$^+$ |
| 69 | 14 | ![O-CH2-CH(OH)-CH2OH] | 0.75 | 398.17 |
| 70 | 14 | ![O-CH2-CH(OH)-CH2OH stereo] | 0.75 | 398.18 |
| 71 | 47 | ![O-CH2-CH(OH)-CH2NH2] | 0.66 | 397.19 |
| 72 | 47 | ![O-CH2-CH(OH)-CH2NH2 stereo] | 0.66 | 397.18 |
| 73 | 3 | ![O-CH2-CH(OH)-CH2-NH-C(O)-CH2OH] | 0.73 | 455.24 |

-continued

| | in analogy to | | | LC-MS | |
|---|---|---|---|---|---|
| Example | Example | R | | $t_R$ [min] | $[M + H]^+$ |
| 74 | 3 | 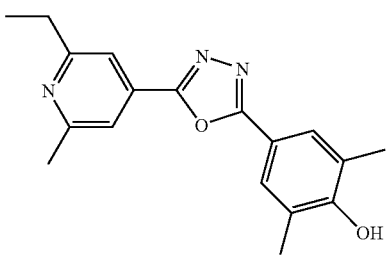 | | 0.73 | 455.25 |

Example 74

$^1$H NMR (D$_6$-DMSO): δ 1.24 (t, J=8.0 Hz, 3H), 1.28 (t, J=7.5 Hz, 3H), 2.37 (s, 3 H), 2.58 (s, 3 H), 2.76 (q, J=7.5 Hz, 2 H), 2.84 (q, J=7.5 Hz, 2 H), 3.19-3.30 (m, 1 H), 3.39-3.48 (m, 1 H), 3.73-3.82 (m, 2 H), 3.84 (d, J=5.5 Hz, 2 H), 3.93-4.01 (m, 1 H), 5.32 (d, J=5.3 Hz, 1 H), 5.54 (t, J=5.5 Hz, 1 H), 7.66-7.73 (m, 3 H), 7.92 (s, 2 H).

Example 75

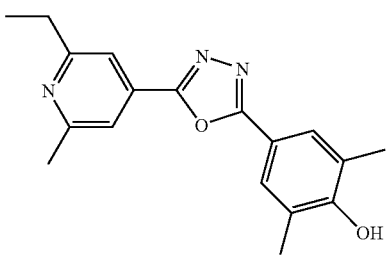 [SMILES: CCc1cc(-c2nnc(-c3cc(C)c(O)c(C)c3)o2)cc(C)n1]

To a solution of isonicotinic acid 4 (150 mg, 0.744 mmol), 4-benzyloxy-3,5-dimethyl-benzoic acid hydrazide (200 mg, 0.740 mmol) and DIPEA (302 mg, 2.34 mmol) in DCM (15 mL) PyBOP (420 mg, 0.807 mmol) is added portionwise at 0° C. The mixture is stirred at 0° C. for 3 h before pyridine (295 mg, 3.73 mmol) followed by trifluoromethanosulfonic acid anhydride (214 mg, 1.17 mmol) is added. The mixture is stirred at rt for 15 h before another portion of pyridine (295 mg, 3.73 mmol) and trifluoromethanosulfonic acid anhydride (214 mg, 1.17 mmol) is added. After stirring for 2 h yet another portion of pyridine (295 mg, 3.73 mmol) and trifluoromethanosulfonic acid anhydride (214 mg, 1.17 mmol) is added and stirring is continued for 2 h. Dimethylaminopropylamine (0.25 mL) is added and the mixture is stirred for 30 min before it is diluted with ether (100 mL), washed with 1 M aq. NaH$_2$PO$_4$ solution (2×30 mL) and sat. aq. Na$_2$CO$_3$ solution. The washings are extracted back with EA (2×75 mL). The combined org. extracts are dried over MgSO$_4$, filtered and evaporated to give crude 4-[5-(4-benzyloxy-3,5-dimethyl-phenyl)-[1,3,4]oxadiazol-2-yl]-2-ethyl-6-methyl-pyridine; LC-MS: $t_R$=1.12 min; [M+1]$^+$=400.22. To a solution of this material in formic acid (0.125 mL), MeOH (5 mL) and THF (10 mL), Pd/C (50 mg, 10% Pd) is added and the mixture is stirred at rt under 1 bar of H$_2$ for 15 h. The catalyst is removed by filtration and the solvent of the filtrate is evaporated. The residue is dissolved in EA (100 mL), washed with sat. aq. NaHCO$_3$ solution, dried over MgSO$_4$, filtered and concentrated. The crude product is purified by CC on silica gel eluting with EA to give 4-[5-(2-ethyl-6-methyl-pyridin-4-yl)-[1,3,4]oxadiazol-2-yl]-2,6-dimethyl-phenol (209 mg) as a beige foam; LC-MS: $t_R$=0.74 min; [M+1]$^+$=310.11.

Example 76

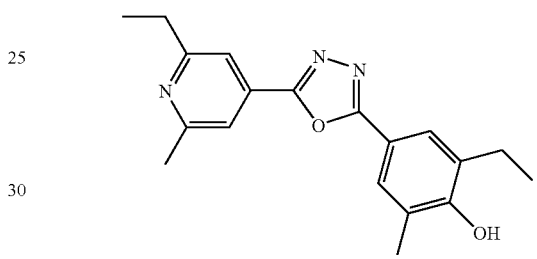

2-Ethyl-4-[5-(2-ethyl-6-methyl-pyridin-4-yl)-[1,3,4]oxadiazol-2-yl]-6-methyl-phenol is prepared in analogy to Example 75 starting from isonicotinic acid 4 and 4-benzyloxy-3-ethyl-5-methyl-benzoic acid hydrazide; LC-MS: $t_R$=0.74 min; [M+1]$^+$=324.27; $^1$H NMR (D$_6$-DMSO): δ 1.19 (t, J=7.3 Hz, 3 H), 1.27 (t, J=7.5 Hz, 3 H), 2.27 (s, 3 H), 2.55 (s, 3 H), 2.68 (q, J=7.5 Hz, 2 H), 2.82 (q, J=7.5 Hz, 2 H), 7.67 (s, 1H), 7.69 (s, 1 H), 7.72 (s, 2 H), 9.15 (s, 1 H).

Examples 77 to 84

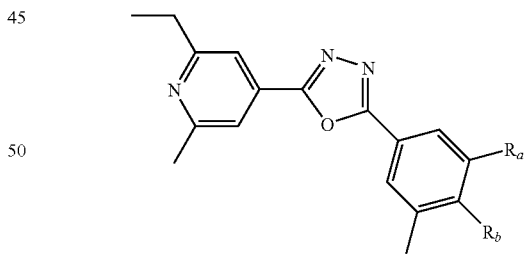

The following examples are prepared in analogy to previous examples starting from Example 75 or 76.

| | in analogy to | | | LC-MS | |
|---|---|---|---|---|---|
| Example | Example | $R_a$ | $R_b$ | $t_R$ [min] | $[M + H]^+$ |
| 77 | 14 | CH$_3$ | 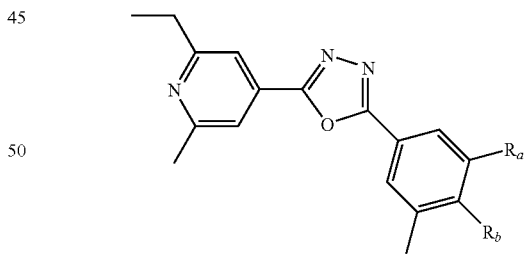 | 0.76 | 384.23 |

-continued

| Example | in analogy to Example | $R_a$ | $R_b$ | LC-MS $t_R$ [min] | $[M + H]^+$ |
|---|---|---|---|---|---|
| 78 | 14 | $CH_3$ | (structure: O-CH2-CH(OH)-CH2-OH) | 0.76 | 384.24 |
| 79 | 47 | $CH_3$ | (structure: O-CH2-CH(OH)-CH2-NH2) | 0.60 | |
| 80 | 3 | $CH_3$ | (structure: O-CH2-CH(OH)-CH2-NH-C(=O)-CH2-OH) | 0.69* | 441.22 |
| 81 | 47 | $CH_2CH_3$ | (structure: O-CH2-CH(OH)-CH2-NH2) | | |
| 82 | 3 | $CH_2CH_3$ | (structure: O-CH2-CH(OH)-CH2-NH-C(=O)-CH2-OH) | 0.75* | 455.23 |
| 83 | 47 | $CH_2CH_3$ | (structure: O-CH2-CH(OH)-CH2-NH2) | | |
| 84 | 3 | $CH_2CH_3$ | (structure: O-CH2-CH(OH)-CH2-NH-C(=O)-CH2-OH) | 0.75* | 455.17 |

Example 79

$^1$H NMR δ 1.39 (t, J=7.8 Hz, 3 H), 2.41 (s, 6 H), 2.67 (s, 3 H), 2.93 (q, J=7.8 Hz, 2 H), 2.96-3.02 (m, 1 H), 3.06-3.13 (m, 1 H), 3.88-3.91 (m, 2 H), 4.04-4.09 (m, 1 H), 7.67 (s, 1 H), 7.83 (s, 2 H).

Example 84

$^1$H NMR (D$_6$-DMSO): δ 1.19-1.32 (m, 6 H), 2.37 (s, 3 H), 2.60 (s, 3 H), 2.75 (q, J=7.3 Hz, 2H), 2.87 (q, J=7.5 Hz, 2 H), 3.10-3.19 (m, 1 H), 3.57-3.67 (m, 1 H), 3.70-3.82 (m, 2 H), 3.84 (s, 2 H), 3.92-4.01 (m, 1 H), 7.70 (t, J=5.5 Hz, 1 H), 7.78 (s, 1 H), 7.81 (s, 1 H), 7.88 (s, 2 H).

Examples 85-105

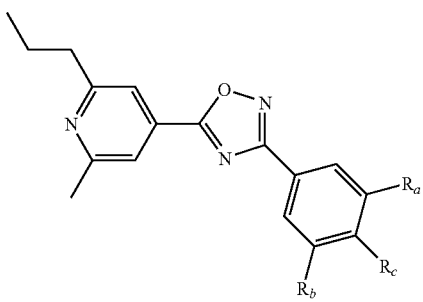

The following Examples are prepared in analogy to previous Examples starting from isonicotinic acid 5.

| Example | in analogy to Example | $R_a$ | $R_b$ | $R_c$ | LC-MS $t_R$ [min] | $[M + H]^+$ |
|---|---|---|---|---|---|---|
| 85 | 10 | $CH_3$ | $CH_3$ | OH | 0.86 | 323.95 |
| 86 | 10 | $CH_3$ | $CH_2CH_3$ | OH | 0.90 | 338.27 |
| 87 | 10 | Cl | $OCH_3$ | OH | 0.60* | 360.37 |

-continued
| Example | in analogy to Example | $R_a$ | $R_b$ | $R_c$ | LC-MS $t_R$ [min] | $[M + H]^+$ |
|---|---|---|---|---|---|---|
| 88 | 14 | $CH_3$ | $CH_3$ | 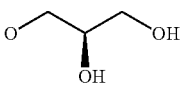 | 0.91* | 398.23 |
| 89 | 14 | $CH_3$ | $CH_3$ | 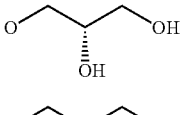 | 0.92* | 398.27 |
| 90 | 14 | $CH_3$ | $CH_2CH_3$ | 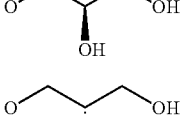 | 0.95* | 412.23 |
| 91 | 14 | $CH_3$ | $CH_2CH_3$ | 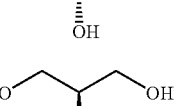 | 0.95* | 412.22 |
| 92 | 14 | Cl | $OCH_3$ | 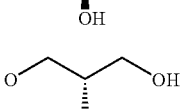 | 0.79 | 434.08 |
| 93 | 14 | Cl | $OCH_3$ | 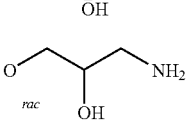 | 0.79 | 434.08 |
| 94 | 47 | $CH_3$ | $CH_3$ | 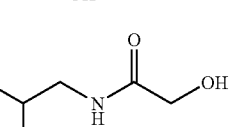 | 0.69 | 397.13 |
| 95 | 3 | $CH_3$ | $CH_3$ |  | 0.83 | 455.21 |
| 96 | 47 | $CH_3$ | $CH_3$ | 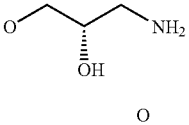 | 0.68 | 397.13 |
| 97 | 3 | $CH_3$ | $CH_3$ | 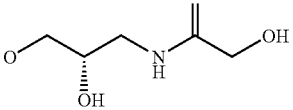 | 0.82* | 455.27 |
| 98 | 47 | $CH_3$ | $CH_2CH_3$ | 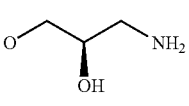 | 0.71 | 411.08 |
| 99 | 3 | $CH_3$ | $CH_2CH_3$ | 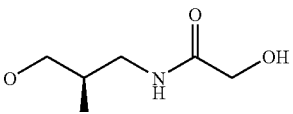 | 0.86* | 469.22 |
| 100 | 47 | $CH_3$ | $CH_2CH_3$ | 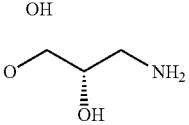 | 0.71 | 411.07 |
| 101 | 3 | $CH_3$ | $CH_2CH_3$ | 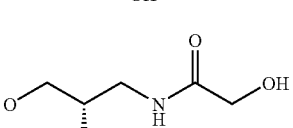 | 0.86* | 469.24 |

-continued

| Example | in analogy to Example | $R_a$ | $R_b$ | $R_c$ | LC-MS $t_R$ [min] | $[M + H]^+$ |
|---------|----------------------|-------|-------|-------|-------------------|-------------|
| 102 | 47 | Cl | OCH₃ | ![structure with O-CH2-CH(OH)-CH2-NH2] | 0.99* | 433.31 |
| 103 | 3 | Cl | OCH₃ | ![structure with O-CH2-CH(OH)-CH2-NH-C(O)-CH2OH] | 0.83* | 491.27 |
| 104 | 47 | Cl | OCH₃ | ![structure with O-CH2-CH(OH)-CH2-NH2, stereo] | 0.70 | 433.16 |
| 105 | 3 | Cl | OCH₃ | ![structure with O-CH2-CH(OH)-CH2-NH-C(O)-CH2OH, stereo] | 0.83* | 491.19 |

Example 87

¹H NMR (D₆-DMSO): δ 0.94 (t, J=7.3 Hz, 3 H), 1.68-1.81 (m, 2 H), 2.60 (s, 3 H), 2.78-2.86 (m, 2 H), 3.94 (s, 3 H), 7.52 (s, 1 H), 7.68 (s, 1 H), 7.76 (s, 1 H), 7.80 (s, 1 H).

Example 89

¹H NMR δ 0.94 (t, J=7.5 Hz, 3 H), 1.68-1.80 (m, 2 H), 2.34 (s, 6H), 2.59 (s, 3 H), 2.81 (t, J=7.3 Hz, 2 H), 3.50 (t, J=5.3 Hz, 2 H), 3.72-3.78 (m, 1 H), 3.79-3.90 (m, 2H), 4.65 (t, J=5.8 Hz, 1 H), 4.97 (d, J=5.0 Hz, 1 H), 7.74 (s, 1 H), 7.77 (s, 3 H).

Example 103

¹H NMR (D₆-DMSO): δ 0.95 (t, J=7.3 Hz, 3 H), 1.70-1.79 (m, 2 H), 2.60 (s, 3 H), 2.80-2.86 (m, 2 H), 3.17-3.27 (m, 1 H), 3.44-3.53 (m, 1 H), 3.83 (d, J=5.0 Hz, 2 H), 3.88-3.95 (m, 2 H), 3.97 (s, 3 H), 3.99-4.05 (m, 1 H), 5.19 (d br, J=3.3 Hz, 1 H), 5.55 (t br, J=5.8 Hz, 1 H), 7.61-7.67 (m, 2 H), 7.75 (s, 1 H), 7.78 (s, 1 H), 7.82 (s, 1 H).

Examples 106 to 115

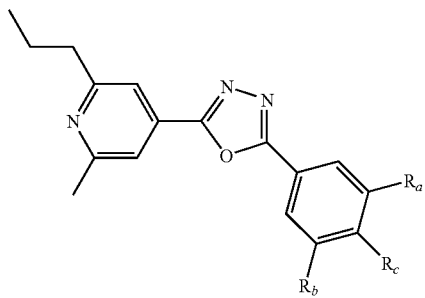

The following examples are prepared in analogy to previous examples starting from isonicotinic acid 5.

| Example | in analogy to Example | $R_a$ | $R_b$ | $R_c$ | LC-MS $t_R$ [min] | $[M + H]^+$ |
|---------|----------------------|-------|-------|-------|-------------------|-------------|
| 106 | 75 | CH₃ | CH₃ | OH | 0.77 | 324.14 |
| 107 | 75 | CH₃ | CH₂CH₃ | OH | 0.83* | 338.26 |
| 108 | 14 | CH₃ | CH₃ | ![O-CH2-CH(OH)-CH2-OH, stereo] | 0.80* | 398.21 |
| 109 | 14 | CH₃ | CH₃ | ![O-CH2-CH(OH)-CH2-OH, stereo] | 0.80* | 398.22 |
| 110 | 47 | CH₃ | CH₃ | ![O-CH2-CH(OH)-CH2-NH2, stereo] | 0.63 | 397.13 |

-continued

| | in analogy to | | | | LC-MS | |
|---|---|---|---|---|---|---|
| Example | Example | $R_a$ | $R_b$ | $R_c$ | $t_R$ [min] | $[M + H]^+$ |
| 111 | 3 | $CH_3$ | $CH_3$ | (structure) | 0.73* | 455.25 |
| 112 | 47 | $CH_3$ | $CH_2CH_3$ | (structure) | | |
| 113 | 3 | $CH_3$ | $CH_2CH_3$ | (structure) | 0.79* | 469.21 |
| 114 | 47 | $CH_3$ | $CH_2CH_3$ | (structure) | | |
| 115 | 3 | $CH_3$ | $CH_2CH_3$ | (structure) | 0.79* | 469.19 |

Example 109

$^1$H NMR ($D_6$-DMSO): δ 0.95 (t, J=7.3 Hz, 3 H), 1.75 (h, J=7.3 Hz, 2 H), 2.36 (s, 6 H), 2.58 (s, 3 H), 2.80 (t, J=7.5 Hz, 2 H), 3.50 (t, J=5.5 Hz, 2 H), 3.73-3.79 (m, 1 H), 3.80-3.86 (m, 1 H), 3.86-3.92 (m, 1 H), 4.66 (t, J=5.8 Hz, 1 H), 4.99 (d, J=5.0 Hz, 1 H), 7.72 (s, 1 H), 7.75 (s, 1 H), 7.86 (s, 2 H).

Example 113

$^1$H NMR ($D_6$-DMSO): δ 0.95 (t, J=7.3 Hz, 3 H), 1.26 (t, J=6.0 Hz, 3 H), 1.71-1.81 (m, 2 H), 2.37 (s, 3 H), 2.60 (s, 3 H), 2.75 (q, J=7.5 Hz, 2H), 2.82 (t, J=7.5 Hz, 2H), 3.10-3.19 (m, 2 H), 3.57-3.67 (m, 1 H), 3.72-3.82 (m, 2 H), 3.84 (s, 2 H), 3.93-4.01 (m, 1 H), 7.70 (t, J=5.8 Hz, 1 H), 7.78 (s, 1 H), 7.81 (s, 1 H), 7.88 (s, 2 H).

Examples 116 to 123

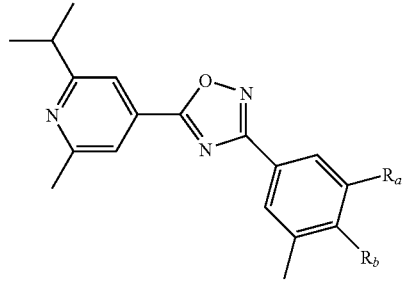

The following examples are prepared in analogy to previous examples starting from isonicotinic acid 13.

| | in analogy to | | | | LC-MS | |
|---|---|---|---|---|---|---|
| Example | Example | $R_a$ | $R_b$ | | $t_R$ [min] | $[M + H]^+$ |
| 116 | 10 | $CH_2CH_3$ | OH | | 0.92 | 338.10 |
| 117 | 10 | $CH_2CH_2CH_3$ | OH | | 1.13* | 352.40 |
| 118 | 17 | $CH_2CH_3$ | (structure) | | 0.90 | 382.10 |
| 119 | 14 | $CH_2CH_3$ | (structure) | | 0.81 | 412.11 |

-continued

| Example | in analogy to Example | $R_a$ | $R_b$ | LC-MS $t_R$ [min] | $[M + H]^+$ |
|---|---|---|---|---|---|
| 120 | 47 | $CH_2CH_3$ | ![structure: O-CH2-CH(OH)-CH2-NH2] | 0.71 | 411.05 |
| 121 | 3 | $CH_2CH_3$ | ![structure: O-CH2-CH(OH)-CH2-NH-C(O)-CH2-OH] | 0.79 | 469.21 |
| 122 | 46 | $CH_2CH_2CH_3$ | ![structure: O-CH2-CH(OH)-CH2-NH2, (S)] | 0.74 | 425.27 |
| 123 | 3 | $CH_2CH_2CH_3$ | ![structure: O-CH2-CH(OH)-CH2-NH-C(O)-CH2-OH, (S)] | 0.82 | 483.24 |

Example 123

$^1$H NMR δ 1.03 (t, J=7.3 Hz, 3 H), 1.39 (d, J=6.8 Hz, 6 H), 1.67-1.79 (m, 2 H), 2.40 (s, 3 H), 2.65-2.72 (m, 5 H), 2.99-3.04 (m, 1 H), 3.18 (hept, J=6.8 Hz, 1 H), 3.45-3.57 (m, 2 H), 3.76-3.83 (m, 1 H), 3.83-3.93 (m, 2 H), 4.18-4.24 (m, 3H), 7.08 (t, J=5.5 Hz, 1 H), 7.74 (s, 2 H), 7.87 (s, 2 H).

Example 124

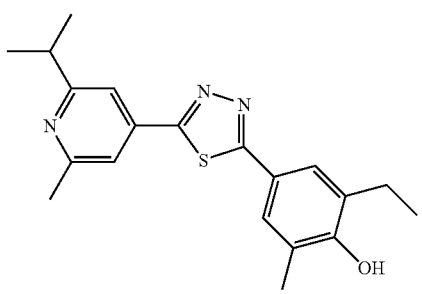 [SMILES: CCc1cc(-c2nnc(-c3cc(C)nc(C(C)C)c3)s2)cc(C)c1O]

a) To a solution of isonicotinic acid 13 (900 mg, 4.73 mmol), 4-benzyloxy-3-ethyl-5-methyl-benzoic acid hydrazide (2848 mg, 5.00 mmol) and DIPEA (1.73 g, 13.4 mmol) in DCM (50 mL), PyBOP (3257 mg, 6.26 mmol) is added at 0° C. The mixture is stirred at 0° C. for 30 min before it is diluted with EA, washed with sat. aq. NaHCO$_3$-solution. The org. extract is dried over Na$_2$SO$_4$, filtered and concentrated to give the crude di-acylhydrazide; LC-MS: $t_R$=0.74 min, [M+1]$^+$=446.09. This material and Lawesson reagent (1.86 g, 4.59 mmol) are dissolved in THF (15 mL) and the mixture is heated in the microwave at 110° C. for 5 min. The mixture is diluted with EA, washed with sat. aq. Na$_2$CO$_3$ solution, dried over MgSO$_4$, filtered and concentrated. The crude product is purified by CC on silica gel eluting with heptane:EA 9:1 to give 4-[5-(4-benzyloxy-3-ethyl-5-methyl-phenyl)-[1,3,4]thiadiazol-2-yl]-2-isopropyl-6-methyl-pyridine (837 mg) as a yellow oil; LC-MS: $t_R$=1.00 min, [M+1]$^+$=444.23.

b) To a solution of 4-[5-(4-benzyloxy-3-ethyl-5-methyl-phenyl)-[1,3,4]thiadiazol-2-yl]-2-isopropyl-6-methyl-pyridine (837 mg, 1.88 mmol) in EA (30 mL) 33% HBr in acetic acid (1 mL) is added. The mixture is stirred at rt for 3 h before it is diluted with EA, washed twice with sat. aq. NaHCO$_3$ solution, dried over MgSO$_4$, filtered and concentrated. The crude product is purified by CC on silica gel eluting with heptane:EA 4:1 to give 2-ethyl-4-[5-(2-isopropyl-6-methyl-pyridin-4-yl)-[1,3,4]thiadiazol-2-yl]-6-methyl-Phenol (540 mg) as a pale yellow oil; LC-MS: $t_R$=0.92* min, [M+1]$^+$=354.14.

Examples 125 to 130

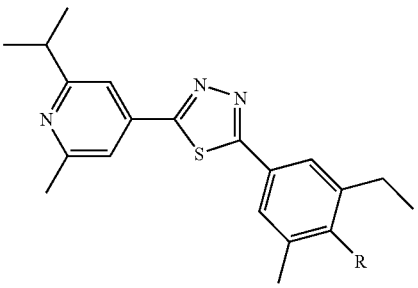

The following examples are prepared in analogy to previous examples starting from Example 124.

| | in analogy to | | | LC-MS | |
|---|---|---|---|---|---|
| Example | Example | R | | $t_R$ [min] | $[M+H]^+$ |
| 125 | 14 | (S)-glycerol ether (CH₂OH, OH wedge) | | 0.88* | 428.04 |
| 126 | 14 | (R)-glycerol ether | | 0.88* | 428.09 |
| 127 | 46 | 2-hydroxy-3-aminopropyl ether | | 0.96* | 426.84 |
| 128 | 3 | glycolamide derivative | | 0.81* | 485.10 |
| 129 | 46 | (S)-2-hydroxy-3-aminopropyl ether | | 0.99* | 426.92 |
| 130 | 3 | (R)-glycolamide derivative | | 0.81* | 485.17 |

Example 126

$^1$H NMR δ 1.33 (t, J=7.5 Hz, 3 H), 1.39 (d, J=7.0 Hz, 6 H), 2.13 (s br, 1 H), 2.41 (s, 3 H), 2.68 (s, 3 H), 2.77 (q, J=7.5 Hz, 2 H), 3.22 (s br, 1H), 3.81-3.99 (m, 4 H), 4.14-4.22 (m, 1 H), 7.57 (s, 1 H), 7.61 (s, 1 H), 7.73 (s, 1 H), 7.76 (s, 1 H).

Examples 131 to 136

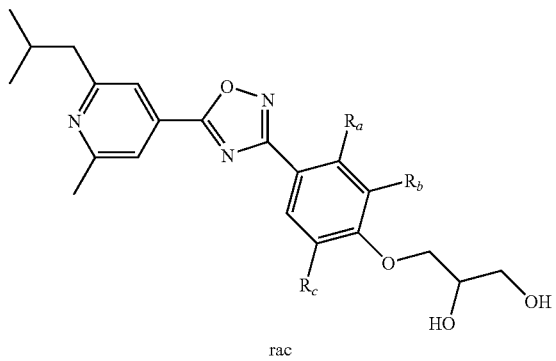

rac

The following compounds are prepared in analogy to Example 1 starting from isonicotinic acid.

| Example | $R_a$ | $R_b$ | $R_c$ | $t_R$ [min] | $[M+H]^+$ |
|---|---|---|---|---|---|
| 131 | H | H | H | 0.74 | 384.40 |
| 132 | CH₃ | H | H | 0.77 | 398.47 |
| 133 | H | OCH₃ | H | 0.85 | 414.20 |
| 134 | H | CH₃ | Cl | 0.84 | 432.05 |
| 135 | H | OCH₃ | Cl | 0.83 | 448.28 |
| 136 | H | H | Br | 0.82 | 462.20 |

Example 136

$^1$H NMR (CDCl$_3$): δ 1.00 (d, J=6.5 Hz, 6 H), 2.14-2.25 (m, 1 H), 2.69 (s, 3 H), 2.78 (d, J=7.5 Hz, 2 H), 3.86-3.98 (m, 3 H), 4.18-4.30 (m, 4H), 7.05 (d, J=8.5 Hz, 1 H), 7.68 (s, 1 H), 7.74 (s, 1 H), 8.12 (dd, J=8.5, 1.5 Hz, 1 H), 8.41 (d, J=1.5 Hz, 1 H).

Examples 137 and 138

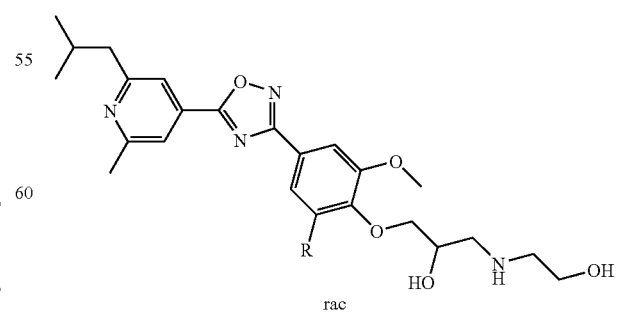

rac

The following examples are prepared in analogy to Example 20 from previous examples.

| Example | from Example | R | $t_R$ [min] | $[M+H]^+$ |
|---|---|---|---|---|
| 137 | 133 | H | 0.77 | 457.2 |
| 138 | 135 | Cl | 0.73 | 491.06 |

Examples 139 to 142

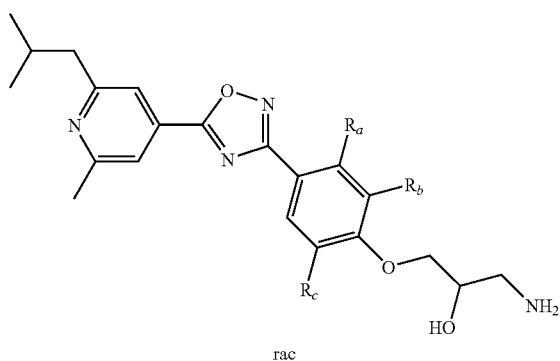

rac

The following examples are prepared in analogy to Example 2 from previous examples.

| Example | from Example | $R_a$ | $R_b$ | $R_c$ | $t_R$ [min] | $[M+H]^+$ |
|---|---|---|---|---|---|---|
| 139 | 132 | CH₃ | H | H | 0.70 | 397.18 |
| 140 | 133 | H | OCH₃ | H | 0.76 | 413.09 |
| 141 | 134 | H | CH₃ | Cl | 0.73 | 431.67 |
| 142 | 135 | H | OCH₃ | Cl | 0.73 | 447.06 |

Examples 143 to 146

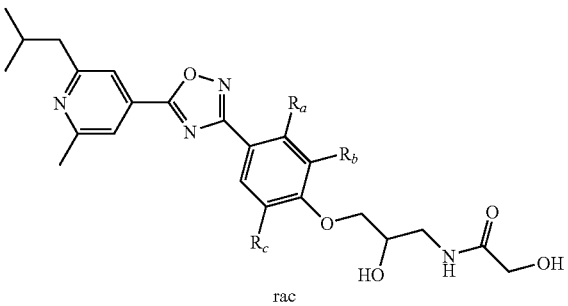

rac

The following examples are prepared in analogy to Example 3 from previous examples.

| Example | from Example | $R_a$ | $R_b$ | $R_c$ | $t_R$ [min] | $[M+H]^+$ |
|---|---|---|---|---|---|---|
| 143 | 139 | CH₃ | H | H | 0.76 | 455.22 |
| 144 | 140 | H | OCH₃ | H | 0.82 | 471.50 |
| 145 | 141 | H | CH₃ | Cl | 0.80 | 489.18 |
| 146 | 142 | H | OCH₃ | Cl | 0.79 | 505.27 |

Example 144

¹H NMR (CDCl₃): δ 1.01 (d, J=6.5 Hz, 6 H), 2.18-2.30 (m, 1 H), 2.46 (s, 3 H), 2.79 (d, J=7.3 Hz, 2 H), 3.50-3.59 (m, 1 H), 3.69-3.82 (m, 3 H), 3.99 (s, 3 H), 4.05-4.27 (m, 5 H), 7.03 (d, J=8.3 Hz, 1 H), 7.11 (t, J=5.5 Hz), 7.68 (s, 1 H), 7.79 (d, J=7.8 Hz), 8.21 (s, 1 H), 9.19 (s, 1 H).

Examples 147 to 150

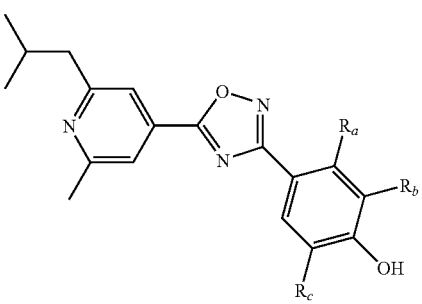

The following examples are prepared in analogy to example 10 starting from isonicotinic acid 6 and the appropriate 4,N-dihydroxybenzamidines.

| Example | $R_a$ | $R_b$ | $R_c$ | $t_R$ [min] | $[M+H]^+$ |
|---|---|---|---|---|---|
| 147 | OCH₃ | H | H | 0.78 | 340.10 |
| 148 | H | CH₂CH₂CH₃ | CH₃ | 0.96 | 366.13 |
| 149 | H | CH₃ | OCH₃ | 0.89 | 354.10 |
| 150 | H | Cl | OCH₃ | 0.90 | 374.05 |

Example 151

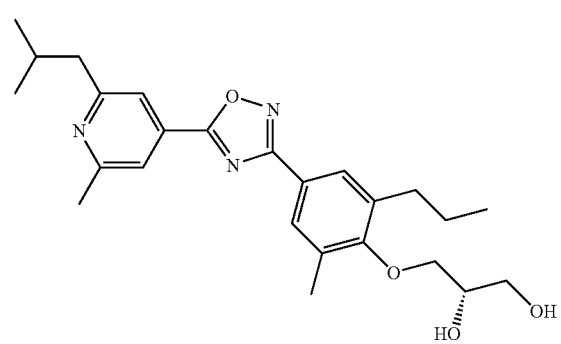 [SMILES: CCCc1cc(-c2noc(-c3cc(C)nc(CC(C)C)c3)n2)cc(C)c1OC[C@@H](O)CO]

(S)-3-{4-[5-(2-Isobutyl-6-methyl-pyridin-4-yl)-[1,2,4]oxadiazol-3-yl]-2-methyl-6-propyl-phenoxy}-propane-1,2-diol is prepared in analogy to Example 15 from Example 148; LC-MS: $t_R$=0.87 min, $[M+1]^+$=440.19.

Example 152

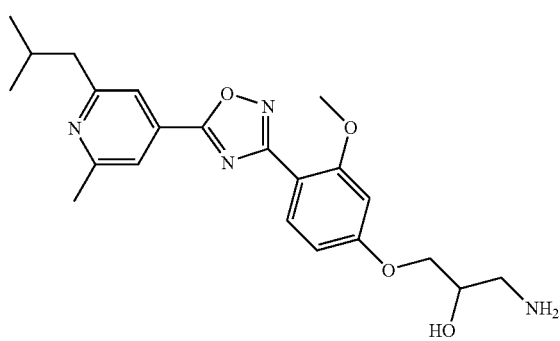 [SMILES: COc1cc(OCC(O)CN)ccc1-c1noc(-c2cc(C)nc(CC(C)C)c2)n1]

(RS)-1-Amino-3-{4-[5-(2-isobutyl-6-methyl-pyridin-4-yl)-[1,2,4]oxadiazol-3-yl]-3-methoxy-phenoxy}-propan-2-ol is prepared from Example 147 in analogy to Example 47; LC-MS: $t_R$=0.65 min, $[M+1]^+$=413.12.

Example 153

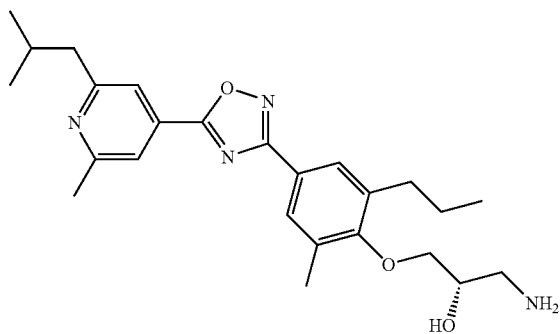 [SMILES: CCCc1cc(-c2noc(-c3cc(C)nc(CC(C)C)c3)n2)cc(C)c1OC[C@@H](O)CN]

(S)-1-Amino-3-{4-[5-(2-isobutyl-6-methyl-pyridin-4-yl)-[1,2,4]oxadiazol-3-yl]-2-methyl-6-propyl-phenoxy}-propan-2-ol is prepared in analogy to Example 47 from Example 148; LC-MS: $t_R$=0.76 min, $[M+1]^+$=439.28.

Example 154

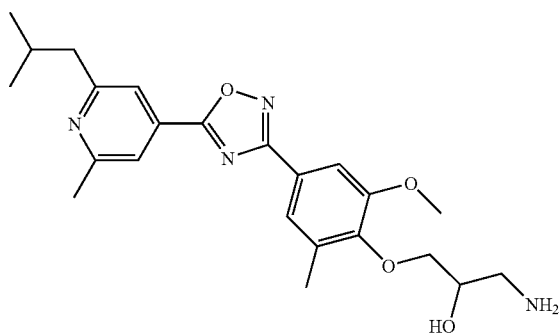 [SMILES: COc1cc(-c2noc(-c3cc(C)nc(CC(C)C)c3)n2)cc(C)c1OCC(O)CN]

(RS)-1-Amino-3-{4-[5-(2-isobutyl-6-methyl-pyridin-4-yl)-[1,2,4]oxadiazol-3-yl]-2-methoxy-6-methyl-phenoxy}-propan-2-ol is prepared in analogy to Example 46 from Example 149; LC-MS: $t_R$=0.71 min, $[M+1]^+$=427.08.

Examples 155 and 156

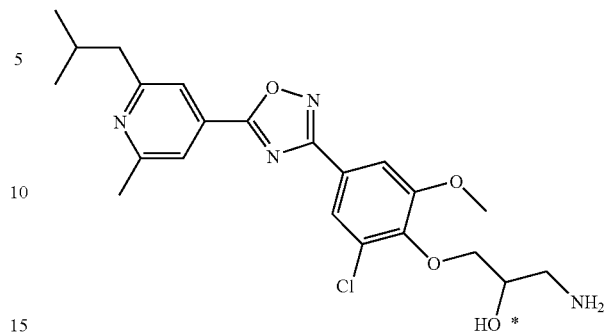

The following examples are prepared from Example 150 in analogy to Example 46.

| Example | *Chirality | LC-MS $t_R$ [min] | $[M + H]^+$ |
|---|---|---|---|
| 155 | R | 0.72 | 447.13 |
| 156 | S | 0.72 | 447.13 |

Example 157

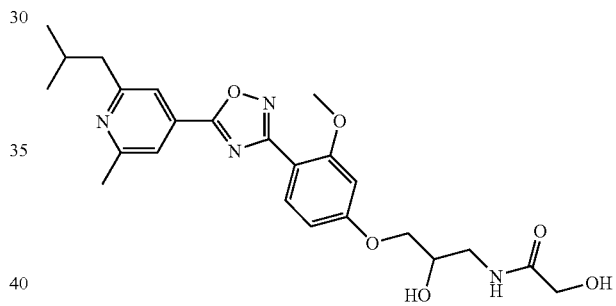

(RS)-2-Hydroxy-N-(2-hydroxy-3-{4-[5-(2-isobutyl-6-methyl-pyridin-4-yl)-[1,2,4]oxadiazol-3-yl]-3-methoxy-phenoxy}-propyl)-acetamide is prepared in analogy to Example 3 from Example 152; LC-MS: $t_R$=0.71 min, $[M+1]^+$=471.21.

Example 158

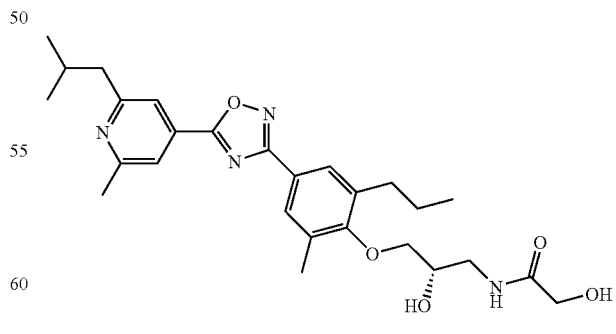

(S)-2-Hydroxy-N-(2-hydroxy-3-{4-[5-(2-isobutyl-6-methyl-pyridin-4-yl)-[1,2,4]oxa-diazol-3-yl]-2-methyl-6-propyl-phenoxy}-propyl)-acetamide is prepared in analogy to Example 3 starting from Example 152; LC-MS: $t_R$=0.94 min, $[M+1]^+$=497.14.

Example 159

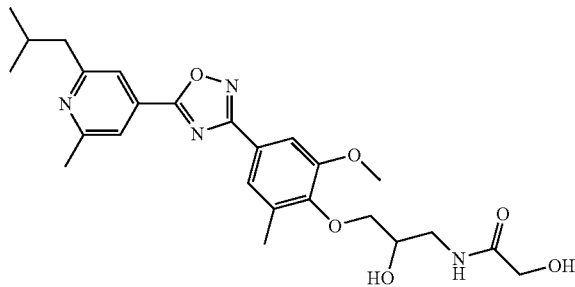 [SMILES: COc1cc(-c2noc(-c3cc(C)nc(CC(C)C)c3)n2)cc(C)c1OCC(O)CNC(=O)CO]

(RS)-2-Hydroxy-N-(2-hydroxy-3-{4-[5-(2-isobutyl-6-methyl-pyridin-4-yl)-[1,2,4]oxadiazol-3-yl]-2-methoxy-6-methyl-phenoxy}-propyl)-acetamide is prepared in analogy to Example 3 starting from Example 154; LC-MS: $t_R$=0.77 min, $[M+1]^+$=485.21.

Examples 160 and 161

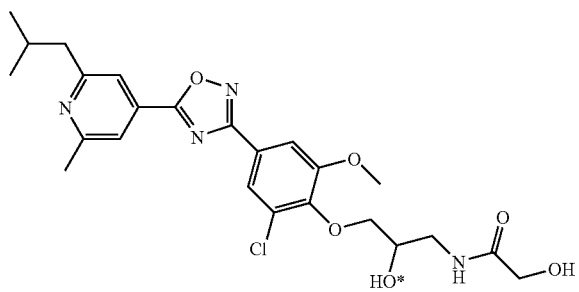

The following examples are prepared from previous examples in analogy to Example 3.

| Example | from Example | *Chirality | LC-MS $t_R$ [min] | $[M + H]^+$ |
|---|---|---|---|---|
| 160 | 155 | R | 0.80 | 505.18 |
| 161 | 156 | S | 0.79 | 505.20 |

Example 162

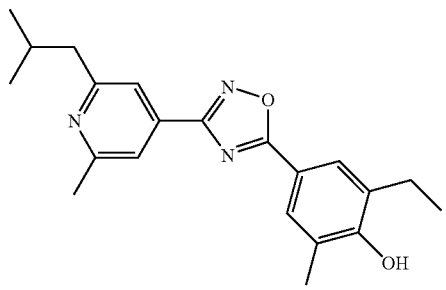 [SMILES: CCc1cc(-c2nc(-c3cc(C)nc(CC(C)C)c3)no2)cc(C)c1O]

2-Ethyl-4-[3-(2-isobutyl-6-methyl-pyridin-4-yl)-[1,2,4]oxadiazol-5-yl]-6-methyl-phenol is prepared from N-hydroxy-2-isobutyl-6-methyl-isonicotinamidine and 3-ethyl-4-hydroxy-5-methyl-benzoic acid; LC-MS: $t_R$=0.90 min, $[M+1]^+$=352.17.

Examples 163 and 164

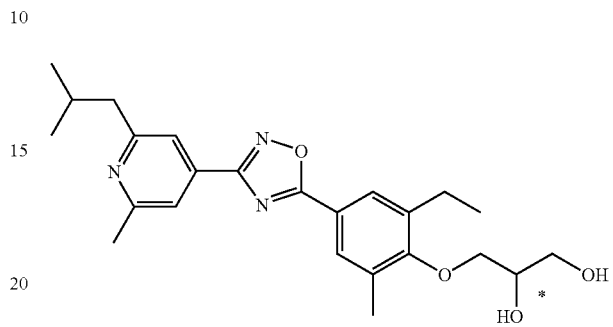

The following examples are prepared in analogy to Example 14 from Example 162.

| Example | *Chirality | LC-MS $t_R$ [min] | $[M + H]^+$ |
|---|---|---|---|
| 163 | R | 0.81 | 426.16 |
| 164 | S | 0.81 | 426.16 |

Example 164

$^1$H NMR (CDCl$_3$): δ0.99 (d, J=6.5 Hz, 6 H), 1.34 (t, J=7.5 Hz, 3 H), 2.10 (s br, 1 H), 2.14-2.25 (m, 1 H), 2.43 (s, 3 H), 2.67 (s, 3 H), 2.72-2.84 (m, 5 H), 3.81-3.99 (m, 4 H), 4.16-4.22 (m, 1 H), 7.68 (s, 1 H), 7.74 (s, 1 H), 7.94 (s, 1 H), 7.95 (s, 1 H).

Examples 165 to 184

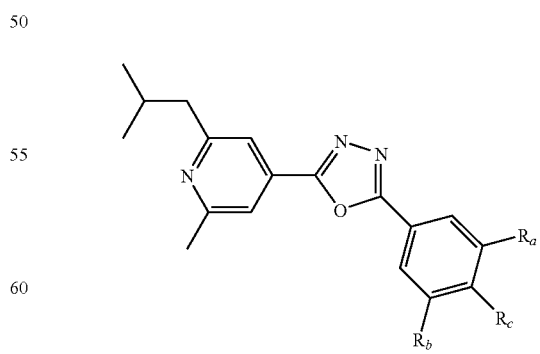

The following examples are prepared in analogy to previous examples starting from isonicotinic acid 6 and the corresponding 4-benzyloxybenzoic acid hydrazides.

| Example | prepared in analogy to Example | $R_a$ | $R_b$ | $R_c$ | LC-MS $t_R$ [min] | $[M + H]^+$ |
|---|---|---|---|---|---|---|
| 165 | 75 | $CH_3$ | $CH_3$ | OH | 0.81 | 338.13 |
| 166 | 75 | $CH_3$ | $CH_2CH_3$ | OH | 0.95* | 352.07 |
| 167 | 75 | Cl | $OCH_3$ | OH | 0.81 | 374.05 |
| 168 | 14 | $CH_3$ | $CH_3$ | (S)-glyceryl ether (OCH2-CH(OH)-CH2OH) | 0.84* | 412.22 |
| 169 | 14 | $CH_3$ | $CH_3$ | (R)-glyceryl ether | 0.84* | 412.23 |
| 170 | 17 | $CH_3$ | $CH_2CH_3$ | OCH2CH2OH | 0.96* | 396.18 |
| 171 | 47 | $CH_3$ | $CH_2CH_3$ | (S)-OCH2-CH(OH)-CH2NH2 | | |
| 172 | 3 | $CH_3$ | $CH_2CH_3$ | (S)-OCH2-CH(OH)-CH2-NH-C(O)-CH2OH | 0.79* | 469.19 |
| 173 | 47 | $CH_3$ | $CH_2CH_3$ | (R)-OCH2-CH(OH)-CH2NH2 | | |
| 174 | 3 | $CH_3$ | $CH_2CH_3$ | (R)-OCH2-CH(OH)-CH2-NH-C(O)-CH2OH | 0.80* | 469.20 |
| 175 | 47 | $CH_3$ | $CH_2CH_3$ | (S)-OCH2-CH(OH)-CH2NH2 | 0.91* | 425.12 |
| 176 | 47 | $CH_3$ | $CH_2CH_3$ | (R)-OCH2-CH(OH)-CH2NH2 | 0.90* | 425.12 |
| 177 | 20 | $CH_3$ | $CH_2CH_3$ | (S)-OCH2-CH(OH)-CH2-NH-CH2CH2OH | 0.85 | 469.22 |
| 178 | 20 | $CH_3$ | $CH_2CH_3$ | (R)-OCH2-CH(OH)-CH2-NH-CH2CH2OH | 0.85 | 469.25 |
| 179 | 3 | $CH_3$ | $CH_2CH_3$ | (S)-OCH2-CH(OH)-CH2-NH-C(O)-CH2OH | 0.82* | 483.23 |
| 180 | 3 | $CH_3$ | $CH_2CH_3$ | (R)-OCH2-CH(OH)-CH2-NH-C(O)-CH2OH | 0.82* | 483.21 |

-continued

| Example | prepared in analogy to Example | $R_a$ | $R_b$ | $R_c$ | LC-MS $t_R$ [min] | $[M + H]^+$ |
|---|---|---|---|---|---|---|
| 181 | 46 | Cl | OCH$_3$ | ![structure] | 0.67 | 447.20 |
| 182 | 3 | Cl | OCH$_3$ | ![structure] | 0.73 | 505.18 |
| 183 | 46 | Cl | OCH$_3$ | ![structure] | 0.65 | 447.17 |
| 184 | 3 | Cl | OCH$_3$ | ![structure] | 0.73 | 505.19 |

Example 167

$^1$H NMR (D$_6$-DMSO): δ 0.92 (d, J=6.5 Hz, 6 H), 2.07-2.19 (m, 1 H), 2.59 (s, 3 H), 2.70 (d, J=7.3 Hz, 2 H), 3.98 (s, 3 H), 7.63 (s, 1 H), 7.74 (s, 1 H), 7.81 (s, 2 H), 10.49 (s, 1 H).

Example 170

$^1$H NMR (CDCl$_3$): δ 1.00 (d, J=6.5 Hz, 6 H), 1.34 (t, J=7.8 Hz, 3 H), 2.16-2.25 (m, 1 H), 2.44 (s, 3 H), 2.69 (s, 3 H), 2.77 (d, J=7.3 Hz, 2 H), 2.81 (q, J=7.8 Hz, 2 H), 3.98-4.06 (m, 4 H), 7.64 (s, 1 H), 7.69 (s, 1 H), 7.86 (d, J=2.0 Hz, 1 H), 7.89 (d, J=2.0 Hz, 1 H).

Example 180

$^1$H NMR (CDCl$_3$): δ 1.00 (d, J=6.5 Hz, 6 H), 1.33 (t, J=7.5 Hz, 3 H), 2.15-2.24 (m, 1 H), 2.42 (s, 3 H), 2.69 (s, 3 H), 2.77 (q, J=8.0 Hz, 2 H), 3.34 (d, J=4.5 Hz, 1 H), 3.51-3.59 (m, 1 H), 3.76-3.95 (m, 3 H), 4.19-4.26 (m, 3 H), 7.00 (t, J=5.5 Hz), 7.64 (s, 1 H), 7.69 (s, 1 H), 7.86 (s, 1 H), 7.88 (s, 1 H).

Example 185

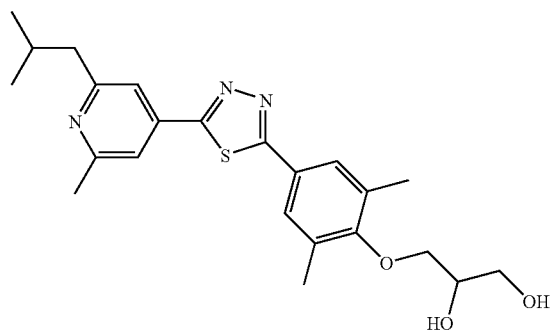 [SMILES: Cc1cc(-c2nnc(-c3cc(C)c(OCC(O)CO)c(C)c3)s2)cc(CC(C)C)n1]

(RS)-3-{4-[5-(2-Isobutyl-6-methyl-pyridin-4-yl)-[1,3,4]thiadiazol-2-yl]-2,6-dimethyl-phenoxy}-propane-1,2-diol is prepared starting from isonicotinic acid 6 and 4-allyloxy-3,5-dimethyl-benzoic acid hydrazide in analogy to Example 1 using Lawesson reagent in the cyclization step of the thiadiazole as describe in Example 124; LC-MS: $t_R$=0.73 min, $[M+1]^+$=428.47.

Examples 186 to 192

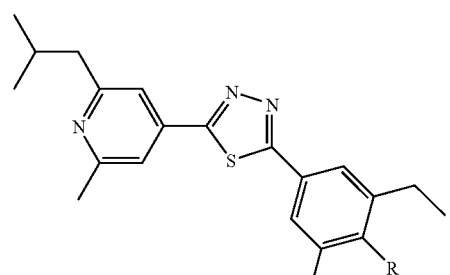

The following examples are prepared in analogy to previous examples starting from isonicotinic acid 6 and 4-benzyloxy-3-ethyl-5-methylbenzoic acid hydrazide.

| Example | in analogy to Example | R | LC-MS $t_R$ [min] | $[M + H]^+$ |
|---|---|---|---|---|
| 186 | 124 | OH | 0.91* | 368.14 |
| 187 | 14 | ![structure] O-CH2-CH(OH)-CH2OH (S) | 0.90 | 442.08 |
| 188 | 14 | ![structure] O-CH2-CH(OH)-CH2OH (R) | 0.90* | 442.90 |
| 189 | 46 | ![structure] O-CH2-CH(OH)-CH2NH2 (S) | 1.06* | 441.13 |
| 190 | 46 | ![structure] O-CH2-CH(OH)-CH2NH2 (R) | 0.67 | 441.23 |
| 191 | 3 | ![structure] O-CH2-CH(OH)-CH2-NH-C(O)-CH2OH (S) | 0.83* | 499.12 |
| 192 | 3 | ![structure] O-CH2-CH(OH)-CH2-NH-C(O)-CH2OH (R) | 0.83* | 499.12 |

Example 192

$^1$H NMR (CDCl$_3$): δ 0.99 (d, J=6.8 Hz, 6 H), 1.32 (t, J=7.5 Hz, 3 H), 2.12-2.22 (m, 1 H), 2.39 (s, 3 H), 2.65 (s, 2 H), 2.71-2.79 (m, 4 H), 3.43-3.58 (m, 3 H), 3.76-3.93 (m, 3 H), 4.19-4.25 (m, 3 H), 7.08 (t br, J=6.0 Hz, 1 H), 7.51 (s, 1 H), 7.56 (s, 1 H), 7.71 (s, 1 H), 7.73 (s, 1 H).

Examples 193 to 206

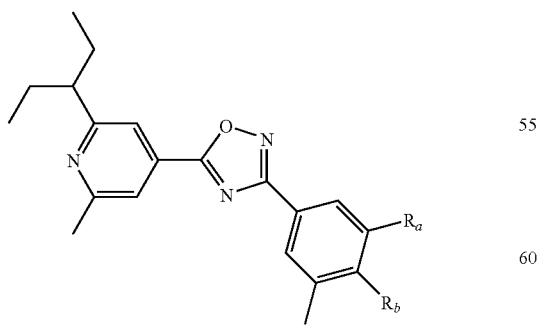

The following examples are prepared in analogy to previous examples starting from isonicotinic acid 14 and 3-ethyl-4,N-dihydroxy-5-methyl-benzamidine.

| | in analogy to | | | LC-MS | |
|---|---|---|---|---|---|
| Example | Example | $R_a$ | $R_b$ | $t_R$ [min] | $[M+H]^+$ |
| 193 | 10 | $CH_2CH_3$ | OH | 0.96 | 366.16 |
| 194 | 10 | $CH_2CH_2CH_3$ | OH | 1.24* | 380.15 |
| 195 | 14 | $CH_2CH_3$ | –O–CH$_2$–CH(OH)–CH$_2$OH (S) | 0.87 | 440.04 |
| 196 | 14 | $CH_2CH_3$ | –O–CH$_2$–CH(OH)–CH$_2$OH (R) | 0.87 | 440.24 |
| 197 | 14 | $CH_2CH_2CH_3$ | –O–CH$_2$–CH(OH)–CH$_2$OH (S) | 1.10 | 454.10 |
| 198 | 14 | $CH_2CH_2CH_3$ | –O–CH$_2$–CH(OH)–CH$_2$OH (R) | 1.10 | 454.10 |
| 199 | 46 | $CH_2CH_3$ | –O–CH$_2$–CH(OH)–CH$_2$NH$_2$ (R) | 1.42* | 439.36 |
| 200 | 46 | $CH_2CH_3$ | –O–CH$_2$–CH(OH)–CH$_2$NH$_2$ (S) | 1.34* | 439.38 |
| 201 | 46 | $CH_2CH_2CH_3$ | –O–CH$_2$–CH(OH)–CH$_2$NH$_2$ (R) | 1.12* | 453.13 |
| 202 | 46 | $CH_2CH_2CH_3$ | –O–CH$_2$–CH(OH)–CH$_2$NH$_2$ (S) | 1.40 | 453.11 |
| 203 | 3 | $CH_2CH_3$ | –O–CH$_2$–CH(OH)–CH$_2$–NH–C(O)–CH$_2$OH (S) | 0.84 | 497.26 |
| 204 | 3 | $CH_2CH_3$ | –O–CH$_2$–CH(OH)–CH$_2$–NH–C(O)–CH$_2$OH (R) | 0.84 | 497.26 |
| 205 | 3 | $CH_2CH_2CH_3$ | –O–CH$_2$–CH(OH)–CH$_2$–NH–C(O)–CH$_2$OH (S) | 1.01 | 511.11 |
| 206 | 3 | $CH_2CH_2CH_3$ | –O–CH$_2$–CH(OH)–CH$_2$–NH–C(O)–CH$_2$OH (R) | 1.01 | 511.11 |

Example 194

$^1$H NMR (CDCl$_3$): δ 0.85 (t, J=7.3 Hz, 6 H), 1.05 (t, J=7.3 Hz, 3 H), 1.69-1.84 (m, 6 H), 2.37 (s, 3 H), 2.65-2.73 (m, 7 H), 5.04 (s, 1 H), 7.67 (s, 1 H), 7.74 (s, 1 H), 7.84 (s, 1 H), 7.85 (s, 1 H).

Example 195

$^1$H NMR δ 0.85 (t, J=7.5 Hz, 6 H), 1.33 (t, J=7.5 Hz, 3 H), 1.79 (quint, J=7.3 Hz, 4 H), 2.22 (t, J=5.8 Hz, 1 H), 2.41 (s, 3 H), 2.69 (s, 3 H), 2.71-2.86 (m, 3 H), 3.81-4.03 (m, 4 H), 4.14-4.21 (m, 1 H), 7.67 (s, 1 H), 7.74 (s, 1 H), 7.88 (s, 1 H), 7.90 (s, 1 H).

Examples 207 to 210

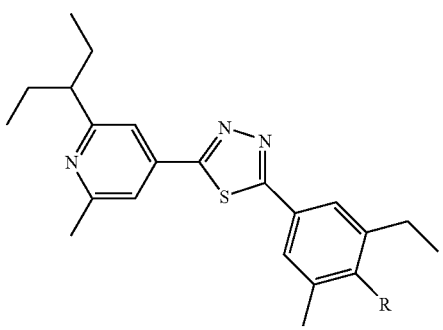

The following examples are prepared in analogy to previous examples starting from isonicotinic acid 14 and 4-benzyloxy-3-ethyl-5-methyl benzoic acid hydrazide.

| Example | in analogy to Example | R | LC-MS t$_R$ [min] | [M + H]$^+$ |
|---|---|---|---|---|
| 207 | 124 | OH | 0.88 | 382.15 |
| 208 | 14 | ![structure] O-CH$_2$-CH(OH)-CH$_2$OH | 0.78 | 456.25 |
| 209 | 47 | O-CH$_2$-CH(OH)-CH$_2$NH$_2$ | 0.72 | 455.27 |
| 210 | 3 | O-CH$_2$-CH(OH)-CH$_2$-NH-C(O)-CH$_2$OH | 0.76 | 513.26 |

Example 210

$^1$H NMR (CDCl$_3$): δ 0.85 (t, J=7.3 Hz, 6 H), 1.32 (t, J=7.5 Hz, 3 H), 1.78 (quint, J=7.5 Hz, 4 H), 2.39 (s, 3 H), 2.61-2.69 (m, 4 H), 2.75 (q, J=7.3 Hz, 2 H), 3.50-3.58 (m, 1 H), 3.75-3.93 (m, 3 H), 4.18-4.25 (m, 3 H), 7.07 (s br, 1 H), 7.50 (s, 1 H), 7.54 (s, 1 H), 7.72 (s, 1 H), 7.74 (s, 1 H).

Examples 211 and 212

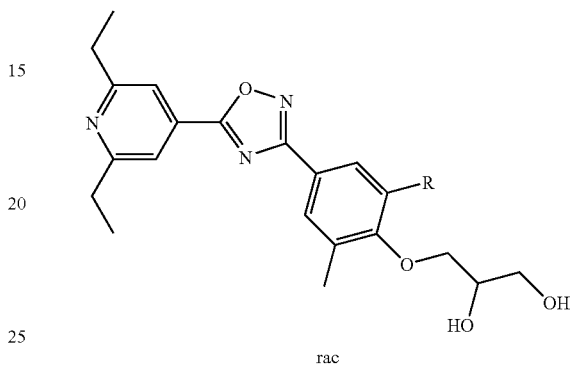

rac

The following examples are prepared in analogy to Example 1 starting from isonicotinic acid 7 and the appropriate allyloxy-N-hydroxy-benzamidine.

| Example | R | LC-MS t$_R$ [min] | [M + H]$^+$ |
|---|---|---|---|
| 211 | CH$_3$ | 0.77 | 398.55 |
| 212 | CH$_2$CH$_3$ | 0.80 | 412.58 |

Examples 213 to 215

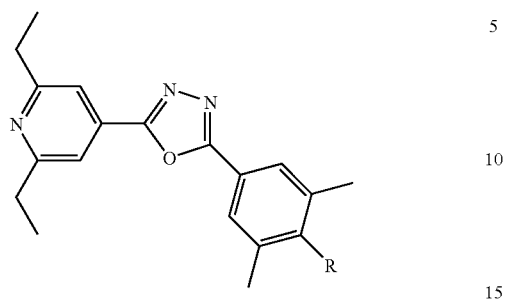

The following examples are prepared in analago to previous examples starting from isonicotinic acid 7 and 4-benzyloxy-3,5-dimethyl benzoic acid hydrazide.

| Example | in analogy to Example | R | LC-MS $t_R$ [min] | $[M + H]^+$ |
|---|---|---|---|---|
| 213 | 75 | OH | 0.78 | 324.14 |
| 214 | 47 | O-CH2-CH(OH)-CH2-NH2 | 0.63 | 397.11 |
| 215 | 3 | O-CH2-CH(OH)-CH2-NH-C(O)-CH2-OH | 0.74* | 455.18 |

Example 215

$^1$H NMR δ1.30 (t, J=7.5 Hz, 6 H) 2.36 (s, 6 H), 2.86 (q, J=7.8 Hz, 4 H), 3.58-3.67 (m, 2 H), 3.72-3.81 (m, 2 H), 3.84 (d, J=5.8 Hz, 2 H), 3.92-3.99 (m, 1 H), 5.31 (d, J=5.3 Hz, 1 H), 5.56 (t, J=5.8 Hz, 1 H), 7.70 (t, J=5.8 Hz, 1 H), 7.76 (s, 2 H), 7.87 (s, 2 H).

Examples 216 and 217

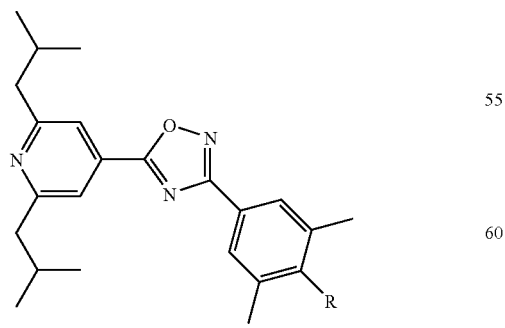

Starting from Example 23, the following examples are prepared.

| in analogy to | | | LC-MS | |
|---|---|---|---|---|
| Example | Example | R | $t_R$ [min] | [M + H]$^+$ |
| 216 | 2 | 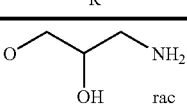 | | |
| 217 | 3 | 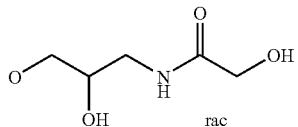 | 0.92 | 511.62 |

Example 218

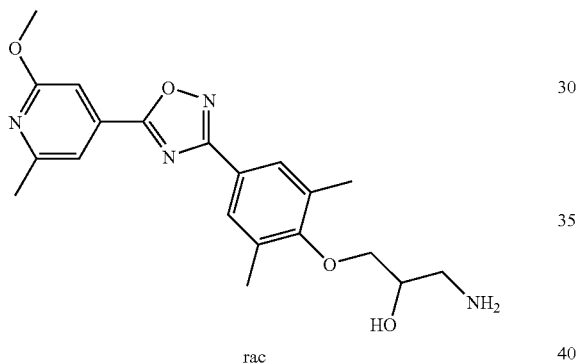

(RS)-1-Amino-3-{4-[5-(2-methoxy-6-methyl-pyridin-4-yl)-[1,2,4]oxadiazol-3-yl]-2,6-dimethyl-phenoxy}-propan-2-ol is prepared from Example 27 in analogy to Example 2; MS: [M+1]$^+$=399.52.

Example 219

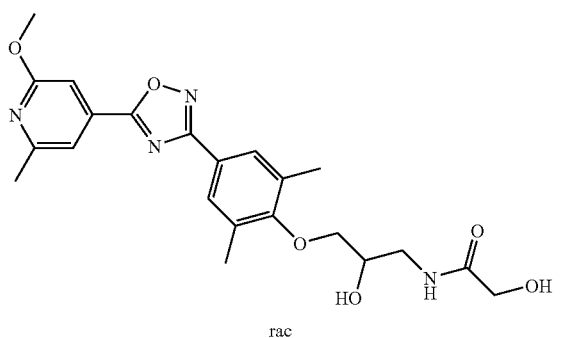 [SMILES: COc1cc(-c2nc(-c3cc(C)c(OCC(O)CNC(=O)CO)c(C)c3)no2)cc(C)n1 ; "rac"]

(RS)-2-Hydroxy-N-(2-hydroxy-3-{4-[5-(2-methoxy-6-methyl-pyridin-4-yl)-[1,2,4]oxadiazol-3-yl]-2,6-dimethyl-phenoxy}-propyl)-acetamide is prepared from Example 218 in analogy to Example 3; LC-MS: $t_R$=0.96 min, [M+1]$^+$=457.25.

Examples 220 to 226

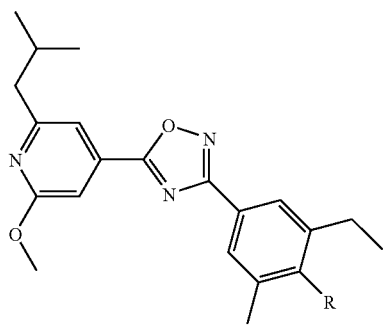

The following examples are prepared starting from isonicotinic acid 15 and 3-ethyl-4,N-dihydroxy-5-methyl benzamidine.

| Example | in analogy to Example | R | LC-MS $t_R$ [min] | $[M + H]^+$ |
|---|---|---|---|---|
| 220 | 10 | OH | 1.18 | 368.18 |
| 221 | 14 | 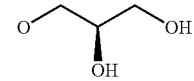 | 1.10 | 442.18 |
| 222 | 14 | 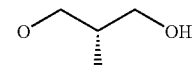 | 1.10 | 442.22 |
| 223 | 47 |  | 0.92 | 441.24 |
| 224 | 47 | 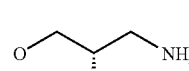 | 0.92 | 441.25 |
| 225 | 3 | 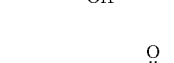 | 1.05 | 499.22 |
| 226 | 3 | 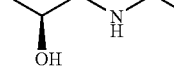 | 1.05 | 499.19 |
Example 226
$^1$H NMR (CDCl$_3$): δ 1.00 (d, J=6.5 Hz, 6 H), 1.33 (t, J=7.5 Hz, 3 H), 2.18-2.29 (m, 1 H), 2.40 (s, 3 H), 2.51 (s br, 1 H), 2.70 (d, J=7.0 Hz, 2 H), 2.76 (q, J=7.3 Hz, 2 H), 3.33 (s br, 1 H), 3.50-3.57 (m, 1 H), 3.76-3.94 (m, 3 H), 4.02 (s, 3 H), 4.18-4.26 (m, 3 H), 6.99 (s br, 1 H), 7.33 (s, 1 H), 7.46 (s, 1 H), 7.87 (s, 1 H), 7.89 (s, 1 H).
Examples 227 to 233
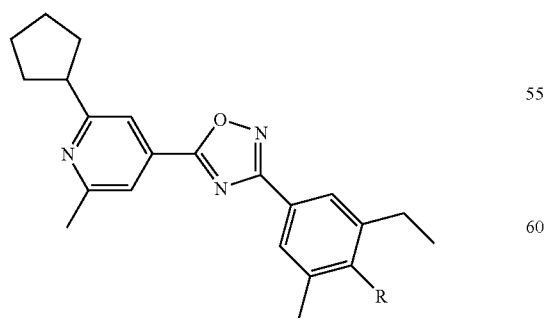
The following examples are prepared in analogy to previous examples starting from isonicotinic acid 16.

| Example | in analogy to Example | R | LC-MS t_R [min] | [M + H]+ |
|---|---|---|---|---|
| 227 | 10 | OH | 1.01 | 364.28 |
| 228 | 14 | 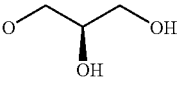 | 0.86 | 438.27 |
| 229 | 14 | 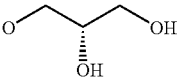 | 0.86 | 438.27 |
| 230 | 47 | 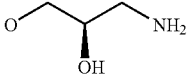 | 0.75 | 437.28 |
| 231 | 47 | 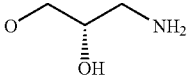 | 0.75 | 437.27 |
| 232 | 3 | 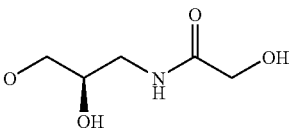 | 0.83 | 495.30 |
| 233 | 3 | 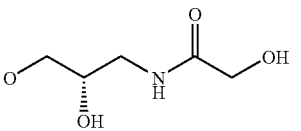 | 0.83 | 495.34 |

Example 228

$^1$H NMR (CDCl$_3$): δ 1.34 (t, J=7.5 Hz, 3 H), 1.73-1.95 (m, 6 H), 2.03-2.09 (m, 1 H), 2.12-2.21 (m, 2 H), 2.42 (s, 3 H), 2.68 (s, 3 H), 2.78 (q, J=7.5 Hz, 2 H), 3.25-3.35 (m, 1 H), 3.51 (s br, 1 H), 3.81-3.98 (m, 4 H), 4.14-4.21 (m, 1 H), 7.73 (s, 1 H), 7.76 (s, 1 H), 7.89 (s, 1 H), 7.90 (s, 1 H).

Example 234

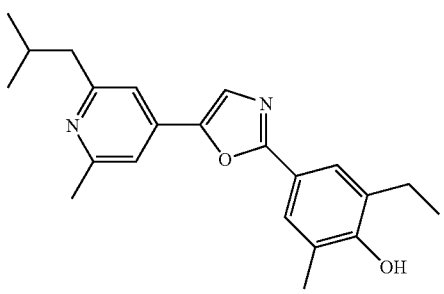 [SMILES: CCc1cc(-c2ncc(-c3cc(C)nc(CC(C)C)c3)o2)cc(C)c1O]

a) To a solution of isonicotinic acid 6 (3.80 g, 16.5 mmol) in DCM (50 mL), DIPEA (10.7 g, 82.7 mmol) followed by TBTU (6.37 g, 19.9 mmol) is added. The mixture is stirred at rt for 10 min before N,O-dimethylhydroxylamine (1.94 g, 19.9 mmol) is added. The mixture is stirred at rt for 1 h before it is diluted with DCM, washed with sat. aq. NaHCO$_3$, followed by water, dried over MgSO$_4$, filtered and concentrated. The crude product is purified by CC on silica gel eluting with heptane:EA 1:1 to give 2-isobutyl-N-methoxy-6,N-dimethyl-isonicotinamide (3.37 g) as a colourless oil; LC-MS: t$_R$=0.61 min.

b) To a solution of 2-isobutyl-N-methoxy-6,N-dimethyl-isonicotinamide (410 mg, 1.74 mmol) in THF (10 mL), methyl magnesium bromide (1.17 mL of a 3 M solution in ether, 3.47 mmol) is added at 5° C. The mixture is stirred at 5° C. for 1.5 h. The reaction is quenched by adding NH$_4$Cl. The mixture is diluted with EA (50 mL), washed with sat. aq. NaHCO$_3$, dried over Na$_2$SO$_4$, filtered and concentrated. The crude product is purified by CC on silica gel eluting with heptane:EA 4:1 to give 1-(2-isobutyl-6-methyl-pyridin-4-yl)-ethanone (280 mg) as a colourless oil. LC-MS: t$_R$=0.84 min.

c) A solution of hydroxylamine hydrochloride (120 mg, 1.732 mmol) in water (0.5 mL) and 1 N aq. NaOH (1.2 mL) is added to 1-(2-isobutyl-6-methyl-pyridin-4-yl)-ethanone (276 mg, 1.44 mmol). The solution is stirred at 80° C. for 2 h, MeOH is added to maintain homogeneity of the mixture. The mixture is cooled to rt and the precipitate that forms is collected, washed with water and dried in vacuo to give 1-(2-isobutyl-6-methyl-pyridin-4-yl)-ethanone oxime (258 mg) as a white solid; $^1$H NMR (D$_6$-DMSO): δ 0.88 (d, J=6.5 Hz, 6 H), 1.98-2.10 (m, 1 H), 2.13 (s, 3 H), 2.45 (s, 3 H), 2.56 (d, J=7.0 Hz, 2 H), 7.22 (s, 1 H), 7.27 (s, 1 H), 11.54 (s, 1 H).

d) To a solution of 1-(2-isobutyl-6-methyl-pyridin-4-yl)-ethanone oxime (125 mg, 0.606 mmol) in pyridine (0.4 mL), p-toluenesulfonyl chloride (127 mg, 0.667 mmol) is added at 5° C. The mixture is stirred at 5° C. for 15 h before another portion of p-toluene sulfonylchloride (63 mg, 0.334 mmol) is added. Stirring is continued for 5 h. The solvent is evaporated, the remaining residue is partioned between water (15 mL) and EA (25 mL). The org. phase is separated, washed with water, dried over MgSO₄, filtered and concentrated. The crude product in purified by CC on silica gel eluting with heptane:EA 3:1 to 2:1 to give 1-(2-isobutyl-6-methyl-pyridin-4-yl)-ethanone oxime p-toluenesulfonic ester (177 mg) as a pale yellow oil; LC-MS: $t_R$=0.99*, [M+1]⁺=361.04.

e) A solution of potassium ethanolate (24% in water, 0.3 mL) is added to a solution of 1-(2-isobutyl-6-methyl-pyridin-4-yl)-ethanone oxime p-toluenesulfonic ester (500 mg, 1.39 mmol) in EtOH (1.7 mL) at 5° C. The mixture is stirred at rt for 1 h. The mixture is diluted with ether and stirred for 30 min before it is filtered through celite. The filtrate is concentrated and dissolved in ether (25 mL). 2 N aq. HCl (15 mL) is added an the mixture is stirred at rt for 1 h. The org. phase is separated and extracted with 2 N aq. HCl (3×20 mL). The aq. extracts are combined and concentrated to give crude 2,2-diethoxy-2-(2-isobutyl-6-methyl-pyridin-4-yl)-ethylamine dihydrochloride (453 mg) as a yellow resin; LC-MS: $t_R$=0.84*, [M+1]⁺=281.23.

f) To a solution of 4-benzyloxy-3-ethyl-5-methylbenzoic acid (115 mg, 0.425 mmol) in DMF (1.5 mL), EDC HCl (46 mg, 0.467 mmol) followed by HOBT (63 mg, 0.467 mmol) is added. The mixture is stirred at rt for 15 min before DIPEA (219 mg, 1.70 mmol) and a solution of 2,2-diethoxy-2-(2-isobutyl-6-methyl-pyridin-4-yl)-ethylamine dihydrochloride (150 mg, 0.425 mmol) in DMF (0.5 mL) is added. The mixture is stirred at rt for 4.5 h before another portion of EDC HCl (20 mg) and HOBT (30 mg) is added. Stirring is continued at rt for 16 h. The mixture is diluted with EA (30 mL), washed with sat. aq. NaHCO₃ solution (15 mL), water (15 mL) and brine (15 mL), dried over Na₂SO₄, filtered and concentrated. The crude product is purified on prep. TLC with heptane:EA 1:1 to give 4-benzyloxy-N-[2,2-diethoxy-2-(2-isobutyl-6-methyl-pyridin-4-yl)-ethyl]-3-ethyl-5-methyl-benzamide (137 mg) as a pale yellow wax; LC-MS: $t_R$=1.13, [M+1]⁺=533.15.

g) To a solution of the above 4-benzyloxy-N-[2,2-diethoxy-2-(2-isobutyl-6-methyl-pyridin-4-yl)-ethyl]-3-ethyl-5-methyl-benzamide (112 mg, 0.210 mmol) in acetone (5 mL), 1 N aq. HCl (5.5 mL) is added and the mixture is stirred at 70° C. for 5 h. The acetone is evaporated and the remaining mixture is cooled to 0° C. before it is neutralized with aq. NaOH solution and extracted twice with EA (2×20 mL). The combined org. extracts are dried over Na₂SO₄, filtered and concentrated. The crude product is purified by prep. TLC using heptane:EA 1:2 to give 4-benzyloxy-3-ethyl-N-[2-(2-isobutyl-6-methyl-pyridin-4-yl)-2-oxo-ethyl]-5-methyl-benzamide (35 mg) as a yellow wax; LC-MS: $t_R$=1.03*, [M+1]⁺=458.91.

h) To a solution 4-benzyloxy-3-ethyl-N-[2-(2-isobutyl-6-methyl-pyridin-4-yl)-2-oxo-ethyl]-5-methyl-benzamide (70 mg, 0.153 mmol) in THF (2 mL), Burgess reagent (95 mg, 0.377 mmol) is added and the mixture is refluxed for 2 h. Another portion of Burgess reagent (50 mg, 0.231 mmol) is added and stirring is continued at rt for 16 h. The solvent is evaporated and the crude product is purified on prep. TLC with heptane:EA 1:2 to give 4-[2-(4-benzyloxy-3-ethyl-5-methyl-phenyl)-oxazol-5-yl]-2-isobutyl-6-methyl-pyridine (24 mg) as a yellow oil; LC-MS: $t_R$=1.33*, [M+1]⁺=441.04.

i) To a solution of 4-[2-(4-benzyloxy-3-ethyl-5-methyl-phenyl)-oxazol-5-yl]-2-isobutyl-6-methyl-pyridine (29 mg, 66 µmol) in THF (0.5 mL) and EtOH (0.5 mL), Pd/C (10 mg, 10% Pd) is added. The mixture is stirred at rt under 1 bar of H₂ for 16 h. The catalyst is filtered off and the filtrate is concentrated. The residue is again treated with Pd/C and H₂ at rt for 24 h as described before. The catalyst is filtered off and the filtrate is evaporated. The crude product is purified on prep. TLC using heptane:EA 1:1 to give 2-ethyl-4-[5-(2-isobutyl-6-methyl-pyridin-4-yl)-oxazol-2-yl]-6-methyl-phenol (11 mg) as a pale yellow glass; LC-MS: $t_R$=0.97*, [M+1]⁺=351.11; ¹H NMR (CDCl₃): δ 0.99 (d, J=6.5 Hz, 6 H), 1.33 (t, J=7.5 Hz, 3 H), 2.12-2.22 (m, 1 H), 2.37 (s, 3 H), 2.63 (s, 3 H), 2.66-2.79 (m, 4 H), 5.35 (s br, 1 H), 7.21 (s, 1 H), 7.29 (s, 1H), 7.58 (s, 1 H), 7.80 (s, 2 H).

Example 235

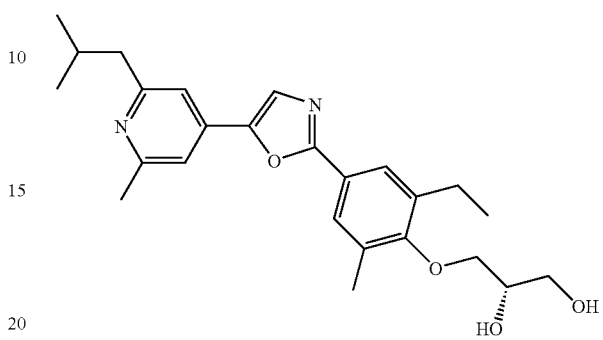

(S)-3-{2-Ethyl-4-[5-(2-isobutyl-6-methyl-pyridin-4-yl)-oxazol-2-yl]-6-methyl-phenoxy}-propane-1,2-diol is prepared from Example 234 in analogy to Example 14; LC-MS: $t_R$=0.88*, [M+1]⁺=424.92; ¹H NMR δ 0.99 (d, J=6.5 Hz, 6 H), 1.33 (t, J=7.5 Hz, 3 H), 2.13-2.23 (m, 1 H), 2.42 (s, 3 H), 2.63 (s, 3 H), 2.71 (d, J=7.3 Hz, 2 H), 2.77 (q, J=7.5 Hz, 2 H), 3.50-3.71 (m, 1 H), 3.82-3.98 (m, 4 H), 4.15-4.21 (m, 1 H), 7.21 (s, 1 H), 7.29 (s, 1 H), 7.60 (s, 1 H), 7.83 (s, 1 H), 7.85 (s, 1 H).

Example 236

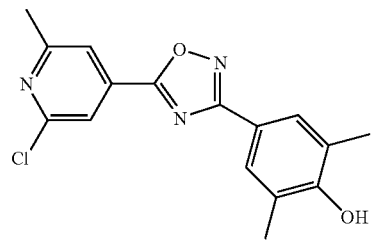 [SMILES: Cc1cc(-c2nc(-c3cc(C)c(O)c(C)c3)no2)cc(Cl)n1]

4-[5-(2-Chloro-6-methyl-pyridin-4-yl)-[1,2,4]oxadiazol-3-yl]-2,6-dimethyl-phenol is prepared in analogy to Example 10 starting from isonicotinic acid 1 and 4,N-dihydroxy-3,5-dimethyl-benzamidine; LC-MS: $t_R$=1.03, [M+1]⁺=316.20.

Example 237

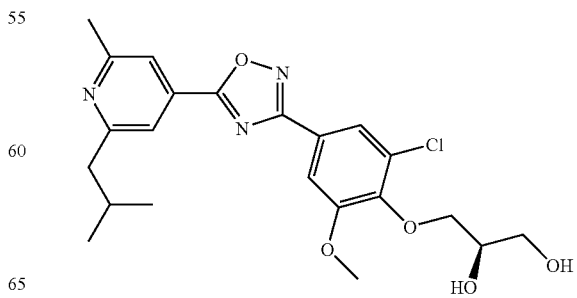

(R)-3-{2-Ethyl-4-[5-(2-isobutyl-6-methyl-pyridin-4-yl)-[1,2,4]oxadiazol-3-yl]-6-methyl-phenoxy}-propane-1,2-diol is prepared in analogy to Example 14 from Example 150; LC-MS: $t_R$=0.82, [M+1]$^+$=448.13.

Example 238

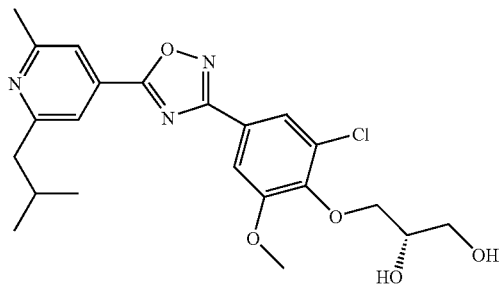 [SMILES: COc1cc(-c2noc(-c3cc(C)nc(CC(C)C)c3)n2)cc(Cl)c1OC[C@@H](O)CO]

(S)-3-{2-Ethyl-4-[5-(2-isobutyl-6-methyl-pyridin-4-yl)-[1,2,4]oxadiazol-3-yl]-6-methyl-phenoxy}-propane-1,2-diol is prepared in analogy to Example 14 from Example 150; LC-MS: $t_R$=0.82, [M+1]$^+$=448.10.

Example 239

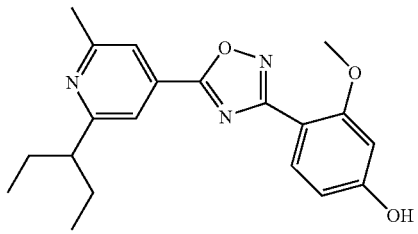 [SMILES: CCC(CC)c1cc(-c2nc(-c3ccc(O)cc3OC)no2)cc(C)n1]

4-{5-[2-(1-Ethyl-propyl)-6-methyl-pyridin-4-yl]-[1,2,4]oxadiazol-3-yl}-3-methoxy-Phenol is prepared in analogy to Example 10 starting from isonicotinic acid 14 and 4,N-dihydroxy-2-methoxy-benzamidine; LC-MS: $t_R$=0.80, [M+1]$^+$=354.13.

Example 240

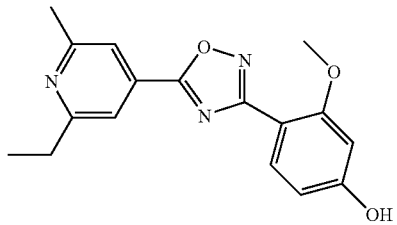 [SMILES: CCc1cc(-c2nc(-c3ccc(O)cc3OC)no2)cc(C)n1]

4-[5-(2-Ethyl-6-methyl-pyridin-4-yl)-[1,2,4]oxadiazol-3-yl]-3-methoxy-phenol is pre-pared in analogy to Example 10 starting from isonicotinic acid 4 and 4,N-dihydroxy-2-methoxy-benzamidine; LC-MS: $t_R$=0.80, [M+1]$^+$=354.13.

Example 241

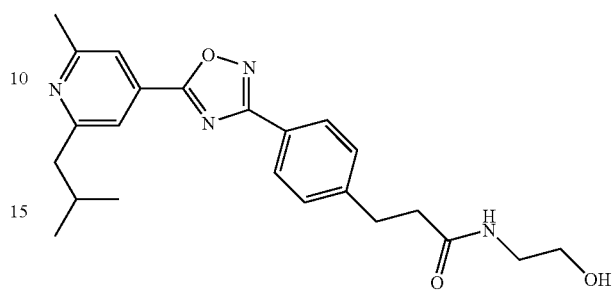

N-(2-Hydroxy-ethyl)-2-{4-[5-(2-isobutyl-6-methyl-pyridin-4-yl)-[1,2,4]oxadiazol-3-yl]-phenyl}-acetamide is prepared from {4-[5-(2-isobutyl-6-methyl-pyridin-4-yl)-[1,2,4]oxadiazol-3-yl]-phenyl}-acetic acid and ethanolamine in analogy to Example 65; LC-MS: $t_R$=0.77, [M+1]$^+$=395.19.

Example 242

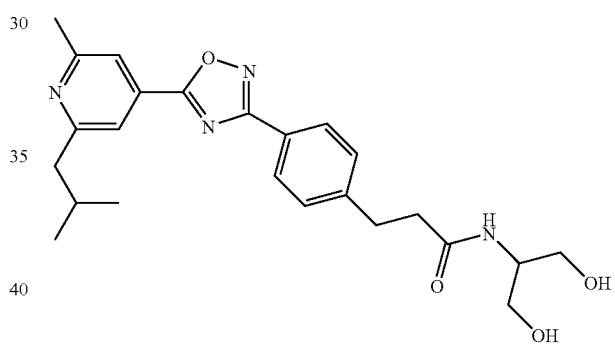

N-(2-Hydroxy-1-hydroxymethyl-ethyl)-2-{4-[5-(2-isobutyl-6-methyl-pyridin-4-yl)-[1,2,4]oxadiazol-3-yl]-phenyl}-acetamide is prepared from {4-[5-(2-isobutyl-6-methyl-pyridin-4-yl)-[1,2,4]oxadiazol-3-yl]-phenyl}-acetic acid and 2-amino-propane-1,3-diol in analogy to Example 65; LC-MS: $t_R$=0.73, [M+1-1]$^+$=425.06.

Example 243

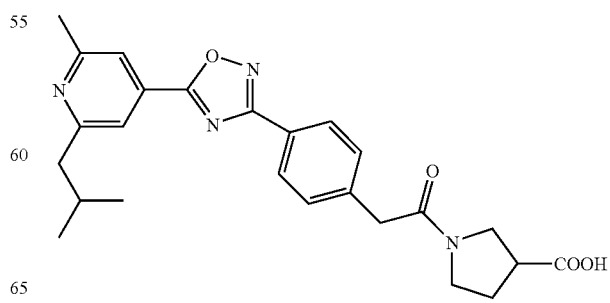

(RS)-1-(2-{4-[5-(2-Isobutyl-6-methyl-pyridin-4-yl)-[1,2,4]oxadiazol-3-yl]-phenyl}-acetyl)-pyrrolidine-3-carboxylic acid is prepared from {4-[5-(2-isobutyl-6-methyl-pyridin-4-yl)-[1,2,4]oxadiazol-3-yl]-phenyl}-acetic acid and (RS)-pyrrolidine-3-carboxylic acid hydrochloride in analogy to Example 65; LC-MS: $t_R$=0.82, $[M+1]^+$=448.10.

Example 244

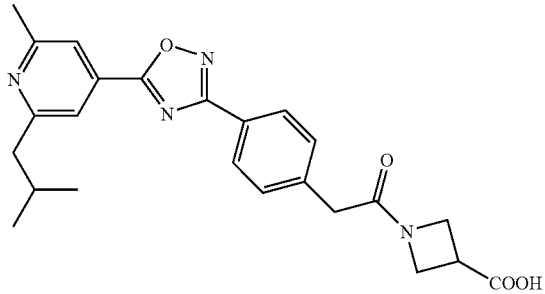 [SMILES: Cc1cc(-c2nc(-c3ccc(CC(=O)N4CC(C(=O)O)C4)cc3)no2)cc(CC(C)C)n1]

1-(2-{4-[5-(2-Isobutyl-6-methyl-pyridin-4-yl)-[1,2,4]oxadiazol-3-yl]-phenyl}-acetyl)-azetidine-3-carboxylic acid methyl ester is prepared from {4-[5-(2-isobutyl-6-methyl-pyridin-4-yl)-[1,2,4]oxadiazol-3-yl]-phenyl}-acetic acid and azetidine-3-carboxylic acid methyl ester in analogy to Example 65; stirring this material in 3 N aq. NaOH/dioxane at rt for 20 h gives 1-(2-{4-[5-(2-isobutyl-6-methyl-pyridin-4-yl)-[1,2,4]oxadiazol-3-yl]-phenyl}-acetyl)-azetidine-3-carboxylic acid; LC-MS: $t_R$=0.80, $[M+1]^+$=435.02.

II) Biology i) GTPγS assay to determine $EC_{50}$ values

GTPγS binding assays are performed in 96 well microtiter plates (Nunc, 442587) in a final volume of 200 μl, using membrane preparations of CHO cells expressing recombinant human S1P1 receptor. Assay conditions are 20 mM Hepes (Fluka, 54461), 100 mM NaCl (Fluka, 71378), 5 mM $MgCl_2$ (Fluka, 63064), 0.1% BSA (Calbiochem, 126609), 1 μM GDP (Sigma, G-7127), 2.5% DMSO (Fluka, 41644), 50 pM $^{35}$S-GTPγS (Amersham Biosciences, SJ1320). The pH is 7.4. Test compounds are dissolved and diluted in 100% DMSO and pre-incubated at room temperature for 30 min in 150 μl of the above assay buffer, in the absence of $^{35}$S-GTPγS. After addition of 50 μl of $^{35}$S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM $Na_2HPO_4/NaH_2PO_4$ (70%/30%), dried, sealed at the bottom and, after addition of 25 μl MicroScint20 (Packard Biosciences, order#6013621), sealed on the top. Membrane-bound $^{35}$S-GTPγS is measured with a TopCount from Packard Biosciences.

$EC_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 μM of S1P. Non-specific binding is the amount of binding in the absence of an agonist in the assay.

Agonistic activities ($EC_{50}$ values) of 163 from 244 exemplified compounds have been measured. $EC_{50}$ values of 161 compounds are in the range of 0.1 to 2480 nM with an average of 73 nM. Agonistic activities of selected compounds are displayed in Table 1.

TABLE 1

| Compound of Example | $EC_{50}$ [nM] |
|---|---|
| 4 | 0.7 |
| 11 | 0.2 |
| 26 | 0.4 |
| 27 | 2.5 |
| 41 | 2.0 |
| 60 | 0.5 |
| 74 | 4.3 |
| 86 | 5.6 |
| 95 | 0.4 |
| 101 | 0.4 |
| 111 | 1.8 |
| 123 | 0.4 |
| 145 | 0.2 |
| 160 | 0.7 |
| 180 | 0.8 |
| 196 | 0.6 |
| 226 | 0.9 |
| 232 | 1.8 |
| 235 | 5.8 | ii) Assessment of In vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zurich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when $p<0.05$.

As an example, Table 2 shows the effect on lymphocyte counts 6 h after oral administration of 10 mg/kg of a compound of the present invention to normotensive male Wistar rats as compared to a group of animals treated with vehicle only. Lymphocyte counts 6 h after oral administration have been measured for 51 from 244 exemplified compounds (one being dosed at 3 mg/kg) and are in the range of −78% to −53% with an average of −67%.

TABLE 2

| Compound of Example | Lymphocyte counts |
|---|---|
| 8 | −62% |
| 9 | −67% |
| 30 | −73% |
| 57 | −74% |
| 115 | −78% |
| 119 | −68% |
| 130 | −72% |
| 134 | −53% |
| 159 | −74% |
| 164 | −73% |
| 229 | −65% |

The invention claimed is:
1. A compound of the Formula (I),

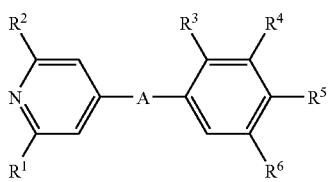

Formula (I)

wherein
A represents

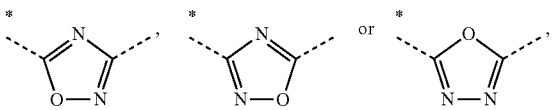

wherein the asterisks indicate the bond that is linked to the pyridine group of Formula (I);
$R^1$ represents $C_{1-4}$-alkyl, or chloro;
$R^2$ represents $C_{1-5}$-alkyl, $C_{1-4}$-alkoxy, or $C_{3-6}$-cycloalkyl;
$R^3$ represents hydrogen, $C_{1-4}$-alkyl, $C_{1-4}$-alkoxy, or halogen;
$R^4$ represents hydrogen, $C_{1-4}$-alkyl, $C_{1-4}$-alkoxy, halogen, trifluoromethyl, or trifluoromethoxy;
$R^5$ represents 2,3-dihydroxypropyl, di-(hydroxy-$C_{1-4}$-alkyl)-$C_{1-4}$-alkyl, —$CH_2$—$(CH_2)_k$—$NHSO_2R^{53}$, —$(CH_2)_n CH(OH)$—$CH_2$—$NHSO_2R^{53}$, —$CH_2$—$(CH_2)_k$—$NHCOR^{54}$, —$(CH_2)_n CH(OH)$—$CH_2$—$NHCOR^{54}$, —$CH_2$—$(CH_2)_n$—$CONR^{51}R^{52}$, —CO—$NHR^{51}$, —$(CH_2)_n CH(OH)$—$CH_2$—$NR^{51}R^{52}$, hydroxy, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{51}R^{52}$, —$OCH_2$—$CH(OH)$—$CH_2$—$NR^{51}R^{52}$, —$OCH_2$—$(CH_2)_m$—$NHSO_2R^{53}$, —$OCH_2$—$CH(OH)$—$CH_2$—$NHSO_2R^{53}$, —$OCH_2$—$(CH_2)_m$—$NHCOR^{54}$, —$OCH_2$—$CH(OH)$—$CH_2$—$NHCOR^{54}$;
$R^{51}$ represents hydrogen, $C_{1-3}$-alkyl, 2-hydroxyethyl, 2-hydroxy-1-hydroxymethyl-ethyl, 2,3-dihydroxypropyl, carboxymethyl, 1-($C_{1-5}$-alkylcarboxy)methyl, 2-carboxyethyl, or 2-($C_{1-5}$-alkylcarboxy)ethyl;
$R^{52}$ represents hydrogen, methyl, or ethyl;
$R^{53}$ represents $C_{1-3}$-alkyl, methylamino, ethylamino, or dimethylamino;
$R^{54}$ represents hydroxymethyl, hydroxyethyl, aminomethyl, methylaminomethyl, dimethylaminomethyl, aminoethyl, 2-methylamino-ethyl, or 2-dimethylamino-ethyl;
k represents the integer 1, 2, or 3;
m represents the integer 1 or 2;
n represents 0, 1, or 2; and
$R^6$ represents hydrogen, $C_{1-4}$-alkyl, or halogen;
in free or salt form.

2. The compound according to claim 1, wherein A represents

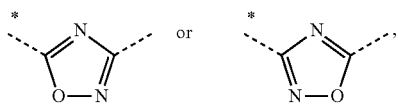

wherein the asterisks indicate the bond that is linked to the pyridine group of Formula (I); in free or salt form.

3. The compound according to claim 1, wherein A represents

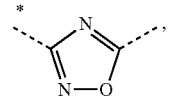

wherein the asterisks indicate the bond that is linked to the pyridine group of Formula (I); in free or salt form.

4. The compound according to claim 1, wherein A represents

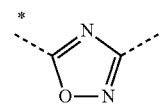

wherein the asterisk indicates the bond that is linked to the pyridine group of Formula (I), in free or salt form.

5. The compound according to claim 1, wherein $R^1$ represents $C_{1-4}$-alkyl; in free or salt form.

6. The compound according to claim 1, wherein $R^1$ represents methyl or ethyl; in free or salt form.

7. The compound according to claim 1, wherein $R^1$ represents methyl; in free or salt form.

8. The compound according to claim 1, wherein $R^2$ represents $C_{1-5}$-alkyl, $C_{1-3}$-alkoxy, or cyclopentyl; in free or salt form.

9. The compound according to claim 1, wherein $R^2$ represents $C_{2-5}$-alkyl; in free or salt form.

10. The compound according to claim 1, wherein $R^2$ represents ethyl, n-propyl, isopropyl, isobutyl, or 3-pentyl; in free or salt form.

11. The compound according to claim 1, wherein at least one of $R^3$, $R^4$ and $R^6$ represents a group other than hydrogen; in free or salt form.

12. The compound according to claim 1, wherein $R^3$ represents hydrogen; in free or salt form.

13. The compound according to claim 1, wherein $R^3$ represents hydrogen; and $R^4$ represents $C_{1-4}$-alkyl, or $C_{1-4}$-alkoxy; and $R^6$ represents $C_{1-4}$-alkyl, or halogen; in free or salt form.

14. The compound according to claim 1, wherein $R^3$ represents hydrogen; and $R^4$ represents $C_{1-3}$-alkyl, or methoxy; and $R^6$ represents methyl, ethyl, or chloro; in free or salt form.

15. The compound according to claim 1, wherein $R^5$ represents 2,3-dihydroxypropyl, —$CH_2$—$(CH_2)_k$—$NHCOR^{54}$, —$(CH_2)_n CH(OH)$—$CH_2$—$NHCOR^{54}$, —$CH_2$—$(CH_2)_n$—$CONR^{51}R^{52}$, —CO—$NHR^{51}$, —$(CH_2)_n CH(OH)$—$CH_2$—$NR^{51}R^{52}$, hydroxy-$C_{2-5}$-alkoxy, di-(hydroxy-$C_{1-4}$-alkyl)-$C_{1-4}$-alkoxy, 2,3-dihydroxy-propoxy, 2-hydroxy-3-methoxy-propoxy, —$OCH_2$—$(CH_2)_m$—$NR^{51}R^{52}$, —$OCH_2$—$CH(OH)$—$CH_2$—$NR^{51}R^{52}$, —$OCH_2$—$(CH_2)_m$—$NHCOR^{54}$, or —$OCH_2$—$CH(OH)$—$CH_2$—$NHCOR^{54}$; in free or salt form.

16. The compound according to claim 1, wherein $R^5$ represents 3-hydroxy-2-hydroxymethyl-propoxy, 2,3-dihydroxy-propoxy or —$OCH_2$—$CH(OH)$—$CH_2$—$NHCOR^{54}$; in free or salt form.

17. The compound according to claim 1 selected from the group consisting of:
N-(3-{4-[5-(2-Chloro-6-methyl-pyridin-4-yl)-[1,2,4]oxadiazol-3-yl]-2,6-dimethyl-phenoxy}-2-hydroxy-propyl)-2-hydroxy-acetamide;

3-{4-[5-(2-Chloro-6-isobutyl-pyridin-4-yl)-[1,2,4]oxadiazol-3-yl]-2,6-dimethyl-phenoxy}-propane-1,2-diol;

N-(3-{4-[5-(2-Chloro-6-isobutyl-pyridin-4-yl)-[1,2,4]oxadiazol-3-yl]-2,6-dimethyl-phenoxy}-2-hydroxy-propyl)-2-hydroxy-acetamide;

3-{4-[5-(2-Ethyl-6-methyl-pyridin-4-yl)-[1,2,4]oxadiazol-3-yl]-2,6-dimethyl-phenoxy}-propane-1,2-diol;

3-{4-[5-(2-Isobutyl-6-methyl-pyridin-4-yl)-[1,2,4]oxadiazol-3-yl]-2,6-dimethyl-phenoxy}-propane-1,2-diol;

2-Hydroxy-N-(2-hydroxy-3-{4-[5-(2-isobutyl-6-methyl-pyridin-4-yl)1,2,4]oxadiazol-3-yl]-2,6-dimethyl-phenoxy}-propyl)-acetamide;

3-{2-Ethyl-4-[5-(2-isobutyl-6-methyl-pyridin-4-yl)1,2,4]oxadiazol-3-yl]-6-methyl-phenoxy}-propane-1,2-diol;

2-Ethyl-4-[5-(2-isobutyl-6-methyl-pyridin-4-yl)-[1,2,4]oxadiazol-3-yl]-6-methyl-phenol;

(R)-3-{2-Ethyl-4-[5-(2-isobutyl-6-methyl-pyridin-4-yl)-[1,2,4]oxadiazol-3-yl]-6-methyl-phenoxy}-propane-1,2-diol;

(S)-3-{2-Ethyl-4-[5-(2-isobutyl-6-methyl-pyridin-4-yl)-[1,2,4]oxadiazol-3-yl]-6-methyl-phenoxy}-propane-1,2-diol;

2-{2-Ethyl-4-[5-(2-isobutyl-6-methyl-pyridin-4-yl)-[1,2,4]oxadiazol-3-yl]-6-methyl-phenoxymethyl}-propane-1,3-diol;

2-{2-Ethyl-4-[5-(2-isobutyl-6-methyl-pyridin-4-yl)-[1,2,4]oxadiazol-3-yl]-6-methyl-phenoxy}-ethanol;

3-{2-Ethyl-4-[5-(2-isobutyl-6-methyl-pyridin-4-yl)-[1,2,4]oxadiazol-3-yl]-6-methyl-phenoxy}-propan-1-ol;

N-(3-{2-Ethyl-4-[5-(2-isobutyl-6-methyl-pyridin-4-yl)-[1,2,4]oxadiazol-3-yl]-6-methyl-phenoxy}-2-hydroxy-propyl)-2-hydroxy-acetamide;

3-{4-[5-(2,6-Diisobutyl-pyridin-4-yl)-[1,2,4]oxadiazol-3-yl]-2,6-dimethyl-phenoxy}-propane-1,2-diol;

3-{4-[5-(2-Chloro-6-isopropoxy-pyridin-4-yl)-[1,2,4]oxadiazol-3-yl]-2,6-dimethyl-phenoxy}-propane-1,2-diol;

N-(3-{4-[5-(2-Chloro-6-isopropoxy-pyridin-4-yl)-[1,2,4]oxadiazol-3-yl]-2,6-dimethyl-phenoxy}-2-hydroxy-propyl)-2-hydroxy-acetamide;

3-{4-[5-(2-Ethoxy-6-methyl-pyridin-4-yl)-[1,2,4]oxadiazol-3-yl]-2,6-dimethyl-phenoxy}-propane-1,2-diol;

3-{4-[5-(2-Isopropoxy-6-methyl-pyridin-4-yl)-[1,2,4]oxadiazol-3-yl]-2,6-dimethyl-phenoxy}-propane-1,2-diol;

2-Hydroxy-N-(2-hydroxy-3-{4-[5-(2-isopropoxy-6-methyl-pyridin-4-yl)-[1,2,4]oxadiazol-3-yl]-2,6-dimethyl-phenoxy}-propyl)-acetamide;

4-[5-(2-Ethyl-6-methyl-pyridin-4-yl)-[1,2,4]oxadiazol-3-yl]-2,6-dimethyl-phenol;

(R)-3-{4-[5-(2-Ethyl-6-methyl-pyridin-4-yl)-[1,2,4]oxadiazol-3-yl]-2,6-dimethyl-phenoxy}-propane-1,2-diol;

(R)-3-{2-Chloro-4-[5-(2-ethyl-6-methyl-pyridin-4-yl)-[1,2,4]oxadiazol-3-yl]-6-methyl-phenoxy}-propane-1,2-diol;

(S)-3-{4-[5-(2-Ethyl-6-methyl-pyridin-4-yl)-[1,2,4]oxadiazol-3-yl]-2,6-dimethyl-phenoxy}-propane-1,2-diol;

(S)-3-{2-Chloro-4-[5-(2-ethyl-6-methyl-pyridin-4-yl)-[1,2,4]oxadiazol-3-yl]-6-methyl-phenoxy}-propane-1,2-diol;

(S)-3-{2-Chloro-4-[5-(2-ethyl-6-methyl-pyridin-4-yl)-[1,2,4]oxadiazol-3-yl]-6-methoxy-phenoxy}-propane-1,2-diol;

N-(3-{4-[5-(2-Ethyl-6-methyl-pyridin-4-yl)-[1,2,4]oxadiazol-3-yl]-2,6-dimethyl-phenoxy}-2-hydroxy-propyl)-2-hydroxy-acetamide;

N-((R)-3-{2-Ethyl-4-[5-(2-ethyl-6-methyl-pyridin-4-yl)-[1,2,4]oxadiazol-3-yl]-6-methyl-phenoxy}-2-hydroxy-propyl)-2-hydroxy-acetamide;

N-((S)-3-{2-Ethyl-4-[5-(2-ethyl-6-methyl-pyridin-4-yl)-[1,2,4]oxadiazol-3-yl]-6-methyl-phenoxy}-2-hydroxy-propyl)-2-hydroxy-acetamide;

N-(3-{4-[5-(2-Ethyl-6-methyl-pyridin-4-yl)-[1,2,4]oxadiazol-3-yl]-2-methyl-6-propyl-phenoxy}-2-hydroxy-propyl)-2-hydroxy-acetamide;

N-((S)-3-{4-[5-(2-Ethyl-6-methyl-pyridin-4-yl)-[1,2,4]oxadiazol-3-yl]-2-methyl-6-propyl-phenoxy}-2-hydroxy-propyl)-2-hydroxy-acetamide;

N-((R)-3-{2-Chloro-4-[5-(2-ethyl-6-methyl-pyridin-4-yl)-[1,2,4]oxadiazol-3-yl]-6-methyl-phenoxy}-2-hydroxy-propyl)-2-hydroxy-acetamide;

N-((S)-3-{2-Chloro-4-[5-(2-ethyl-6-methyl-pyridin-4-yl)-[1,2,4]oxadiazol-3-yl]-6-methyl-phenoxy}-2-hydroxy-propyl)-2-hydroxy-acetamide;

N-((R)-3-{2-Chloro-4-[5-(2-ethyl-6-methyl-pyridin-4-yl)-[1,2,4]oxadiazol-3-yl]-6-methoxy-phenoxy}-2-hydroxy-propyl)-2-hydroxy-acetamide;

N-((S)-3-{2-Chloro-4-[5-(2-ethyl-6-methyl-pyridin-4-yl)-[1,2,4]oxadiazol-3-yl]-6-methoxy-phenoxy}-2-hydroxy-propyl)-2-hydroxy-acetamide;

N-(3-{4-[5-(2-Ethyl-6-methyl-pyridin-4-yl)-[1,2,4]oxadiazol-3-yl]-2-methoxy-6-methyl-phenoxy}-2-hydroxy-propyl)-2-hydroxy-acetamide;

N-((S)-3-{2-Ethyl-4-[3-(2-ethyl-6-methyl-pyridin-4-yl)-[1,2,4]oxadiazol-5-yl]-6-methyl-phenoxy}-2-hydroxy-propyl)-2-hydroxy-acetamide;

N-((S)-3-{4-[5-(2-Ethyl-6-methyl-pyridin-4-yl)-[1,3,4]oxadiazol-2-yl]-2,6-dimethyl-phenoxy}-2-hydroxy-propyl)-2-hydroxy-acetamide;

2,6-Dimethyl-4-[5-(2-methyl-6-propyl-pyridin-4-yl)-[1,2,4]oxadiazol-3-yl]-phenol;

2-Ethyl-6-methyl-4-[5-(2-methyl-6-propyl-pyridin-4-yl)-[1,2,4]oxadiazol-3-yl]-phenol;

(R)-3-{2,6-Dimethyl-4-[5-(2-methyl-6-propyl-pyridin-4-yl)-[1,2,4]oxadiazol-3-yl]-phenoxy}-propane-1,2-diol;

(S)-3-{2,6-Dimethyl-4-[5-(2-methyl-6-propyl-pyridin-4-yl)-[1,2,4]oxadiazol-3-yl]-phenoxy}-propane-1,2-diol;

(R)-3-{2-Ethyl-6-methyl-4-[5-(2-methyl-6-propyl-pyridin-4-yl)-[1,2,4]oxadiazol-3-yl]-phenoxy}-propane-1,2-diol;

(S)-3-{2-Ethyl-6-methyl-4-[5-(2-methyl-6-propyl-pyridin-4-yl)-[1,2,4]oxadiazol-3-yl]-phenoxy}-propane-1,2-diol;

(R)-3-{2-Chloro-6-methoxy-4-[5-(2-methyl-6-propyl-pyridin-4-yl)-[1,2,4]oxadiazol-3-yl]-phenoxy}-propane-1,2-diol;

(S)-3-{2-Chloro-6-methoxy-4-[5-(2-methyl-6-propyl-pyridin-4-yl)-[1,2,4]oxadiazol-3-yl]-phenoxy}-propane-1,2-diol;

N-(3-{2,6-Dimethyl-4-[5-(2-methyl-6-propyl-pyridin-4-yl)-[1,2,4]oxadiazol-3-yl]-phenoxy}-2-hydroxy-propyl)-2-hydroxy-acetamide;

N-((S)-3-{2,6-Dimethyl-4-[5-(2-methyl-6-propyl-pyridin-4-yl)-[1,2,4]oxadiazol-3-yl]-phenoxy}-2-hydroxy-propyl)-2-hydroxy-acetamide;

N-((R)-3-{2-Ethyl-6-methyl-4-[5-(2-methyl-6-propyl-pyridin-4-yl)-[1,2,4]oxadiazol-3-yl]-phenoxy}-2-hydroxy-propyl)-2-hydroxy-acetamide;

N-((S)-3-{2-Ethyl-6-methyl-4-[5-(2-methyl-6-propyl-pyridin-4-yl)-[1,2,4]oxadiazol-3-yl]-phenoxy}-2-hydroxy-propyl)-2-hydroxy-acetamide;

N-((R)-3-{2-Chloro-6-methoxy-4-[5-(2-methyl-6-propyl-pyridin-4-yl)-[1,2,4]oxadiazol-3-yl]-phenoxy}-2-hydroxy-propyl)-2-hydroxy-acetamide;

N-((S)-3-{2,6-Dimethyl-4-[5-(2-methyl-6-propyl-pyridin-4-yl)-[1,3,4]oxadiazol-2-yl]-phenoxy}-2-hydroxy-propyl)-2-hydroxy-acetamide;

N-((R)-3-{2-Ethyl-6-methyl-4-[5-(2-methyl-6-propyl-pyridin-4-yl)-[1,3,4]oxadiazol-2-yl]-phenoxy}-2-hydroxy-propyl)-2-hydroxy-acetamide;

N-((S)-3-{2-Ethyl-6-methyl-4-[5-(2-methyl-6-propyl-pyridin-4-yl)-[1,3,4]oxadiazol-2-yl]-phenoxy}-2-hydroxy-propyl)-2-hydroxy-acetamide;

2-{2-Ethyl-4-[5-(2-isopropyl-6-methyl-pyridin-4-yl)-[1,2,4]oxadiazol-3-yl]-6-methyl-phenoxy}-ethanol;

(S)-3-{2-Ethyl-4-[5-(2-isopropyl-6-methyl-pyridin-4-yl)-[1,2,4]oxadiazol-3-yl]-6-methyl-phenoxy}-propane-1,2-diol;

N-(3-{2-Ethyl-4-[5-(2-isopropyl-6-methyl-pyridin-4-yl)-[1,2,4]oxadiazol-3-yl]-6-methyl-phenoxy}-2-hydroxy-propyl)-2-hydroxy-acetamide;

2-Hydroxy-N-((S)-2-hydroxy-3-{4-[5-(2-isopropyl-6-methyl-pyridin-4-yl)-[1,2,4]oxadiazol-3-yl]-2-methyl-6-propyl-phenoxy}-propyl)-acetamide;

3-{2-Chloro-4-[5-(2-isobutyl-6-methyl-pyridin-4-yl)-[1,2,4]oxadiazol-3-yl]-6-methyl-phenoxy}-propane-1,2-diol;

3-{2-Chloro-4-[5-(2-isobutyl-6-methyl-pyridin-4-yl)-[1,2,4]oxadiazol-3-yl]-6-methoxy-phenoxy}-propane-1,2-diol;

3-{2-Bromo-4-[5-(2-isobutyl-6-methyl-pyridin-4-yl)-[1,2,4]oxadiazol-3-yl]-phenoxy}-propane-1,2-diol;

1-{2-Chloro-4-[5-(2-isobutyl-6-methyl-pyridin-4-yl)-[1,2,4]oxadiazol-3-yl]-6-methoxy-phenoxy}-3-(2-hydroxy-ethylamino)-propan-2-ol;

2-Hydroxy-N-(2-hydroxy-3-{4-[5-(2-isobutyl-6-methyl-pyridin-4-yl)-[1,2,4]oxadiazol-3-yl]-3-methyl-phenoxy}-propyl)-acetamide;

N-(3-{2-Chloro-4-[5-(2-isobutyl-6-methyl-pyridin-4-yl)-[1,2,4]oxadiazol-3-yl]-6-methyl-phenoxy}-2-hydroxy-propyl)-2-hydroxy-acetamide;

N-(3-{2-Chloro-4-[5-(2-isobutyl-6-methyl-pyridin-4-yl)-[1,2,4]oxadiazol-3-yl]-6-methoxy-phenoxy}-2-hydroxy-propyl)-2-hydroxy-acetamide;

2-Chloro-4-[5-(2-isobutyl-6-methyl-pyridin-4-yl)-[1,2,4]oxadiazol-3-yl]-6-methoxy-phenol;

(S)-3-{4-[5-(2-Isobutyl-6-methyl-pyridin-4-yl)-[1,2,4]oxadiazol-3-yl]-2-methyl-6-propyl-phenoxy}-propane-1,2-diol;

2-Hydroxy-N-(2-hydroxy-3-{4-[5-(2-isobutyl-6-methyl-pyridin-4-yl)-[1,2,4]oxadiazol-3-yl]-3-methoxy-phenoxy}-propyl)-acetamide;

2-Hydroxy-N-((S)-2-hydroxy-3-{4-[5-(2-isobutyl-6-methyl-pyridin-4-yl)-[1,2,4]oxadiazol-3-yl]-2-methyl-6-propyl-phenoxy}-propyl)-acetamide;

2-Hydroxy-N-(2-hydroxy-3-{4-[5-(2-isobutyl-6-methyl-pyridin-4-yl)-[1,2,4]oxadiazol-3-yl]-2-methoxy-6-methyl-phenoxy}-propyl)-acetamide;

N-((R)-3-{2-Chloro-4-[5-(2-isobutyl-6-methyl-pyridin-4-yl)-[1,2,4]oxadiazol-3-yl]-6-methoxy-phenoxy}-2-hydroxy-propyl)-2-hydroxy-acetamide;

N-((S)-3-{2-Chloro-4-[5-(2-isobutyl-6-methyl-pyridin-4-yl)-[1,2,4]oxadiazol-3-yl]-6-methoxy-phenoxy}-2-hydroxy-propyl)-2-hydroxy-acetamide;

(R)-3-{2-Ethyl-4-[3-(2-isobutyl-6-methyl-pyridin-4-yl)-[1,2,4]oxadiazol-5-yl]-6-methyl-phenoxy}-propane-1,2-diol;

(S)-3-{2-Ethyl-4-[3-(2-isobutyl-6-methyl-pyridin-4-yl)-[1,2,4]oxadiazol-5-yl]-6-methyl-phenoxy}-propane-1,2-diol;

2-Hydroxy-N-((R)-2-hydroxy-3-{4-[5-(2-isobutyl-6-methyl-pyridin-4-yl)-[1,3,4]oxadiazol-2-yl]-2,6-dimethyl-phenoxy}-propyl)-acetamide;

2-Hydroxy-N-((S)-2-hydroxy-3-{4-[5-(2-isobutyl-6-methyl-pyridin-4-yl)-[1,3,4]oxadiazol-2-yl]-2,6-dimethyl-phenoxy}-propyl)-acetamide;

N-((R)-3-{2-Ethyl-4-[5-(2-isobutyl-6-methyl-pyridin-4-yl)-[1,3,4]oxadiazol-2-yl]-6-methyl-phenoxy}-2-hydroxy-propyl)-2-hydroxy-acetamide;

N-((S)-3-{2-Ethyl-4-[5-(2-isobutyl-6-methyl-pyridin-4-yl)-[1,3,4]oxadiazol-2-yl]-6-methyl-phenoxy}-2-hydroxy-propyl)-2-hydroxy-acetamide;

N-((S)-3-{2-Chloro-4-[5-(2-isobutyl-6-methyl-pyridin-4-yl)-[1,3,4]oxadiazol-2-yl]-6-methoxy-phenoxy}-2-hydroxy-propyl)-2-hydroxy-acetamide;

2-Ethyl-4-{5-[2-(1-ethyl-propyl)-6-methyl-pyridin-4-yl]-[1,2,4]oxadiazol-3-yl}-6-methyl-phenol;

(R)-3-(2-Ethyl-4-{5-[2-(1-ethyl-propyl)-6-methyl-pyridin-4-yl]-[1,2,4]oxadiazol-3-yl}-6-methyl-phenoxy)-propane-1,2-diol;

(S)-3-(2-Ethyl-4-{5-[2-(1-ethyl-propyl)-6-methyl-pyridin-4-yl]-[1,2,4]oxadiazol-3-yl}-6-methyl-phenoxy)-propane-1,2-diol;

(R)-3-(4-{5-[2-(1-Ethyl-propyl)-6-methyl-pyridin-4-yl]-[1,2,4]oxadiazol-3-yl}-2-methyl-6-propyl-phenoxy)-propane-1,2-diol;

(S)-3-(4-{5-[2-(1-Ethyl-propyl)-6-methyl-pyridin-4-yl]-[1,2,4]oxadiazol-3-yl}-2-methyl-6-propyl-phenoxy)-propane-1,2-diol;

N-[(R)-3-(2-Ethyl-4-{5-[2-(1-ethyl-propyl)-6-methyl-pyridin-4-yl]-[1,2,4]oxadiazol-3-yl}-6-methyl-phenoxy)-2-hydroxy-propyl]-2-hydroxy-acetamide;

N-[(S)-3-(2-Ethyl-4-{5-[2-(1-ethyl-propyl)-6-methyl-pyridin-4-yl]-[1,2,4]oxadiazol-3-yl}-6-methyl-phenoxy)-2-hydroxy-propyl]-2-hydroxy-acetamide;

N-[(R)-3-(4-{5-[2-(1-Ethyl-propyl)-6-methyl-pyridin-4-yl]-[1,2,4]oxadiazol-3-yl}-2-methyl-6-propyl-phenoxy)-2-hydroxy-propyl]-2-hydroxy-acetamide;

N-[(S)-3-(4-{5-[2-(1-Ethyl-propyl)-6-methyl-pyridin-4-yl]-[1,2,4]oxadiazol-3-yl}-2-methyl-6-propyl-phenoxy)-2-hydroxy-propyl]-2-hydroxy-acetamide;

3-{4-[5-(2,6-Diethyl-pyridin-4-yl)-[1,2,4]oxadiazol-3-yl]-2,6-dimethyl-phenoxy}-propane-1,2-diol;

3-{4-[5-(2,6-Diethyl-pyridin-4-yl)-[1,2,4]oxadiazol-3-yl]-2-ethyl-6-methyl-phenoxy}-propane-1,2-diol;

N-((S)-3-{4-[5-(2,6-Diethyl-pyridin-4-yl)-[1,3,4]oxadiazol-2-yl]-2,6-dimethyl-phenoxy}-2-hydroxy-propyl)-2-hydroxy-acetamide;

N-(3-{4-[5-(2-Ethoxy-6-methyl-pyridin-4-yl)-[1,2,4]oxadiazol-3-yl]-2,6-dimethyl-phenoxy}-2-hydroxy-propyl)-2-hydroxy-acetamide;

(R)-3-{2-Ethyl-4-[5-(2-isobutyl-6-methoxy-pyridin-4-yl)-[1,2,4]oxadiazol-3-yl]-6-methyl-phenoxy}-propane-1,2-diol;

(S)-3-{2-Ethyl-4-[5-(2-isobutyl-6-methoxy-pyridin-4-yl)-[1,2,4]oxadiazol-3-yl]-6-methyl-phenoxy}-propane-1,2-diol;

N-((R)-3-{2-Ethyl-4-[5-(2-isobutyl-6-methoxy-pyridin-4-yl)-[1,2,4]oxadiazol-3-yl]-6-methyl-phenoxy}-2-hydroxy-propyl)-2-hydroxy-acetamide;

N-((S)-3-{2-Ethyl-4-[5-(2-isobutyl-6-methoxy-pyridin-4-yl)-[1,2,4]oxadiazol-3-yl]-6-methyl-phenoxy}-2-hydroxy-propyl)-2-hydroxy-acetamide;

(R)-3-{4-[5-(2-Cyclopentyl-6-methyl-pyridin-4-yl)-[1,2,4]oxadiazol-3-yl]-2-ethyl-6-methyl-phenoxy}-propane-1,2-diol;

(S)-3-{4-[5-(2-Cyclopentyl-6-methyl-pyridin-4-yl)-[1,2,4]oxadiazol-3-yl]-2-ethyl-6-methyl-phenoxy}-propane-1,2-diol;

N-((R)-3-{4-[5-(2-Cyclopentyl-6-methyl-pyridin-4-yl)-[1,2,4]oxadiazol-3-yl]-2-ethyl-6-methyl-phenoxy}-2-hydroxy-propyl)-2-hydroxy-acetamide; and N-((S)-3-{4-[5-(2-Cyclopentyl-6-methyl-pyridin-4-yl)-[1,2,4]oxadiazol-3-yl]-2-ethyl-6-methyl-phenoxy}-2-hydroxy-propyl)-2-hydroxy-acetamide;

in free or salt form.

18. A pharmaceutical composition comprising a compound according to claim 1, in free or pharmaceutically acceptable salt form, and a pharmaceutically acceptable carrier.

\* \* \* \* \*

UNITED STATES PATENT AND TRADEMARK OFFICE
CERTIFICATE OF CORRECTION

PATENT NO. : 8,580,824 B2  Page 1 of 1
APPLICATION NO. : 12/310801
DATED : November 12, 2013
INVENTOR(S) : Bolli et al.

It is certified that error appears in the above-identified patent and that said Letters Patent is hereby corrected as shown below:

In the Claims

Claim 17
Replace "pyridin-4-yl)1,2,4]oxadiazol" in Column 111, line 11 with "pyridin-4-yl)-[1,2,4]oxadiazol".

and

Replace "2-isobutyl-6-methyl-pyridin-4-yl)1,2,4]" in Column 111, line 13 with "2-isobutyl-6-methyl-pyridin-4-yl)-[1,2,4]".

Signed and Sealed this
Fourth Day of February, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,580,824 B2 | |
| APPLICATION NO. | : 12/310801 | |
| DATED | : November 12, 2013 | |
| INVENTOR(S) | : Bolli et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,011 days.

Signed and Sealed this
Eleventh Day of March, 2014

Michelle K. Lee
*Deputy Director of the United States Patent and Trademark Office*